United States Patent
Mittendorf et al.

(10) Patent No.: US 6,573,278 B2
(45) Date of Patent: *Jun. 3, 2003

(54) ARYL SULFONAMIDES AND ANALOGUES THEREOF AND THEIR USE IN THE TREATMENT OF NEURODEGENERATIVE DISEASES

(75) Inventors: Joachim Mittendorf, Wuppertal (DE); Jürgen Dressel, Radevormwald (DE); Michael Matzke, Wuppertal (DE); Jörg Keldenich, Wuppertal (DE); Klaus-Helmut Mohrs, Wuppertal (DE); Siegfried Raddatz, Köln (DE); Jürgen Franz, Witten (DE); Peter Spreyer, Düsseldorf (DE); Verena Vöhringer, Wuppertal (DE); Joachim Schuhmacher, Wuppertal (DE); Michael-Harold Rock, Valby (DK); Ervin Horváth, Leverkusen (DE); Arno Friedl, Bergisch Gladbach (DE); Frank Mauler, Overath (DE); Jean Marie Viktor de Vry, Rösrath (DE); Reinhard Jork, Haan (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/878,392

(22) Filed: Jun. 11, 2001

(65) Prior Publication Data

US 2002/0072529 A1 Jun. 13, 2002

Related U.S. Application Data

(62) Division of application No. 09/367,456, filed as application No. PCT/EP98/00716 on Feb. 10, 1998, now Pat. No. 6,262,112.

(30) Foreign Application Priority Data

Feb. 21, 1997 (DE) .......................................... 197 06 902
Sep. 17, 1997 (DE) .......................................... 197 40 785

(51) Int. Cl.$^7$ ........................ C07D 401/02; A61K 31/47
(52) U.S. Cl. ........................ 514/307; 514/311; 514/314; 514/339; 514/347; 514/415; 514/605; 514/711; 546/148; 546/149; 546/178; 546/277.4; 546/294; 548/482; 564/96; 564/97; 564/99; 568/631; 568/632; 568/633
(58) Field of Search .............................. 546/148, 149, 546/178, 277.4, 294; 548/482; 564/96, 97, 99; 568/631, 632, 633; 514/307, 311, 314, 339, 347, 415, 605, 711; 558/517, 54

(56) References Cited

U.S. PATENT DOCUMENTS

| 3,462,473 A | 8/1969 | Nelson et al. ................. 558/58 |
| 4,931,457 A | 6/1990 | Effland ........................ 514/349 |
| 5,532,237 A | 7/1996 | Gallant et al. ............ 514/235.2 |
| 6,262,112 B1 * | 7/2001 | Mittendorf et al. ........... 558/54 |

FOREIGN PATENT DOCUMENTS

| DE | 19 42 264 | 2/1970 |
| DE | 21 36 828 | 2/1973 |
| EP | 0 261 539 | 3/1988 |

OTHER PUBLICATIONS

Chemical Abstracts, vol. 78, No. 21, (1973); Abstract No. 135804w, Shein et al.: "Preparationof phenyl ethers condensation of aromatic bromo derivivtives with phenels". page 341, XP002068305; and IZV.SIB.. OTD.AKAD.NAUK.SSSR.,SER.HIM NAUK . . . , No. 1, pp.104–107.

* cited by examiner

Primary Examiner—Zinna Northington Davis
(74) Attorney, Agent, or Firm—Norris McLaughlin & Marcus

(57) ABSTRACT

The present invention relates to new aryl ether sulphonamides and analogues, processes for their preparation and their use for the treatment of neurodegenerative disorders, in particular for the prophylaxis and treatment of neurodegenerative disorders, in particular for the treatment of cerebral apoplexy and craniocerebral trauma.

7 Claims, No Drawings

ARYL SULFONAMIDES AND ANALOGUES THEREOF AND THEIR USE IN THE TREATMENT OF NEURODEGENERATIVE DISEASES

This application is a division of U.S. Ser. No. 09/367,456, filed on Nov. 15, 1999, now U.S. Pat. No. 6,262,112 B1, which is a 371 of PCT/EP98/00716, filed on Feb. 10, 1998.

The present invention relates to new arylsulfonamides and analogues, processes for their preparation and their use for the prophylaxis and treatment of neurodegenerative disorders, in particular for the treatment of cerebral apoplexy and craniocerebral trauma.

$\Delta^9$-Tetrahydrocannabinol ($\Delta^9$-THC) and, to a small extent, also $\Delta^8$-THC are the biologically active constituents in extracts of the plant Cannabis sativa (marihuana, hashish) and are responsible for the effects on the human central nervous system (CNS). Potential historical and contemporary therapeutic uses of cannabis preparations include, inter alia, analgesia, emesis, anorexia, glaucoma and mobility disorders.

Until now, two subtypes of cannabinoid receptors and a splice variant have been identified. The CB1 receptor (Nature 1990, 346, 561) and a splice variant CB1a (J. Biol. Chem. 1995, 270, 3726) are mainly localized in the central nervous system. The CB2 receptor was mainly found in the peripheral tissue, in particular in leucocytes, spleen and macrophages (Eur. J. Biochem. 1995, 232, 54).

CB1 and CB2 receptors have seven transmembrane regions and belong to the family of G protein receptors. Both receptors are negatively coupled via $G_i/G_o$ protein to adenylate cyclase and possibly negatively coupled to the presynaptic release of glutamates (J. Neurosci. 1996, 16, 4322). CB1 receptors are moreover positively coupled to potassium channels and also negatively coupled to N- and Q-type calcium channels.

Four classes of CB1 receptor agonists are known to date; classical cannabinoids, such as, for example, $\Delta^9$-THC, non-classical cannabinoids, aminoalkylindoles and eicosanoids. The latter include the generally accepted endogenous CB1 receptor agonist anandamide.

It is additionally known that cerebral apoplexy is a consequence of a sudden circulatory disorder of a human brain region with subsequent functional losses, with corresponding neurological and/or physiological symptoms. The causes of cerebral apoplexy can lie in cerebral haemorrhages (e.g. after a vascular tear in hypertension, arteriosclerosis and aneurysms) and ischaemia (e.g due to a blood pressure fall crisis or embolism). The functional losses in the brain lead to a degeneration or destruction of the brain cells (Journal of Cerebral Blood Flow and Metabolism 1981, 1, 155; Chem. Eng. News 1996 (May 13), 41; Trends Pharmacol. Sci. 1996, 17, 227)). Cranial cerebral trauma is understood as meaning covered and open cranial injuries with involvement of the brain The present invention relates to compounds of the general formula (I)

in which $R^1$ represents $(C_6-C_{10})$-aryl, quinolyl, isoquinolyl or a radical of the formula

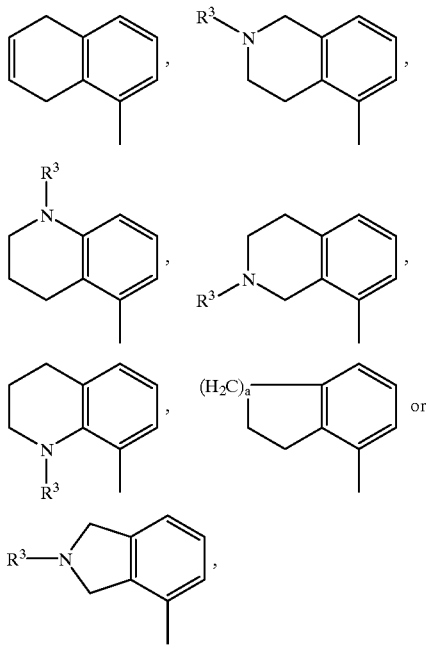

in which a denotes a number 1 or 2, $R^3$ denotes hydrogen, $(C_2-C_6)$-alkenyl, $(C_1-C_6)$-alkyl or $(C_1-C_6)$-acyl, and where all the abovementioned ring systems and radicals are optionally substituted, if appropriate geminally, by one or more, identical or different substituents which are selected from the group which consists of:

halogen, carboxyl, hydroxyl, phenyl, $(C_1-C_6)$-alkoxy, $(C_1-C_6)$-alkoxycarbonyl, $(C_1-C_8)$-alkyl, which, for its part, can be substituted by halogen, $(C_1-C_6)$-alkylsulphonyloxy, azide, amino, mono$(C_1-C_6)$-alkylamino, di$(C_1-C_6)$-alkylamino or hydroxyl, a group of the formula —$(CO)_b$—$NR^4R^5$, in which b denotes a number 0 or 1, $R^4$ and $R^5$ are identical or different and independently of one another denote hydrogen, phenyl, $(C_1-C_6)$-acyl, cyclo$(C_4-C_7)$-acyl, benzoyl or $(C_1-C_6)$-alkyl which is optionally substituted by amino, mono $(C_1-C_6)$-alkylamino, di$(C_1-C_6)$-alkylamino, or $R^4$ and $R^5$, together with the nitrogen atom, form a 5- or -membered saturated heterocycle which can optionally contain one or more further heteroatoms from the group consisting of S and O and/or one or more radicals of the formula —$NR^8$, in which $R^8$ denotes hydrogen, $(C_1-C_6)$-alkyl or $(C_1-C_6)$-acyl, and a group of the formula —$NR^6$—$SO_2$—$R^7$ in which $R^6$ denotes hydrogen, phenyl, $(C_1-C_6)$-alkyl or $(C_1-C_6)$-acyl, $R^7$ denotes phenyl or $(C_1-C_6)$-alkyl, A and E are identical or different and represent a bond or $(C_1-C_4)$-alkylene, D represents an oxygen atom or a radical of the formula —$S(O)_c$— or —$N(R^9)$—, in which c denotes a number 0, 1 or 2, $R^9$ denotes hydrogen, $(C_1-C_6)$-alkyl or $(C_1-C_6)$-acyl, G represents doubly bonded $(C_6-C_{10})$-aryl or a doubly bonded 5- to 7-membered aromatic heterocycle having up to 3 heteroatoms from the group consisting of S, N and/or O, each of which is optionally substituted by one or more, identical or different substituents which are selected from the group which consists of:

hydroxyl, trifluoromethyl, carboxyl, halogen, $(C_1-C_6)$-alkyl, hydroxy$(C_1-C_6)$-alkyl, $(C_1-C_6)$-alkoxy, $(C_1-C_6)$-alkoxycarbonyl, and also groups of the formulae —CO—O—$(CH_2)_d$—$NR^{10}$—$R^{11}$, —$NR^{12}$—$SO_2R^{13}$, —$(CH_2)_e$—$(CO)_f$—$NR^{14}R^{15}$ and —$OR^{16}$, in which d denotes a number 1, 2, 3 or 4, e and f are identical or different and denote a number 0 or 1, $R^{10}$ and $R^{11}$ have the meaning of $R^4$ and $R^5$ indicated above and are identical to or different from this, $R^{12}$ has the meaning of $R^6$ indicated above and is identical to or different from this, $R^{13}$ has the meaning of $R^7$ indicated above and is identical to or different from this, $R^{14}$ and $R^{15}$ have the meaning of $R^4$ and $R^5$ indicated above and are identical to or different from this, or independently of one another represents a radical of the formula —$(CH_2)_g$—$NR^{17}R^{18}$, in which g denotes a number 1, 2, 3 or 4, and $R^{17}$ and $R^{18}$ have the meaning of $R^4$ and $R^5$ indicated above and are identical to or different from this, $R^{16}$ denotes $(C_6-C_{10})$-aryl, L represents a radical of the formula

—O—, —NH—,

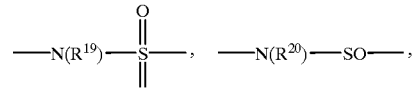

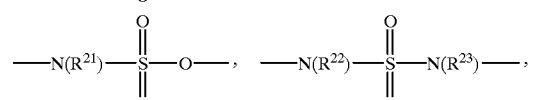

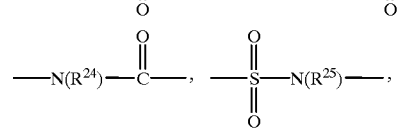

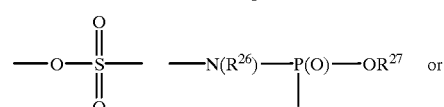

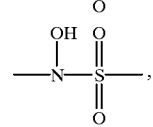

where the bonding of the radicals to G takes place at the left bond, and in which $R^{19}$, $R^{20}$, $R^{21}$, $R^{22}$, $R^{23}$, $R^{24}$, $R^{25}$, $R^{26}$ and $R^{27}$ are identical or different and denote hydrogen or $(C_1-C_4)$-alkyl, or $R^{19}$ denotes a radical of the formula —$SO_2R^2$, $R^2$ represents $(C_6-C_{10})$-aryl or a 5- to 7-membered saturated or aromatic heterocycle having up to 3 heteroatoms from the group consisting of S, N and/or O, each of which is optionally substituted by one or more, identical or different substituents which are selected from the group which consists of:

halogen, trifluoromethyl, nitro, amino and $(C_1-C_6)$-alkyl, or represents the radical of the formula

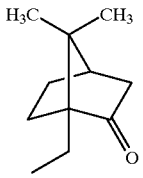

or morpholine, or represents $C_3-C_8$-cycloalkyl, or represents $(C_1-C_{12})$-alkyl, $(C_2-C_{12})$-alkenyl or $(C_2-C_{12})$-alkinyl, each of which is optionally substituted by one or more, identical or different substituents which are selected from the group which consists of:

halogen, trifluoromethyl, hydroxyl, cyano, azido, $(C_1-C_6)$-alkoxy, $(C_1-C_6)$-perfluoroalkoxy, partially fluorinated $(C_1-C_6)$-alkoxy, a radical of the formula

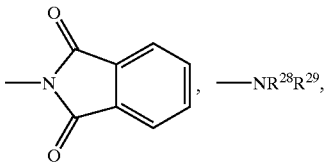

in which $R^{28}$ and $R^{29}$ have the meaning of $R^4$ and $R^5$ indicated above and are identical to or different from this, phenyl, optionally substituted by one or more, identical or different substituents which are selected from the group which consists of:

halogen, nitro, hydroxyl, $(C_1-C_6)$-alkyl, $(C_1-C_6)$-alkoxy and a group of the formula —$NR^{30}R^{31}$, in which $R^{30}$ and $R^{31}$ are identical or different and denote hydrogen or $(C_1-C_6)$-alkyl or $(C_1-C_6)$-acyl, and a 5- to 6-membered aromatic heterocycle having up to three heteroatoms from the group consisting of S, N and/or O, optionally substituted by one or more, identical or different substituents which are selected from the group which consists of:

halogen, nitro, hydroxyl, $(C_1-C_6)$-alkyl, $(C_1-C_6)$-alkoxy and a group of the formula —$NR^{30}R^{31}$, in which $R^{30}$ and $R^{31}$ are as defined above, or L and $R^2$ together represent a radical of the formula

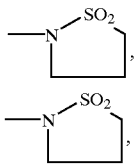

and their salts.

Preferred compounds of the formula (I) are those in which $R^1$ represents phenyl, naphthyl, quinolyl, isoquinolyl or a radical of the formula

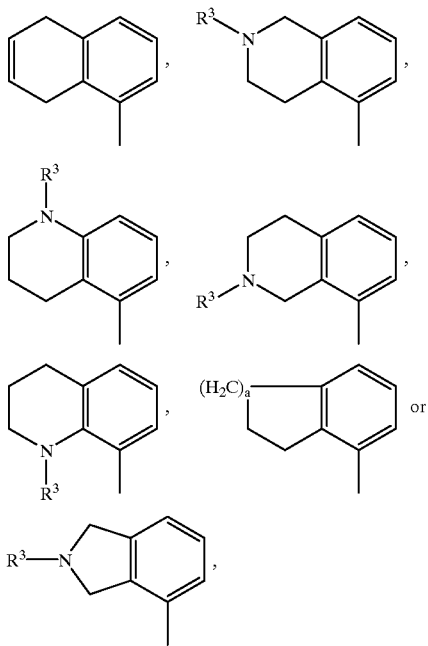

in which a denotes a number 1 or 2, $R^3$ denotes hydrogen. $(C_2-C_4)$-alkenyl, $(C_1-C_4)$-alkyl or $(C_1-C_4)$-acyl, and where all the abovementioned ring systems and radicals are optionally substituted, if appropriate geminally, by one or more, identical or different substituents which are selected from the group which consists of:

halogen, carboxyl, hydroxyl, phenyl, $(C_1-C_4)$-alkoxy, $(C_1-C_5)$-alkoxycarbonyl, $(C_1-C_6)$-alkyl which, for its part, can be substituted by halogen, $(C_1-C_4)$-alkylsulphonyloxy, azide, amino, mono$(C_1-C_4)$-alkylamino, di$(C_1-C_4)$-alkylamino or hydroxyl, a group of the formula $-(CO)_b-NR^4R^5$ in which b denotes a number 0 or 1, $R^4$ and $R^5$ are identical or different and independently of one another denote hydrogen, phenyl, $(C_1-C_4)$-acyl, cyclo$(C_4-C_7)$-acyl, benzoyl or $(C_1-C_4)$-alkyl which is optionally substituted by amino, mono$(C_1-C_4)$-alkylamino, di$(C_1-C_4)$-alkyl, or $R^4$ and $R^5$, together with the nitrogen atom, form a morpholine, piperidine or N-methylpiperazine ring, and a group of the formula $-NR^6-SO_2-R^7$ in which $R^6$ denotes hydrogen, phenyl, $(C_1-C_4)$-alkyl or $(C_1-C_4)$-acyl and $R^7$ denotes phenyl or $(C_1-C_5)$-alkyl, A and E are identical or different and represent a bond or $(C_1-C_4)$-alkylene, D represents an oxygen atom or a radical of the formula $-S(O)_c-$ or $-NR^9-$, in which c denotes a number 0, 1 or 2, $R^9$ denotes hydrogen or $(C_1-C_4)$-alkyl or $(C_1-C_4)$-acyl, G represents doubly bonded phenyl, naphthyl, pyrimidyl, pyridazinyl or pyridyl, each of which is optionally substituted by one or more, identical or different substituents which are selected from the group which consists of:

hydroxyl, trifluoromethyl, carboxyl, halogen, $(C_1-C_4)$-alkyl, hydroxy$(C_1-C_4)$alkyl, $(C_1-C_4)$-alkoxy, $(C_1-C_4)$-alkoxycarbonyl, and also groups of the formulae

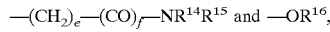

in which d denotes a number 1, 2, 3 or 4, e and f are identical or different and denote a number 0 or 1, $R^{10}$ and $R^{11}$ have the meaning of $R^4$ and $R^5$ indicated above and are identical to or different from this, $R^{12}$ has the meaning of $R^6$ indicated above and is identical to or different from this, $R^{13}$ has the meaning of $R^7$ indicated above and is identical to or different from this, $R^{14}$ and $R^{15}$ have the meaning of $R^4$ and $R^5$ indicated above and are identical to or different from this, or independently of one another represent a radical of the formula

in which g denotes a number 1, 2 or 3, and $R^{17}$ and $R^{18}$ have the meaning of $R^{10}$ and $R^{11}$ indicated above and are identical to or different from this, $R^{16}$ denotes phenyl or naphthyl, L represents a radical of the formula

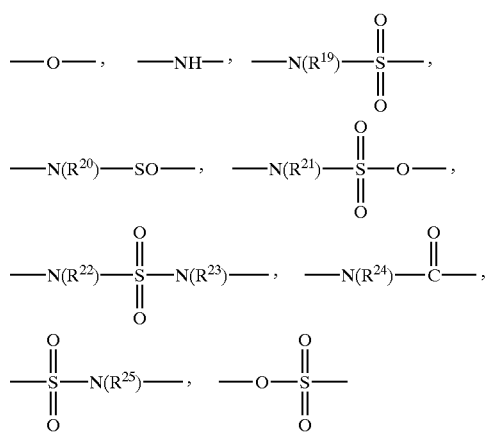

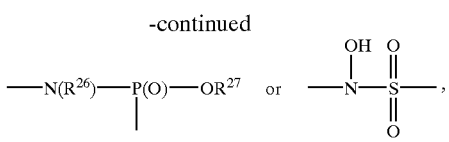

where the bonding of the radicals to G takes place at the left bond,
and
in which
$R^{19}$, $R^{20}$, $R^{21}$, $R^{22}$, $R^{23}$, $R^{24}$, $R^{25}$, $R^{26}$ and $R^{27}$ are identical or different and denote hydrogen or $(C_1-C_3)$-alkyl, or
$R^{19}$ denotes a radical of the formula $-SO_2R^2$,
$R^2$ represents phenyl, naphthyl, pyridyl, furyl, thienyl or pyrimidyl, each of which is optionally substituted by one or more, identical or different substituents which are selected from the group which consists of:
halogen, amino, trifluoromethyl, nitro and $(C_1-C_4)$-alkyl, or
represents the radical of the formula

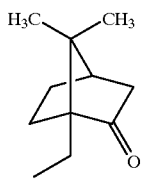

or morpholine,
or
represents cyclopropyl, cyclohexyl or cyclopentyl, or
represents $(C_1-C_{10})$-alkyl, $(C_2-C_{10})$-alkenyl or $(C_2-C_{10})$-alkinyl, each of which is optionally substituted by one or more, identical or different substituents which are selected from the group which consists of:
halogen, trifluoromethyl, hydroxyl, azido, $(C_1-C_4)$-alkoxy, $(C_1-C_5)$-perfluoroalkoxy, partially fluorinated $(C_1-C_4)$-alkoxy, a radical of the formula

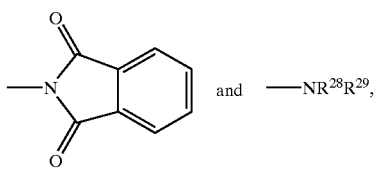

in which
$R^{28}$ and $R^{29}$ have the meaning of $R^4$ and $R^5$ indicated above and are identical to or different from this,
phenyl, optionally substituted by one or more, identical or different substituents which are selected from the group which consists of:
halogen, nitro, hydroxyl, $(C_1-C_4)$-alkyl, $(C_1-C_4)$-alkoxy and a group of the formula $-NR^{30}R^{31}$,
in which $R^{30}$ and $R^{31}$ are identical or different and denote hydrogen or $(C_1-C_4)$-alkyl or $(C_1-C_4)$-acyl,
pyridyl and pyrimidyl, optionally substituted by one or more, identical or different substituents which are selected from the group which consists of:
halogen, nitro, hydroxyl, $(C_1-C_4)$-alkyl, $(C_1-C_4)$-alkoxy and a group of the formula $-NR^{30}R^{31}$,
in which $R^{30}$ and $R^{31}$ are as defined above, or
L and $R^2$ together represent a radical of the formula

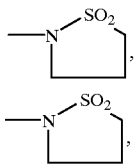

and their salts
Particularly preferred compounds of the formula (I) are those in which
$R^1$ represents phenyl, naphthyl, quinolyl, isoquinolyl or a radical of the formula

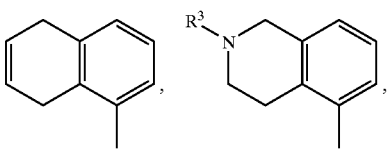

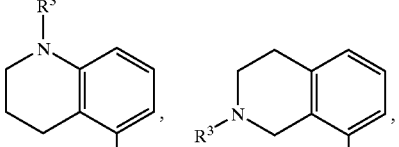

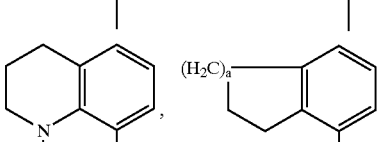

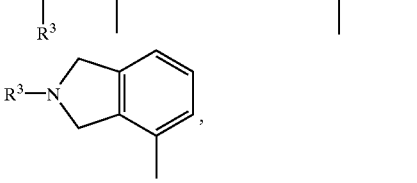

in which
a denotes a number 1 or 2,
$R^3$ denotes hydrogen, $(C_2-C_3)$-alkenyl, $(C_1-C_3)$-alkyl or $(C_1-C_3)$-acyl,
and where all the abovementioned ring systems are optionally substituted, if appropriate geminally, by one or more, identical or different substituents which are selected from the group which consists of:
chlorine, fluorine, carboxyl, hydroxyl, phenyl, $(C_1-C_3)$-alkoxy, $(C_1-C_4)$-alkoxycarbonyl, $(C_1-C_4)$-alkyl which, for its part, can be substituted by chlorine, methylsulphonyloxy or hydroxyl,
a group of the formula $-(CO)_b-NR^4R^5$
in which
b denotes a number 0 or 1,
$R^4$ and $R^5$ are identical or different and independently of one another denote hydrogen, $(C_1-C_3)$-acyl, cyclo$(C_4-C_6)$-acyl, benzoyl or $(C_1-C_3)$-alkyl which is optionally substituted by amino, mono$(C_1-C_3)$-alkylamino, di$(C_1-C_3)$-alkyl amino,
or
$R^4$ and $R^5$, together with the nitrogen atom, form a morpholine, piperidine or N-methylpiperazine ring, and a group of the formula —NR$^6$—SO$_2$—R$^7$ in which R$^6$ denotes hydrogen, (C$_1$–C$_3$)-alkyl or (C$_1$–C$_3$)-acyl and R$^7$ denotes phenyl or (C$_1$–C$_4$)-alkyl, A and E are identical or different and represent a bond or (C$_1$–C$_3$)-alkyl, D represents an oxygen atom or a radical of the formula —S(O)$_c$— or —NR$^9$—, in which c denotes a number 0, 1 or 2, R$^9$ denotes hydrogen or (C$_1$–C$_3$)-alkyl or (C$_1$–C$_3$)-acyl, G represents doubly bonded phenyl, naphthyl, pyrimidyl, pyridazinyl or pyridyl, each of which is optionally substituted by one or more, identical or different substituents which are selected from the group which consists of:

hydroxyl, trifluoromethyl, carboxyl, fluorine, chlorine, bromine, (C$_1$–C$_3$)-alkyl, hydroxy(C$_1$–C$_3$)alkyl, (C$_1$–C$_3$)-alkoxy, (C$_1$–C$_3$)-alkoxycarbonyl, and also groups of the formulae —CO—O—(CH$_2$)$_d$—NR$^{10}$R$^{11}$, —NR$^{12}$—SO$_2$R$^{13}$, —(CH$_2$)$_e$—(CO)$_f$—NR$^{14}$R$^{15}$, —CH$_2$OH and —OR$^{16}$, in which d denotes a number 1, 2 or 3, e and f are identical or different and denote a number 0 or 1, R$^{10}$ and R$^{11}$ denote hydrogen or methyl, R$^{12}$ denotes hydrogen, R$^{13}$ denotes (C$_1$–C$_4$)-alkyl, R$^{14}$ and R$^{15}$ have the meaning of R$^4$ and R$^5$ indicated above and are identical to or different from this, or denote a radical of the formula —(CH$_2$)$_g$—NR$^{17}$R$^{18}$, in which g denotes a number 1, 2 or 3, and R$^{17}$ and R$^{18}$ denote hydrogen or methyl, or R$^{14}$ and R$^{15}$, together with the nitrogen atom, form a radical of the formula

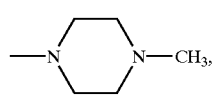

R$^{16}$ denotes phenyl or naphthyl,

L represents a radical of the formula

—O—, —NH—, —N(R$^{19}$)—S(=O)$_2$—,

—N(R$^{20}$)—SO—, —N(R$^{21}$)—S(=O)$_2$—O—,

—N(R$^{22}$)—S(=O)—N(R$^{23}$)—, —N(R$^{24}$)—C(=O)—,

-continued

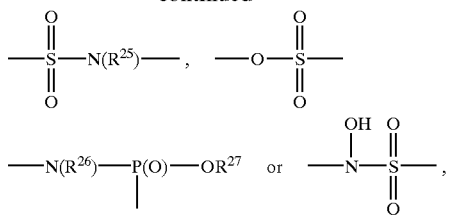

where the bonding of the radicals to G takes place at the left bond, and in which R$^{19}$, R$^{20}$, R$^{21}$, R$^{22}$, R$^{23}$, R$^{24}$, R$^{25}$, R$^{26}$ and R$^{27}$ are identical or different and denote hydrogen, methyl or ethyl, or R$^{19}$ denote a radical of the formula —SO$_2$R$^2$, R$^2$ represents phenyl, furyl or pyridyl, each of which is optionally substituted by one or more, identical or different substituents which are selected from the group which consists of: fluorine, chlorine, bromine or trifluoromethyl, or represents the radical of the formula

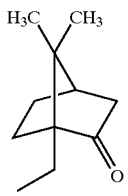

or morpholine, or represents cyclopentyl or cyclohexyl, or represents (C$_1$–C$_8$)-alkyl, (C$_2$–C$_8$)-alkenyl or (C$_2$–C$_8$)-alkinyl, each of which is optionally substituted by one or more, identical or different substituents which are selected from the group which consists of:

fluorine, chlorine, bromine, trifluoromethyl, hydroxyl, azido, (C$_1$–C$_3$)-alkoxy, (C$_1$–C$_4$)-perfluoroalkoxy, trifluoromethyl-substituted (C$_1$–C$_4$)-alkoxy, a radical of the formula

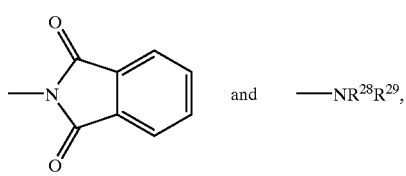

in which

R$^{28}$ and R$^{29}$ denote hydrogen or methyl, phenyl, pyridyl and pyrimidyl, optionally substituted by one or more, identical or different substituents which are selected from the group which consists of:

fluorine, chlorine, bromine, nitro, hydroxyl, (C$_1$–C$_3$)-alkyl, (C$_1$–C$_3$)-alkoxy and a group of the formula —NR$^{30}$R$^{31}$, in which R$^{30}$ and R$^{31}$ are identical or different and denote hydrogen, methyl or methylcarbonyl, or L and $R^2$ together represent a radical of the formula

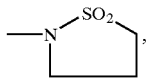

and their salts

The present invention also relates to compounds of the formula (I)
in which
$R^1$ represents $(C_6-C_{10})$-aryl, quinolyl or a radical of the formula

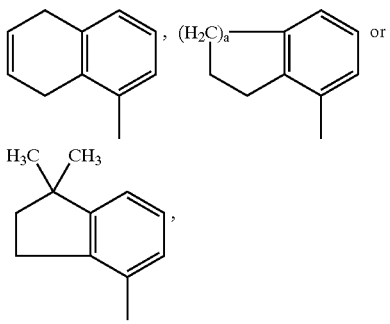

in which
a denotes a number 1 or 2,
and where all the abovementioned ring systems and radicals are optionally substituted, if appropriate geminally, by 1 to 3 identical or different substituents which are selected from the group which consists of:
  halogen, carboxyl, hydroxyl, $(C_1-C_6)$-alkoxy, $(C_1-C_6)$-alkoxycarbonyl, $(C_1-C_8)$-alkyl which, for its parts, can be substituted by halogen or hydroxyl,
  a group of the formula $-(CO)_b-NR^4R^5$
  in which
    b denotes a number 0 or 1,
    $R^4$ and $R^5$ are identical or different and denote hydrogen, phenyl or $(C_1-C_6)$-alkyl,
  and
  a group of the formula $-NR^6-SO_2-R^7$
  in which
    $R^6$ denotes hydrogen, phenyl or $(C_1-C_6)$-alkyl,
    $R^7$ denotes phenyl or $(C_1-C_6)$-alkyl,
A and E are identical or different and represent a bond or $(C_1-C_4)$-alkylene,
D represents an oxygen atom or a radical of the formula $-S(O)_c-$ or $-NH-$,
  in which
  c denotes a number 0, 1 or 2,
G represents doubly bonded $(C_6-C_{10})$-aryl or a double bonded 5- to 7-membered aromatic heterocycle having up to 3 heteroatoms from the group consisting of S, N and/or O, each of which is optionally substituted by up to three identical or different substituents which are selected from the group which consists of:
  hydroxyl, carboxyl, halogen, $(C_1-C_6)$-alkyl, hydroxy $(C_1-C_6)$alkyl, $(C_1-C_6)$-alkoxy, $(C_1-C_6)$-alkoxycarbonyl, and also groups of the formulae $-CO-O-(CH_2)_d-NR^{10}R^{11}$, $-NR^{12}-SO_2R^{13}$ and $-CO-NR^{14}R^{15}$ in which
  d denotes a number 1, 2, 3 or 4, $R^{10}$ and $R^{11}$ have the meaning of $R^4$ and $R^5$ indicated above and are identical to or different from this,
$R^{12}$ has the meaning of $R^6$ indicated above and is identical to or different from this,
$R^{13}$ has the meaning of $R^7$ indicated above and is identical to or different from this,
$R^{14}$ and $R^{15}$ have the meaning of $R^4$ and $R^5$ indicated above and are identical to or different from this, or together with the nitrogen atom form a 5- to 6-membered saturated heterocycle which can optionally additionally contain a further heteroatom from the group consisting of S and O or a group of the formula $-NH-$,
L represents a radical of the formula

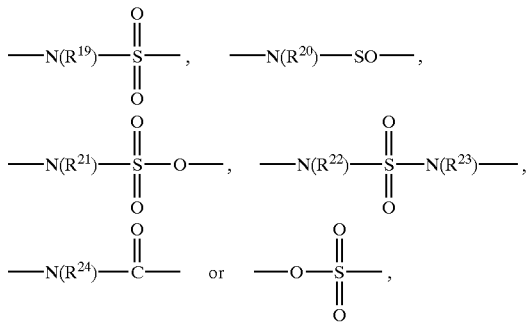

where the bonding of the radicals to G takes place at the left bond,
and in which $R^{19}$, $R^{20}$, $R^{21}$, $R^{22}$, $R^{23}$ and $R^{24}$ are identical or different and denote hydrogen or $(C_1-C_4)$-alkyl,
$R^2$ represents phenyl which is optionally substituted by halogen, trifluoromethyl, nitro, amino or $(C_1-C_6)$-alkyl,
$R^2$ represents the radical of the formula

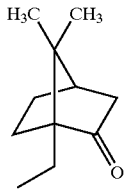

or morpholine,
or
represents perfluoroalkyl having up to 12 fluorine atoms,
or
represents $(C_1-C_{12})$-alkyl or $(C_2-C_{12})$-alkinyl, each of which is optionally substituted by halogen, trifluoromethyl, hydroxyl, azido or by a radical of the formula

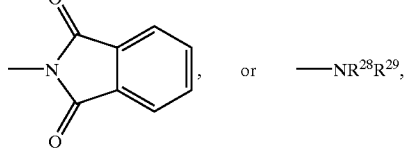

in which $R^{28}$ and $R^{29}$ have the meaning of $R^4$ and $R^5$ indicated above and are identical to or different from this, and/or are optionally substituted by phenyl or a 5- to 6-membered aromatic heterocycle having up to 3 heteroatoms from the group consisting of S, N and/or O, which, for their part, can be substituted up to 2 times identically or differently by halogen, nitro, hydroxyl, $(C_1-C_6)$-alkyl, $(C_1-C_6)$-alkoxy or by a group of the formula $-NR^{30}R^{31}$, in which $R^{30}$ and $R^{31}$ are identical or different and denote hydrogen, $(C_1-C_6)$-alkyl or $(C_1-C_6)$-acyl, L and $R^2$ together represent a radical of the formula

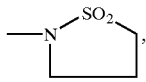

and their salts.

Very particularly preferred compounds of the formula (I) according to the invention are those
in which $R^1$ represents naphth-1-yl, optionally substituted by $(C_1-C_6)$-alkyl substituted by hydroxyl, $(C_1-C_6)$-acylamino, amino or $(C_1-C_6)$-alkoxy, indan-4-yl, substituted by hydroxy$(C_1-C_6)$-alkyl, a radical of the formula

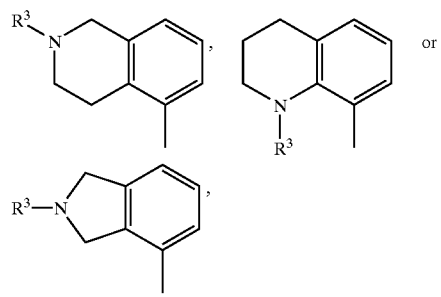

in which $R^3$ is $(C_1-C_6)$-alkyl,

E and A represent a bond,

D represents an oxygen atom,

G represents 1,3-phenylene, 1,4-phenylene or 2,5-pyridylene, each of which is optionally substituted by halogen, L represents a radical of the formula —NH—SO$_2$— or —O—SO$_2$— and $R^2$ represents $(C_1-C_6)$-alkyl which is optionally substituted by chlorine, trifluoromethyl, by a radical of the formula —O—CH$_2$—CF$_3$ or by phenyl or by pyridyl, which for their part can be substituted by bromine or chlorine, and their salts In particular, the following very particularly preferred compounds may be mentioned:

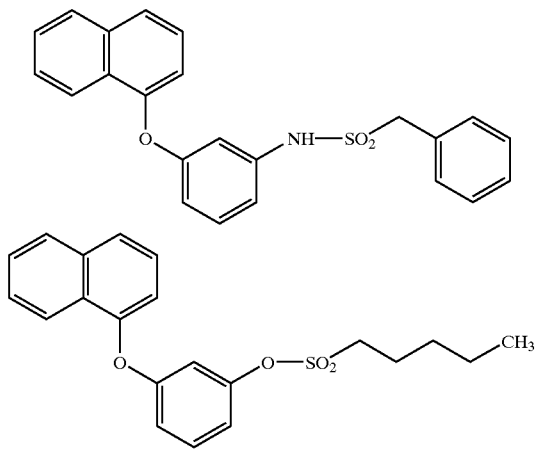

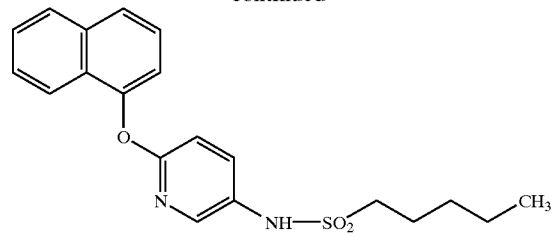

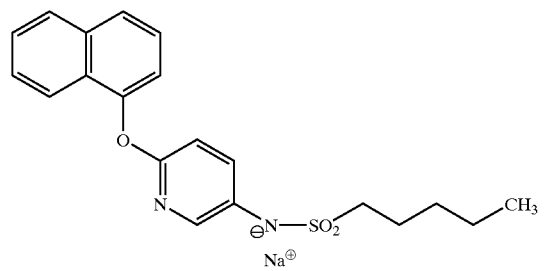

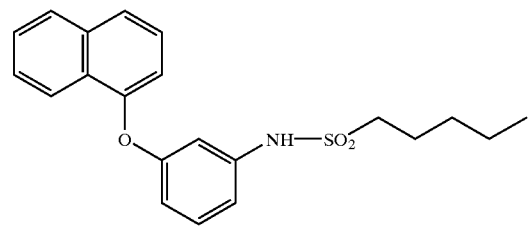

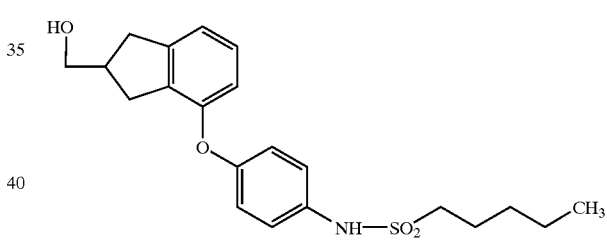

Racemate and Enantiomers

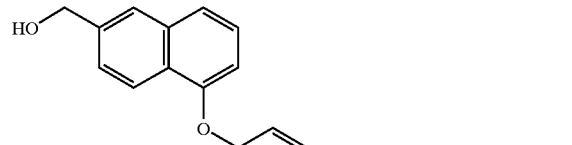

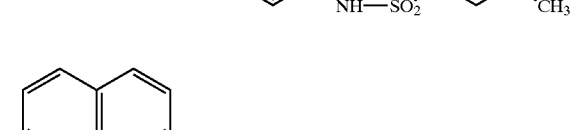

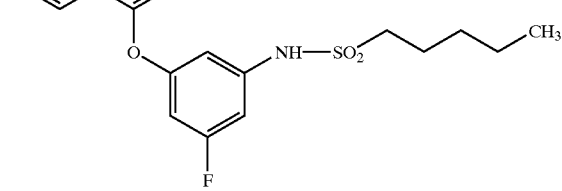

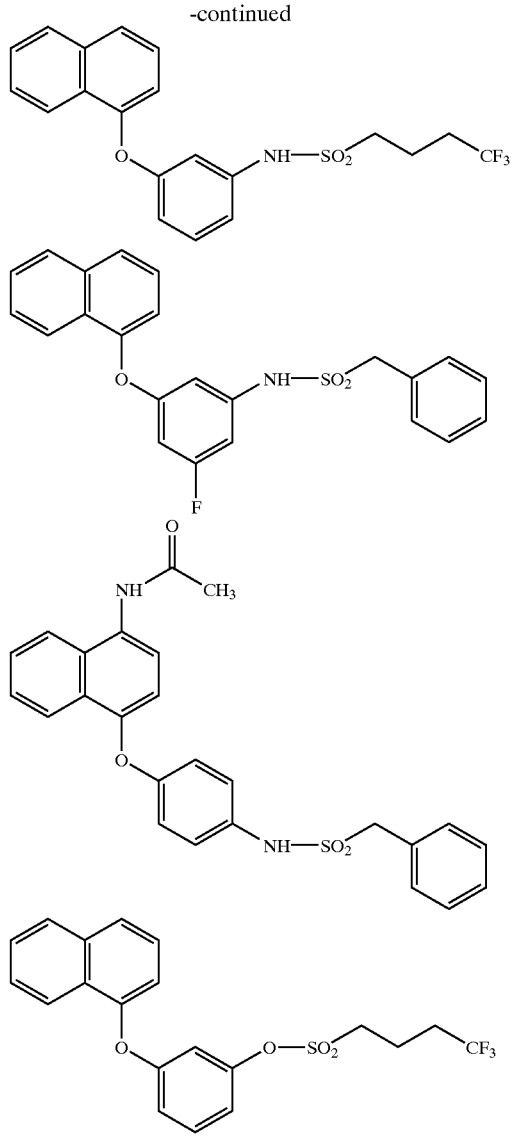
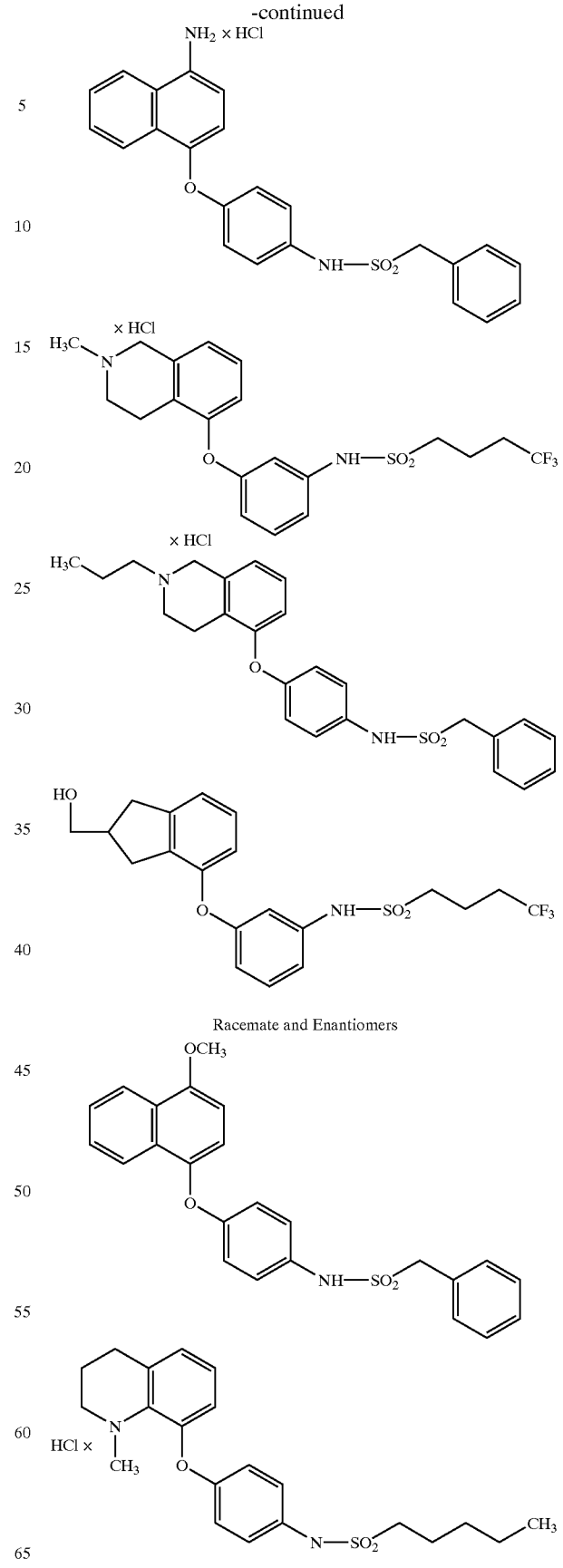

-continued
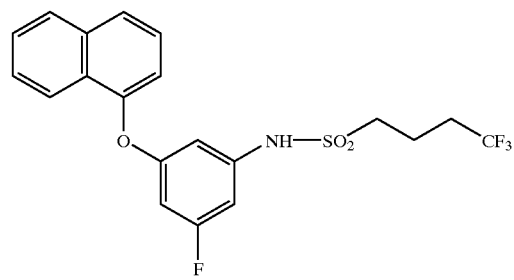
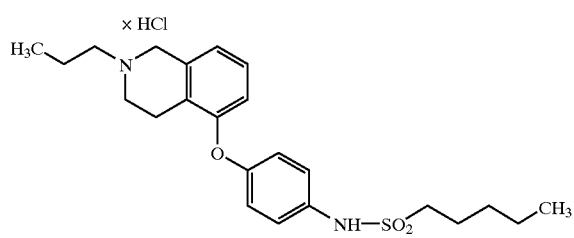
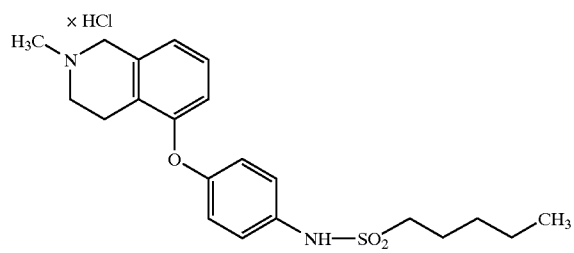
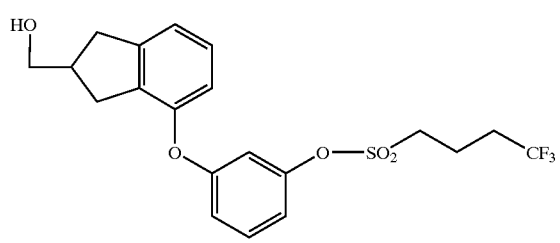
Racemate and Enantiomers
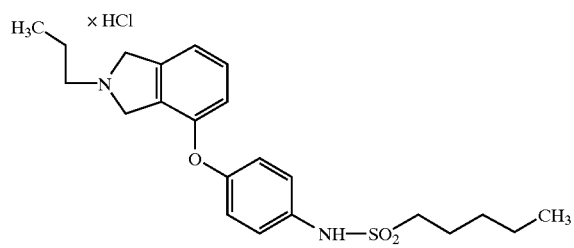
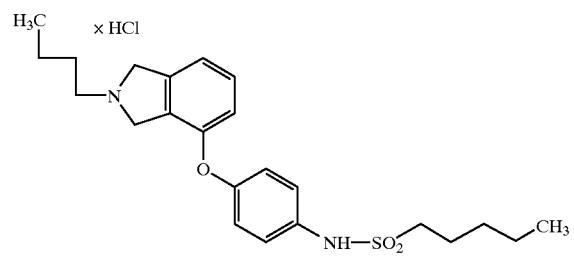
-continued
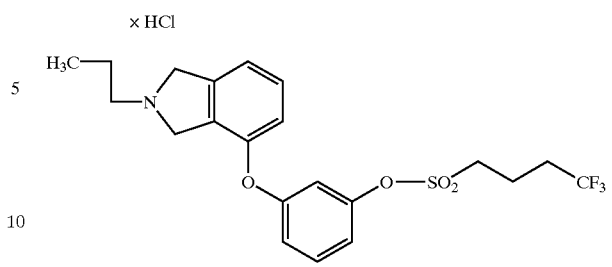
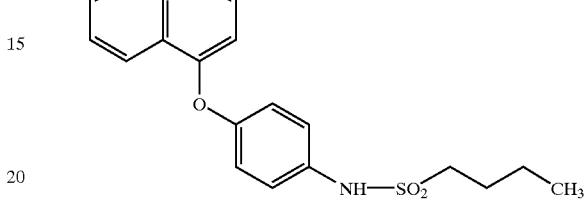
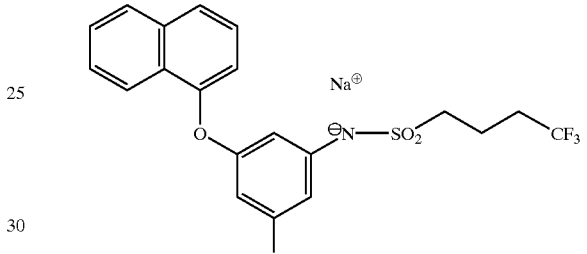
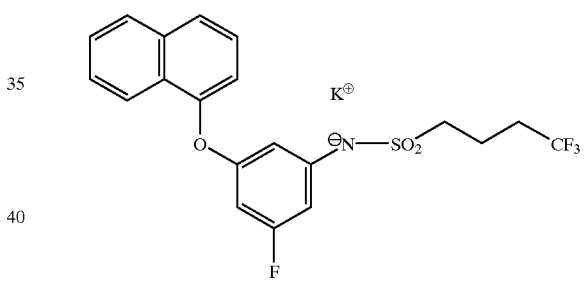
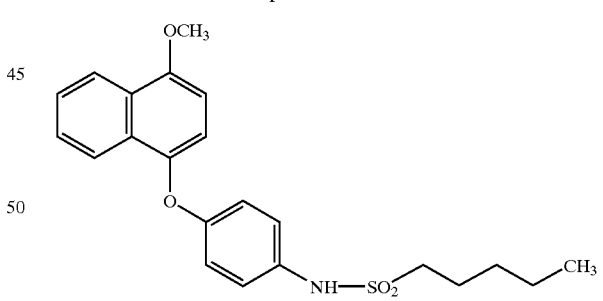
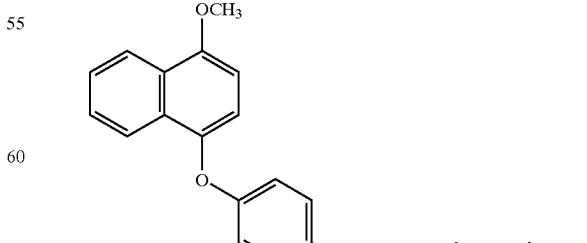

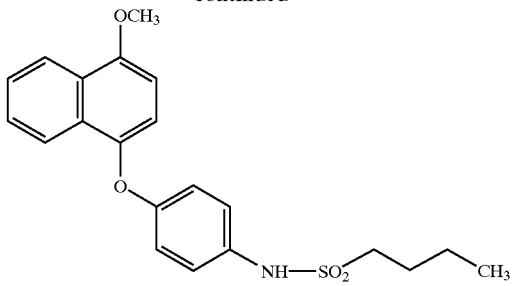

The compounds according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention. Those particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The present invention also includes ammonium compounds which can be prepared by conversion of the free amines by means of alkylation.

In the context of the present invention, the substituents in general have the following meaning:

($C_1$–$C_{12}$)-Alkyl in general represents, depending on the abovementioned substituents, a straight-chain or branched hydrocarbon radical having 1 to 12 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl.

($C_1$–$C_8$)-Alkyl having 1 to 8 carbon atoms, e.g. nonyl, decyl, undecyl, dodecyl, is preferred.

($C_2$–$C_{12}$)-Alkenyl in general represents, depending on the abovementioned substituents, a straight-chain or branched hydrocarbon radical having 2 to 6 and 2 to 20 carbon atoms and one or more, preferably having one or two, double bonds. The lower alkyl radical having 2 to 4 and 2 to 10 carbon atoms and a double bond is preferred. An alkenyl radical having 2 to 3 and 2 to 8 carbon atoms and a double bond is particularly preferred. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

($C_2$–$C_{12}$)-Alkinyl in general represents, depending on the abovementioned substituents, a straight-chain or branched hydrocarbon radical having 2 to 12 carbon atoms and one or more, preferably having one or two, triple bonds. The lower alkyl radical having 2 to approximately 10 carbon atoms and a triple bond is preferred. An alkyl radical having 2 to 8 carbon atoms and a triple bond is particularly preferred. Examples which may be mentioned are acetylene, 2-butine, 2-pentine and 2-hexine.

($C_1$–$C_6$)-Acyl in general represents, depending on the abovementioned substituents, straight-chain or branched lower alkyl having 1 to 6 carbon atoms which are bonded via a carbonyl group. Alkyl radicals having up to 4 carbon atoms are preferred. Alkyl radicals having up to 3 carbon atoms, for example, are very particularly preferred. Examples which may be mentioned are: acetyl, ethylcarbonyl, propylcarbonyl, isopropylcarbonyl, butylcarbonyl and isobutylcarbonyl.

($C_1$–$C_6$)-Alkoxy in general represents, depending on the abovementioned substituents, a straight-chain or branched hydrocarbon radical bonded via an oxygen atom and having 1 to 6 carbon atoms. Lower alkoxy having 1 to 4 carbon atoms is preferred. An alkoxy radical having 1 to 3 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

($C_1$–$C_6$)-Alkoxycarbonyl can be represented, for example, by the formula

Alkyl here represents a straight-chain or branched hydrocarbon radical having 1 to 6 carbon atoms. Lower alkoxycarbonyl having 1 to 4 carbon atoms in the alkyl moiety is preferred. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

($C_3$–$C_8$)-Cycloalkyl in general represents a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

Cyclo($C_4$–$C_7$)-acyl in general represents, depending on the abovementioned substituents, cyclopropylcarbonyl, cyclobutylcarbonyl, cyclopentylcarbonyl or cyclohexylcarbonyl.

($C_6$–$C_{10}$)-Aryl in general represents an aromatic radical having 6 to 10 carbon atoms. Preferred aryl radicals are phenyl and naphthyl.

($C_1$–$C_6$)-Perfluoroalkoxy in the context of the invention represents an alkoxy radical having 1 to 6 carbon atoms and 3 to 13 fluorine atoms. An alkoxy radical having 1 to 5 carbon atoms and 3 to 9 fluorine atoms is preferred.

($C_1$–$C_6$)-Partially fluorinated alkoxy in the context of the invention represents an alkoxy radical having 1 to 6 carbon atoms and 3 to 5 fluorine atoms. An alkoxy radical having 1 to 4 carbon atoms and 3 fluorine atoms is preferred. An alkoxy radical having 1 to 3 carbon atoms and which is substituted by trifluoromethyl is particularly preferred.

Halogen in the context of the invention represents fluorine, chlorine, bromine and iodine.

Aromatic, saturated and unsaturated heterocycles in the context of the invention, depending on the abovementioned substituents, in general represent a 5- to 7-membered or 5- to 6-membered, preferably 5- to 6-membered, heterocycle which can contain up to 3 heteroatoms from the group consisting of S, N and/or O and which can optionally also be bonded via a nitrogen atom. Examples which may be mentioned are: pyridyl, thienyl, furyl, pyrrolyl, pyrrolidinyl, piperazinyl, pyrimidyl, thiazolyl, oxazolyl, imidazolyl, morpholinyl or piperidyl. Pyridyl, furyl, morpholinyl, piperidyl and piperazinyl are preferred.

Leaving groups in the sense of the invention are groups which can be replaced by a nucleophile in a nucleophilic substitution (Streitwieser, A., Jr.; Heathcock, C. H. Organische Chemie, Verlag Chemie, 1980, p. 169ff). Preferred leaving groups are halides and sulphonic acid esters/anhydrides. A particularly preferred leaving group is chloride.

$(C_3-C_6)$-Ketone in the context of the invention represents a saturated or unsaturated ketone having 3 to 6 carbon atoms. Examples which may be mentioned are: acetone, butanone, but-1-en-3-one, but-1-in-3-one, pentan-3-one, pentan-2-one, pent-1-en-3-one, pent-1-in-3-one, penta-1,4-dien-3-one, 3-methylbutan-2-one, cyclopropyl methyl ketone, cyclopentanone, hexan-2-one, hexan-3-one, cyclohexanone, 2-methylcyclopentanone, 2-ethylcyclobutanone.

$(C_1-C_6)$-Aldehyde in the context of the invention represents a saturated or unsaturated aldehyde having 1 to 6 carbon atoms. Examples which may be mentioned are: formaldehyde, acetaldehyde, propionaldehyde, butyraldehyde, isobutyraldehyde, cyclopropylcarbaldehyde, but-2-enal, but-2-inal, pentanal, isopentanal, pivaldehyde, cyclobutylcarbaldehyde, 2-methylcyclopropylcarbaldehyde, pent-2-enal, pent-4-enal, hexanal, 2-cyclobutylacetaldehyde.

The compounds according to the invention can exist in stereoisomeric forms which either behave as image and mirror image (enantiomers), or which do not behave as image and mirror image (diastereomers). The invention relates both to the enantiomers or diastereomers and their respective mixtures. These mixtures of the enantiomers and diastereomers can be separated into the stereoisomerically uniform constituents in a known manner.

Processes for the preparation of the compounds of the general formula (I) according to the invention have additionally been found, characterized in that

[A] compounds of the general formula (II)

$$R^1-A-D-E-G-M-H \quad (II)$$

in which
$R^1$, A, D, E and G have the meaning indicated above and
M represents oxygen or $-N(R^{32})-$ and
$R^{32}$ is hydrogen or $(C_1-C_4)$-alkyl,
are reacted with compounds of the general formula (III)

$$R^{33}-Q-R^2 \quad (III)$$

in which
$R^2$ has the meaning indicated above,
$R^{33}$ represents halogen, preferably chlorine or iodine,
Q represents a radical of the formula $-SO_2-$, $-SO-$, $-CO-$, $-P(O)(OR^{27})-$ or a single bond,
in which
$R^{27}$ has the meaning indicated above,
to give compounds of the general formula (Ia)

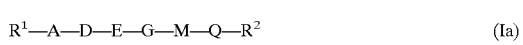

$$R^1-A-D-E-G-M-Q-R^2 \quad (Ia)$$

in which
$R^1$, A, D, E, G, M, Q and $R^2$ have the meaning indicated above, in inert solvents, if appropriate in the presence of a base, or
[B] compounds of the general formula (II) are reacted first with trialkylsilyl chlorosulphonates, preferably trimethylsilyl chlorosulphonates, treated with an acid and then reacted with a chlorinating agent, preferably phosphorus pentachloride, to give a compound of the general formula (IV)

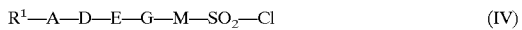

$$R^1-A-D-E-G-M-SO_2-Cl \quad (IV)$$

in which
$R^1$, A, D, E, G, and M have the meaning indicated above, and then reacted with compounds of the general formula (V)

$$H-T-R^2 \quad (V)$$

in which
$R^2$ has the meaning indicated above, and
T represents oxygen or nitrogen,
to give compounds of the general formula (Ib)

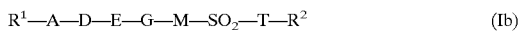

$$R^1-A-D-E-G-M-SO_2-T-R^2 \quad (Ib)$$

in which
$R^1$, A, D, E, G, M, T and $R^2$ have the meaning indicated above, in inert solvents in the presence of $Bzl-NEt_3^+Cl^-$ and a base,
or
[C] compounds of the general formula (VI)

$$R^1-A-D'-H \quad (VI)$$

in which
$R^1$ and A have the meaning indicated above and
D' represents oxygen, sulphur or $-N(R^9)-$ and
$R^9$ has the meaning indicated above,
are reacted with compounds of the general formula (VII)

$$R^{34}-E-G-SO_2-NH-R^2 \quad (VII)$$

in which
E, G and $R^2$ have the meaning indicated above and
$R^{34}$ represents a leaving group, preferably halogen, particularly preferably fluorine, chlorine or bromine,
to give compounds of the general formula (Ic)

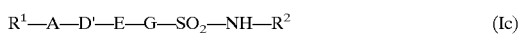

$$R^1-A-D'-E-G-SO_2-NH-R^2 \quad (Ic)$$

in which
$R^1$, A, D', E, G and $R^2$ have the meaning indicated above,
or
[D] compounds of the general formula (Id)

$$R^{37}-A-D-E-G-L-R^2 \quad (Id)$$

in which
A, D, E, G, L and $R^2$ have the meaning indicated above and
$R^{37}$ represents a radical of the formula

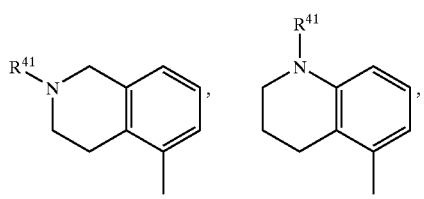

-continued

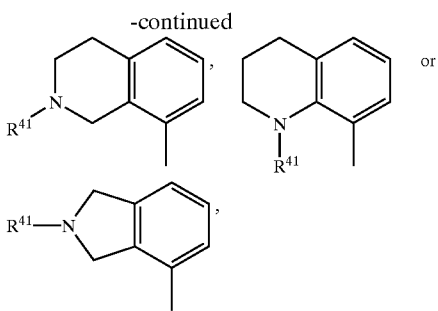

in which
R$^{41}$ represents (C$_1$–C$_6$)-alkyl,
are reacted with a chloroformic acid ester, preferably 1-(1-chloro)ethyl chloroformate or methyl chloroformate, and then with alcohols, preferably methanol, if appropriate in the presence of a base, to give compounds of the general formula (Ie)

in which
A, D, E, G, L and R$^2$ have the meaning indicated above
and
R$^{38}$ represents a radical of the formula

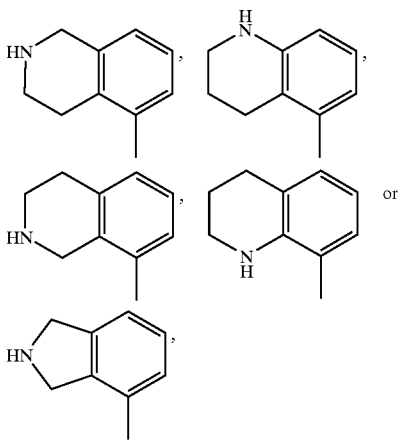

or
[E] compounds of the general formula (Ie) are reacted with (C$_1$–C$_6$)-ketones or (C$_1$–C$_6$)-aldehydes in the presence of a reducing agent, preferably sodium cyanoborohydride, if appropriate in the presence of an acid, to give compounds of the general formula (If)

in which
A, D, E, G, L and R$^2$ have the meaning indicated above
and
R$^{39}$ represents (C$_3$–C$_6$)-alkenyl or (C$_1$–C$_6$)-alkyl,
or
[F] compounds of the general formula (Ie) are reacted with compounds of the general formula (VIII)

in which
R$^3$ has the meaning indicated above,
R$^{35}$ represents a leaving group, preferably halogen, in inert solvents, if appropriate in the presence of a base, to give compounds of the general formula (Ig)

in which
A, D, E, G, L and R$^2$ have the meaning indicated above
and
R$^{40}$ represents a radical of the formula

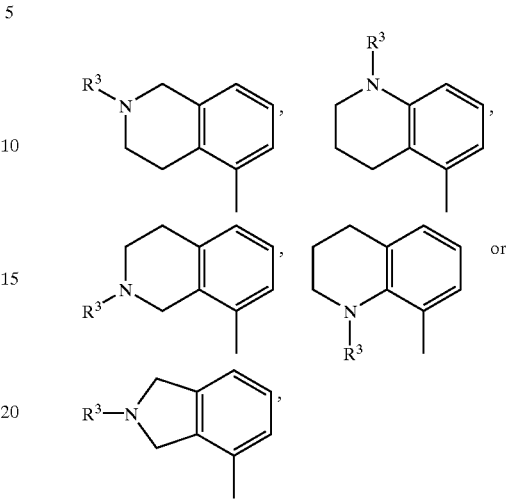

in which
R$^3$ has the meaning indicated above,
or
[G] compounds of the general formula (Ih)

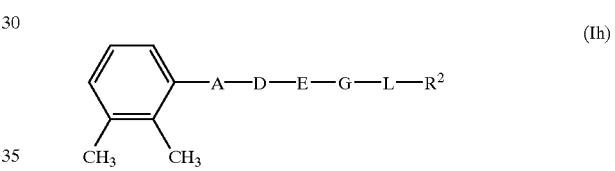

in which
A, D, E, G, L and R$^2$ have the meaning indicated above, are converted by means of free-radical bromination, for example with N-bromosuccinimide, in an inert solvent into compounds of the general formula (Ii)

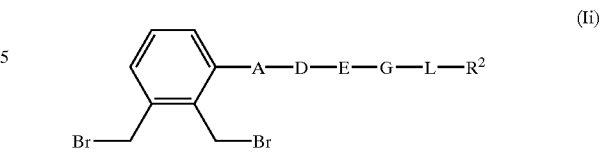

in which
A, D, E, G, L and R$^2$ have the meaning indicated above, and then reacted with compounds of the general formula (IX) or (X)

in which
R$^{42}$ represents (C$_1$–C$_6$)-alkyl and
R$^3$ has the meaning indicated above,
in inert solvents, if appropriate in the presence of a base, to give compounds of the general formula (Ij)

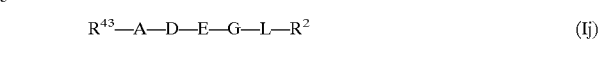

in which

A, D, E, G, L and R² have the abovementioned meaning and

R⁴³ represents

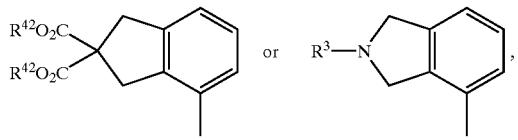

in which

R⁴² and R³ have the abovementioned meaning, and, if appropriate, the abovementioned substituents are introduced and derivatized according to customary methods, and if D=—SO— or —SO₂—, starting from the corresponding thioethers (D=S), an oxidation is carried out according to customary methods, and in the case of the ammonium compounds, starting from the corresponding amines, an alkylation is carried out.

The processes according to the invention can be illustrated by way of example by the following reaction schemes:

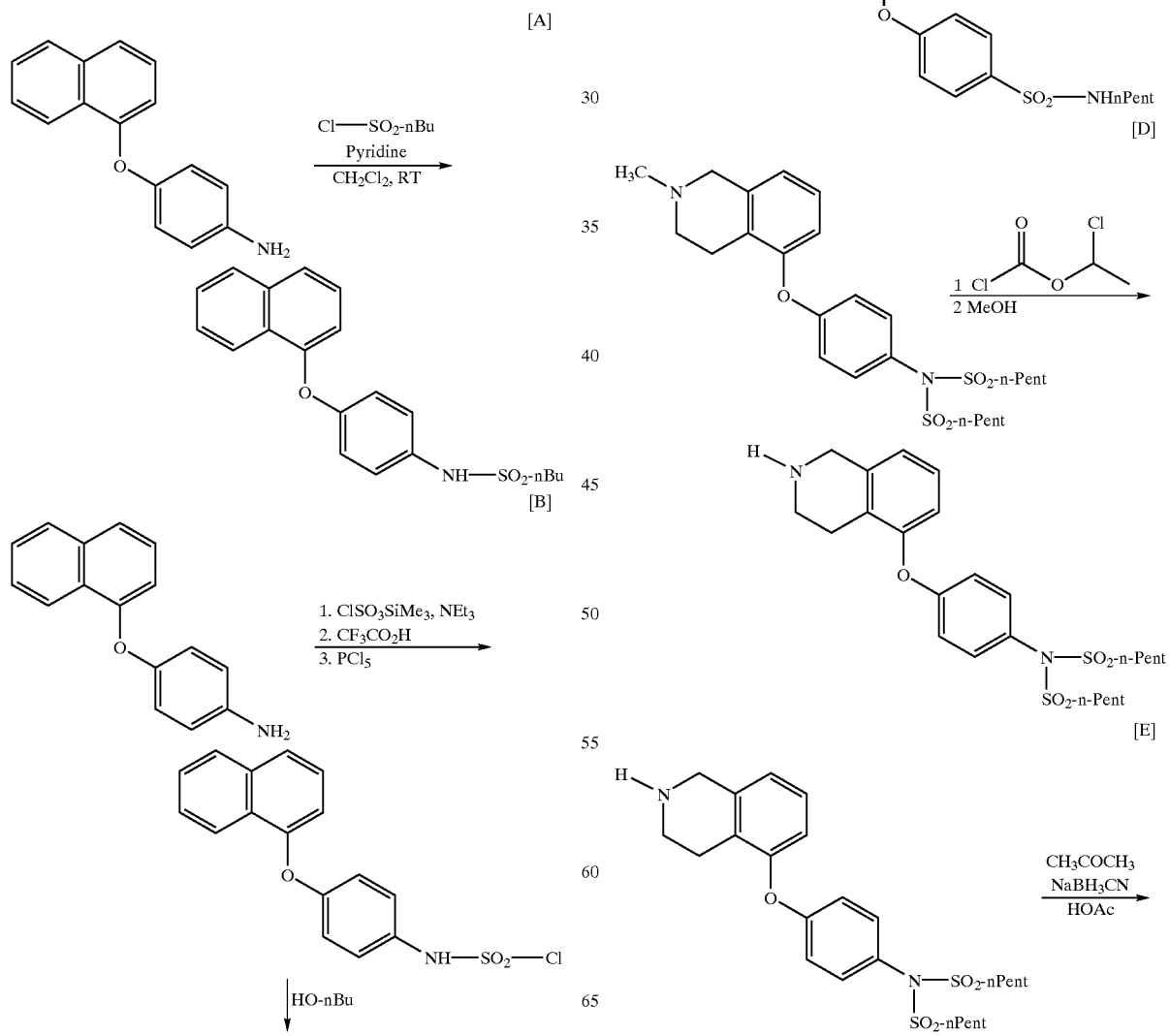

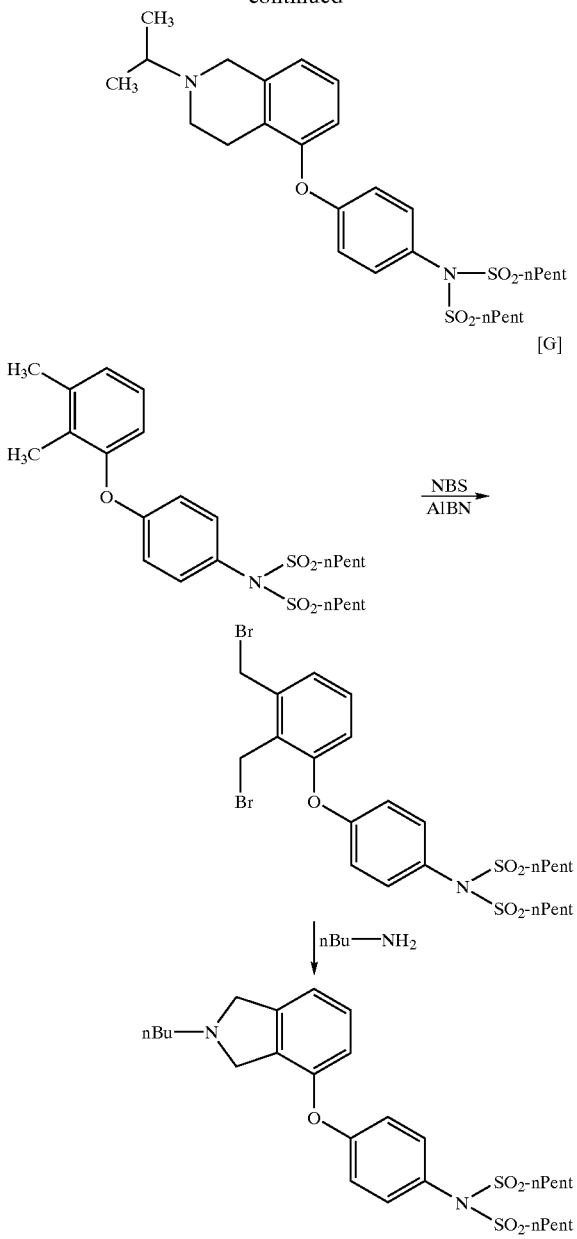

earth metal hydroxides such as, for example, sodium hydroxide, potassium hydroxide or barium hydroxide, or alkali metal carbonates such as sodium or potassium carbonate or sodium hydrogen-carbonate, or alkali metal alkoxides such as sodium methoxide, sodium ethoxide, potassium methoxide, potassium ethoxide or potassium tert-butoxide. Potassium carbonate and sodium hydroxide are particularly preferred.

In one variant, the reaction is carried out in pyridine to which a catalytic amount of DMAP is added. If appropriate, toluene can additionally be added.

In general, the processes are carried out at normal pressure. However, it is also possible to carry out the processes at elevated pressure or at reduced pressure (e.g. in a range from 0.5 to 5 bar).

The present invention additionally relates to compounds of the general formula (II)

in which $R^1$, A, D, E, G and M have the meanings indicated above.
Preferred compounds of the general formula (II) are those in which $R^1$ represents naphth-1-yl, optionally substituted by $(C_1-C_6)$-alkyl substituted by hydroxyl, $(C_1-C_6)$-acylamino, amino or $(C_1-C_6)$-alkoxy, indan-4-yl, substituted by hydroxy$(C_1-C_6)$-alkyl, a radical of the formula

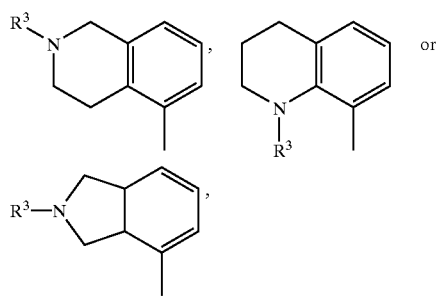

in which $R^3$ is $(C_1-C_6)$-alkyl,

E and A represent a bond,

D represents an oxygen atom,

G represents 1,3-phenylene, 1,4-phenylene or 2,5-pyridylene, each of which is optionally substituted by halogen, L represents a radical of the formula —NH—SO$_2$— or —O—SO$_2$—, $R^2$ represents $(C_1-C_6)$-alkyl which is optionally substituted by chlorine, trifluoromethyl, by a radical of the formula —O—CH$_2$—CF$_3$ or by phenyl or by pyridyl, which for their part can be substituted by bromine or chlorine, and M represents oxygen or —N($R^{32}$)—, in which $R^{32}$ is hydrogen or $(C_1-C_4)$-alkyl.

The compounds of the general formula (II) can be prepared, for example, by a process in which

[A] compounds of the general formula (VI)

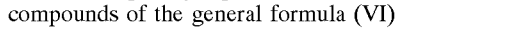

in which $R^1$, A and D' have the meaning indicated above, are reacted with compounds of the general formula (XI)

Suitable solvents are ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane is preferred.

In general, suitable bases are alkali metal hydrides or alkoxides, such as, for example, sodium hydride or potassium tert-butoxide, or cyclic amines, such as, for example, piperidine, pyridine, dimethylaminopyridine or $C_1$-$C_4$-alkylamines, such as, for example, triethylamine. Triethylamine, sodium hydride, pyridine and/or dimethylaminopyridine are preferred.

Suitable bases are additionally customary inorganic bases. These preferably include alkali metal hydroxides or alkaline in which E and G have the meaning indicated above, and $R^{44}$ is a leaving group, preferably halogen, in inert solvents, if appropriate in the presence of a base, and then reacted with customary reducing agents, preferably $H_2$/Pd/C in an inert solvent or with hydrazine hydrate, Pd/C, if appropriate with simultaneous hydrogenation of (C—C) multiple bonds, to give compounds of the general formula (IIa)

$$R^1\text{—}A\text{—}D'\text{—}E\text{—}G\text{—}NH_2 \qquad (IIa)$$

in which $R^1$, A, D', E and G have the meaning indicated above, or

[B] compounds of the general formula (IIb)

$$R^1\text{—}A\text{—}D\text{—}E\text{—}G\text{—}NH_2 \qquad (IIb)$$

in which $R^1$, A, D, E and G have the meaning indicated in claim 1, are reacted with a nitrosating agent, preferably an aqueous solution of sulphuric acid and sodium nitrite, and with subsequent warming, preferably to 60 to 100° C., to give compounds of the general formula (IIc)

$$R^1\text{—}A\text{—}D\text{—}E\text{—}G\text{—}OH \qquad (IIc)$$

in which $R^1$, A, D, E and G have the abovementioned meaning, or

[C] compounds of the general formula (XII)

$$R^1\text{—}R^{36} \qquad (XII)$$

in which $R^1$ has the meaning indicated above and $R^{36}$ represents a leaving group, preferably halogen, particularly preferably bromine, are reacted with compounds of the general formula (XIII)

$$HO\text{—}G\text{—}O\text{—}R^{45} \qquad (XIII)$$

in which

G has the meaning indicated above and $R^{45}$ represents ($C_1$–$C_6$)-alkyl, preferably methyl, in an inert solvent, preferably dimethylformamide or pyridine, if appropriate in the presence of a base, preferably potassium carbonate, and if appropriate in the presence of copper(I/II) salts, preferably copper(II) oxide or copper(I) iodide, in a temperature range from 0° C. to 200° C., preferably 80 to 150° C. and normal pressure, to give compounds of the general formula (Ik)

$$R^1\text{—}O\text{—}G\text{—}O\text{—}R^{45} \qquad (Ik)$$

in which $R^1$, G and $R^{45}$ have the abovementioned meaning, and are then reacted in the presence of an acid, preferably hydrobromic acid, to give compounds of the general formula (IId)

$$R^1\text{—}O\text{—}G\text{—}OH \qquad (IId)$$

or

[D] compounds of the general formula (VI)

$$R^1\text{—}A\text{—}D'\text{—}H \qquad (VI)$$

in which $R^1$, A and D' have the meaning indicated above, are reacted with compounds of the general formula (XIV)

$$R^{46}\text{—}E\text{—}G'\text{—}R^{47} \qquad (XIV)$$

in which $R^{46}$ has the meaning indicated for $R^{36}$ and is identical to or different from this, E has the abovementioned meaning, G' represents a doubly bonded 5- to 7-membered aromatic heterocycle having up to 3 heteroatoms from the group consisting of sulphur, nitrogen and/or oxygen, which can optionally be substituted by one or more, identical or different substituents as defined for G as indicated above, and $R^{47}$ represents halogen, preferably chlorine or bromine, to give a compound of the general formula (XV)

$$R^1\text{—}A\text{—}D'\text{—}E\text{—}G'\text{—}R^{47} \qquad (XV)$$

in which $R^1$, A, D', E, G' and $R^{47}$ have the abovementioned meaning, in inert solvents, if appropriate in the presence of a base, and are then transformed with potassium amide in liquid ammonia into the corresponding free amines of the general formula (IIe)

$$R^1\text{—}A\text{—}D'\text{—}E\text{—}G'\text{—}NH_2 \qquad (IIe)$$

in which $R^1$, A, D', E and G' have the abovementioned meaning.

DOS (German Offenlegungsschrift) 1 942 264 describes the preparation of fluorinated alkanesulphonyl chlorides, U.S. Pat. No. 5,149,357, inter alia, the preparation of a 4,4,4-trifluorobutanesulphonamide, but without disclosing the preparation of the corresponding sulphonamide.

The fluorinated sulphonyl chlorides were prepared analogueously to DOS (German) 1 942 264.

The present invention likewise relates to compounds of the general formula (XV)

$$R^{48}\text{—}SO_2\text{—}(CH_2)_h\text{—}U\text{—}(CH_2)_i\text{—}CR^{49}R^{50}\text{—}CF_2\text{—}R^{51} \qquad (XV)$$

in which $R^{48}$ is a leaving group,

U is oxygen or a single bond, $R^{49}$ and $R^{50}$ are identical or different and denote H, F, Cl or $CF_3$, $R^{51}$ is H, F, Cl or Br, h is a number 1 or 2 and i is a number 0 or 1, with the exception of the compounds in which U is a single bond, $R^{49}$ and $R^{50}$ are identical and denote H or F and $R^{51}$ denotes F, and with the exception of the compounds in which U is oxygen, $R^{49}$ or $R^{50}$ denotes Cl and i denotes 0.

The present invention additionally relates to compounds of the general formulae (XVI) and (XVII)

$$R^{48}\text{—}SO_2\text{—}CH_2\text{—}CH_2\text{—}CH_2\text{—}CF_3 \qquad (XVI)$$

or $$R^{48}\text{—}SO_2\text{—}CH_2\text{—}CH_2\text{—}CH_2\text{—}CF_2\text{—}CF_3 \qquad (XVII)$$

in which
    $R^{48}$ is a leaving group.
    Compounds in which $R^{48}$ is chlorine are preferred.
    Suitable solvents are ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane is preferred.

In general, suitable bases are alkali metal hydrides or alkoxides, such as, for example, sodium hydride or potassium tert-butoxide, or cyclic amines, such as, for example, piperidine, pyridine, dimethylaminopyridine or $C_1$–$C_4$-alkylamines, such as, for example, triethylamine. Sodium hydride, pyridine and/or dimethylaminopyridine are preferred.

Suitable bases are additionally the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate, or sodium hydrogen-carbonate, or alkali metal alkoxides such as sodium methoxide, sodium ethoxide, potassium methoxide, potassium ethoxide or potassium tert-butoxide Potassium carbonate and sodium hydroxide are particularly preferred.

The bases are employed in an amount from 1–20 equivalents, preferably from 2 to 10 equivalents, in each case based on 1 equivalent of the compounds of the general formulae (X) and (XII)

The processes are in general carried out at normal pressure However, it is also possible to carry out the processes at elevated pressure or at reduced pressure (e.g. in a range from 0.5 to 5 bar)

The processes are in general carried out in a temperature range from 0° C. to 200°, preferably from room temperature to 140° C.

The compounds of the general formulae (III), (V), (VIII), (IX), (X) and (XII) are known per se or can be prepared by customary methods.

Alkylation for the preparation of the ammonium compounds is in general carried out using alkylating agents such as, for example, alkyl halides, sulphonic acid esters or substituted or unsubstituted dialkyl or diaryl sulphates, preferably using methyl iodide or dimethyl sulphate.

Alkylation is in general carried out in one of the above-mentioned solvents, preferably in dimethylformamide in a temperature range from 0° C. to +70° C., preferably from 0° C. to +30° C. and normal pressure.

Surprisingly, the new aryl sulphonamides and their analogues show an unforeseeable, useful spectrum of pharmacological action.

They are distinguished as highly effective agonists of the CB1 receptor and in some cases of the CB2 receptor. They can be employed alone or in combination with other medicaments for the treatment and/or prevention of neuronal damage of varying cause, such as, for example, due to ischaemic, thrombic and/or thromboembolic, and haemorrhagic stroke, and conditions after direct and indirect injuries in the area of the brain and of the skull, furthermore for the treatment and/or prevention of cerebral ischaemia after all operative interventions in the brain or peripheral organs or body parts and conditions of pathogenic or allergic nature accompanying or preceding them, which can lead primarily and/or secondarily to neuronal damage. Likewise, the compounds according to the invention are also suitable for the therapy of primary and/or secondary pathogenic conditions of the brain, for example during or after cerebral vasospasms, hypoxia and/or anoxia of previously unmentioned origin, perinatal asphyxia, autoimmune disorders, metabolic and organ disorders which can be accompanied by damage to the brain and also damage to the brain as a result of primary brain disorders, for example convulsive conditions and athero- and/or arteriosclerotic changes, for the treatment of chronic or psychiatric conditions such as, for example, depression, neurodegenerative disorders such as, for example, Alzheimer's, Parkinson's or Huntington's disease, multiple sclerosis, amyotrophic lateral sclerosis, neurodegeneration due to acute and/or chronic viral or bacterial infections and multiinfarct dementia.

They can moreover be employed in medicaments for the treatment of states of pain, emesis, nausea, glaucoma, asthma, anorexia, convulsions, rheumatism, sedation and mobility disorders.

The substances according to the invention are also suitable for the treatment of disorders which are caused by bacterial and/or viral infections which are based on direct and/or indirect alterations of the immune system or on dysregulations with participation of the immune system, such as, for example, in local or systemic autoimmune diseases (e.g. lupus erythematosus in all its variants), inflammatory and/or autoimmunologically related diseases of the joints (e.g. primary chronic polyarthritis, trauma-related inflammation), inflammatory and/or autoimmunologically related diseases of the bone and muscle apparatus, inflammatory and/or autoimmunologically related pathogenic processes of the internal organs (e.g. Crohn's disease, glomerulonephritis) and of the external organs (e.g. allergic reactions due to aerogenic intake of antigens) and of the central nervous system (e.g. multiple sclerosis, Alzheimer's disease, psychiatric disorders) as well as of the sense organs, primary and/or secondary and/or autoimmunological disorders of the haematogenic system and of the immune system (e.g. rejection reactions, AIDS) themselves, and also in skin disorders of inflammatory and/or immunological origin in humans and animals These substances furthermore act on the indirect symptoms of these disorders such as, for example, pain.

Their use for the treatment of cerebral ischaemias and craniocerebral trauma is preferred.

CB1—Luciferase Reporter Gene Test
1. Cloning of the Rat Cannabinoid Receptor CB1
    Total RNA from rat brain (the tissue was taken from freshly killed animals and shock-frozen in liquid nitrogen) was isolated by acidic guanidinium thiocyanate/phenol/chloroform extraction (J. Biol. Chem. 1979, 18, 5294) and converted into cDNA by means of reverse transcriptase and random primers (in each case from Invitrogen). The polymerase chain reaction (PCR, conditions: 4 min 94° C., 1×; 1 min 94° C.; 2 min 53° C.; 1 min 72° C., 50 cycles; 1 min 94° C., 2 min 53° C., 4 min 72° C., 1×) was carried out in a Perkin Elmer thermocycler using the enzyme Taq polymerase (Perkin Elmer); the oligonucleotide primers employed (bases 99 to 122: 5'→3', "down"; 1556–1575: 3'←5', "up") were derived from the published sequence of the rat cannabinoid receptor (Nature 1990, 346, 561) and were synthesized on a DNA synthesizer, model 1380 from Applied Biosystems. One part of the PCR reaction was separated in a 1% strength agarose gel in 1× TBE buffer and then stained with ethidium bromide, only one band having the expected length being visible (approximately 1.5 kb). This PCR product was subcloned into the TA cloning vector (Invitrogen) and the nucleotide sequence of the inserts was determined by the dideoxynucleotide chain termination reaction using T7DNA polymerase (Sequenase, USA/ Amersham). The insert has a length of 1477 base pairs and contains an open reading frame of 1419 base pairs which corresponds to a protein of 473 amino acids. The number of base pairs, the position of the open reading frame and the number of amino acids agree with the published sequence. Computer analyses were carried out with the aid of the GCG software suite (Genetic Computer Group). The cDNA insert was subcloned into the expression vector pRc/CMV after partial digestion with HindIII and NotI (Biolabs). This construct (plasmid CMV-RH) was employed for transfection experiments.

2. Stable Transfection of the CHOluc9 Reporter Cells

CHOluc9 cells were cultured in 50% Dulbecco's modified Eagle medium/50% F-12 (DMEM/F12) which contained 10% foetal calf serum (FCS). Transfections were prepared in 6-well plates. 7.5 µg of Qiagen-purified CMV-RH plasmid DNA were added per 105 cells with the DOTAP transfection system, corresponding to the experimental protocol of the manufacturer (Boehringer Mannheim). Transfected cells were selected using 1 mg/ml G418 and individual clones were obtained by limiting dilution in 96-well plates. Cell lines which express the cannabinoid receptor were identified for the inhibition of reporter gene expression after incubation with the cannabinoid receptor agonist, WIN-55,212-2, in the presence of forskolin. Several stable transfected and subcloned cell lines were further characterized by means of RT-PCR, as described under 1.

3. Test Optimization and Pharmacological Characterization of the CHOCB1 Reporter Cell Line With the aim of high sensitivity and reproducibility, low variance and high suitability for carrying out on the robotic system, the luciferase test was optimized by variation of several test parameters, such as, for example, cell density, duration of the growth phase and the test incubation, forskolin concentration, medium composition. The following test protocol was used for pharmacological characterization of the cells and for robot-assisted substance screening: the stock cultures were cultured in 50% Dulbecco's modified Eagle medium/50% F-12 (DMEM/F12) with 10% FCS at 37° C. under 10% $CO_2$ and in each case split 1:10 after 2 to 3 days. Test cultures were inoculated into 96-well plates at 5000 cells per well and cultured at 37° C. for 70 hours. The cultures were then carefully washed with phosphate-buffered saline and reconstituted using serum-free ultra-CHO medium (Bio-Whittaker). The substances dissolved in DMSO were diluted 1× in medium and pipetted into the test cultures (maximum DMSO final concentration in the test batch: 0.5%). 20 minutes later, forskolin was added and the cultures were then incubated at 37° C. in an incubator for 3 hours. The supernatants were then removed and the cells were lysed by addition of 25 µl of lysis reagent (25 mM triphosphate, pH 7.8 with 2 mM DTT, 10% glycerol, 3% Triton X100) Directly after this, luciferase substrate solution (2.5 mM ATP, 0.5 mM luciferin, 0.1 mM coenzyme A, 10 mM tricine, 1.35 mM $MgSO_4$, 15 mM DTT, pH 7.8) was added, the mixture was briefly shaken and the luciferase activity was measured using a Hamamatzu camera system For inactivation of $G_i$ proteins, the test cultures were treated with 5 mg/ml (final conc.) of Pertussis toxin for 16 hours before the test The $IC_{50}$ values were calculated using the GraphPad-Prism™ program (Hill equation, specific: one-site competition).

Activity in the rat CB1 receptor luciferase receptor gene test

| Example | $IC_{50}$ (nmol/l) |
|---------|---------------------|
| 1       | 15                  |
| 33      | 10                  |
| 51      | 0.9                 |
| 65      | 13                  |
| 99      | 2.9                 | hCB2—Luciferase Reporter Gene Test

CHOluc9 cells were stably transfected using the human CB2 receptor. Transfection, clone selection and test development were carried out analogueously to the studies using the rat CB1 receptor. The following test protocol was used for the pharmacological characterization of the cells and for substance testing:

The stock cultures were cultured in 50% Dulbecco's modified Eagle medium/50% F-12 (DMEM/F12) with 10% FCS at 37° C. under 10% $CO_2$ and in each case split 1:10 after 2 to 3 days. Test cultures were inoculated into 96-well plates at 5000 cells per well in DMEM/F12 medium with 5% FCS and cultured at 37° C. for 70 hours The medium was then removed from the cultures and replaced by serum-free ultra-CHO medium (Bio-Whittaker). The substances dissolved in DMSO (200× final concentration) were pipetted into the test cultures (maximum DMSO final conc. in the test mixture 0.5%) and 20 min later forskolin was added The cultures were then incubated at 37° C. in an incubator for 3.5 hours The supernatants were then removed and the cells were lysed by addition of 25 µl of lysis reagent (25 mM triphosphate, pH 7.8 with 2 mM DTT, 10% glycerol, 3% Triton X100). Directly following, 50 µl of luciferase substrate solution, double-concentrated (5 mM ATP, 1 mM luciferin, 0.2 mM coenzyme A, 10 mM tricine, 1.35 mM $MgSO_4$, 15 mM DTT, pH 7.8) were added, the mixture was briefly shaken, and the luciferase activity was determined using a photomultiplier camera measuring system (Hamamatzu)

The $IC_{50}$ values were calculated using the GraphPad-Prism™ program (Hill equation; specific one-site competition).

Binding Studies on Rat Cortex Membranes

Membrane protein is prepared from different tissues or from cells by standard methods. Buffer, labelled ligand, DMSO or test substance are pipetted together, then 100 µg of protein are added, and the mixture is well mixed and incubated in a water bath at 30° C. for 60 min. After expiry of the incubation time, the reaction is stopped by addition of ice-cold incubation buffer to each tube. After filtering off, washing is carried out with ¾ ml of incubation buffer. The filters are transferred to minivials and the radioactivity is determined in a scintillation counter. Affinity for the CB1 receptor (rat cortex membranes)

| Example | $K_i$ (nmol/l) |
|---------|----------------|
| 1       | 590            |
| 33      | 420            |
| 51      | 41             |
| 65      | 250            |

Inhibition of Glutamate Release

After decapitation of a rat, the skull is opened, and the brain is lifted out and cut along the median fissure. The hippocampus is exposed, separated from the remaining tissue, cut into 350 μm thick sections and incubated at 37° C. in straining vessels for 60 min Followed by basal value and stimulation 1 with 75 mM KCl (S1), the sections are incubated with test substance and then stimulation is repeated with KCl and test substance (S2). Glutamate concentration of the samples to be investigated is then measured by means of an enzymatic action (GLDH) and fluorometric measurement of NADH. By means of a calibration curve, the glutamate content of the sample is determined, and with knowledge of the protein content the glutamate content/mg of protein can be calculated The ratio S2/S1 is compared; glutamate release inhibitors reduce this ratio in a concentration-dependent manner.

Hypothermia

1. Agonism Testing:

Five minutes after determination of the basal body temperature via an oesophageal temperature probe, the test substance is administered (i.v.). A control group receives only the solvent for the test substances, likewise i.v. The body temperature is measured 7.5, 15, 30 and 60 minutes after i.v. administration. The group size per dose is 5–7 animals (rats).

Rat hypothermia—Agonism testing

| Example | $ED_{-1° C.}$ [a)] [mg/kg] |
|---|---|
| 1 | 1.0 [b)] |
| 33 | 0.6 [b)] |
| 51 | 0.1 [b)] |
| 65 | 1.0 [b)] |
| 99 | 0.6 [b)] |

[a)] Effective dose for 1° C. body temperature reduction
[b)] Hypothermia is significantly reduced by administration of the specific CB1 antagonist SR 141716 A (see "Antagonism testing" method)

2. Antagonism Testing:

The specific CB1 antagonist SR 141716A or, to the control group, only the solvent (Solutol/0.9% NaCl), is administered intraperitoneally 60 minutes before administration of test substance. The basal body temperature is measured five minutes before administration of SR 141716A via oesophageal temperature probe The further procedure corresponds to the "agonism testing" method The group size per dose is 5–7 animals (rats).

Permanent Focal Cerebral Ischaemia in the Rat (MCA-O)

Under isoflurane anaesthesia, the median cerebral artery is exposed on one side and the latter and its side branches are irreversibly sealed by means of electrocoagulation. As a result of the intervention a cerebral infarct is formed. During the operation, the body temperature of the animal is kept at 37° C. After wound closure and wearing off of the anaesthesia, the animals are again released into their cage. The administration of substance is carried out according to different time schemes and via different administration routes (i.v., i.p.) after occlusion. The infarct size is determined after 7 days. To do this, the brain is removed, worked up histologically and the infarct volume is determined with the aid of a computer-assisted analysis system.

Activity in the model of permanent focal cerebral ischaemia (MCA-O)

| Example | % Reduction in the infarct volume | Dose |
|---|---|---|
| 1 | 35 | 0.03 mg/kg/h [b)] |
| 33 | 33 | 0.1 mg/kg [a)] |
| 51 | 24 | 0.1 mg/kg [a)] |
| 65 | 37 | 0.03 mg/kg/h [b)] |
|  | (47) | (0.01 mg/kg/h) |

[a)] Substance administration as intravenous bolus injections in each case directly, 2 and 4 hours after occlusion
[b)] Substance administration as an intravenous, continuous infusion directly up to 4 hours after occlusion Subdural Haematoma in the Rat (SDH)

Under anaesthesia, the animal's own blood is injected subdurally on one side An infarct is formed under the haematoma. Substance administration is carried out according to different time schemes and via different administration routes (i.v., i.p.) The determination of the infarct size is carried out as described in the model of permanent focal ischaemia in the rat (MCA-O)

Activity in the model "subdural haematoma in the rat (SDH)"

| Example | % Reduction in the infarct volume | Dose |
|---|---|---|
| 1 | 54 | 0.1 mg/kg [a)] |
|  | (84) | (1.0 mg/kg [a)]) |
| 33 | 42 | 0.1 mg/kg [a)] |
| 51 | 54 | 0.01 mg/kg/h [b)] |
| 65 | 53 | 0.1 mg/kg [a)] |
|  | (65) | (0.3 mg/kg/h [b)]) |

[a)] Substance administration as intravenous bolus injections in each case directly, 2 and 4 hours after occlusion
[b)] Substance administration as an intravenous, continuous infusion directly up to 4 hours post-trauma The new active compounds can be converted in a known manner into the customary formulations, such as tablets, coated tablets, pills, granules, aerosols, syrups, emulsions, suspensions and solutions, using inert non-toxic, pharmaceutically suitable excipients or solvents. In this case the therapeutically active compound should in each case be present in a concentration from approximately 0.5 to 90% by weight of the total mixture, i.e. in amounts which are sufficient in order to achieve the dosage range indicated.

The formulations are prepared, for example, by extending the active compound using solvents and/or excipients, if appropriate using emulsifiers and/or dispersants, it optionally being possible, for example, to use organic solvents as auxiliary solvents if water is used as a diluent.

Administration is carried out in a customary manner, preferably orally, transdermally or parenterally, in particular perlingually or intravenously.

In general, it has proved advantageous in the case of intravenous administration to administer amounts from approximately 0.01 to 10 mg/kg, preferably approximately 0.1 to 10 mg/kg, of body weight to achieve effective results.

In spite of this, if appropriate it may be necessary to depart from the amounts mentioned, namely depending on the body weight or on the type of administration route, on individual behaviour towards the medicament, the manner of its formulation and the time or interval at which administration takes place. Thus in some cases it may be adequate to manage with less than the abovementioned minimum amounts, while in other cases the upper limit mentioned has to be exceeded. In the case of the administration of relatively large amounts, it may be advisable to divide these into several individual doses over the course of the day.

| Abbreviations used | |
|---|---|
| Me | = CH$_3$ |
| Et | = C$_2$H$_5$ |
| nPr | = n-(CH$_2$)$_2$CH$_3$ |
| nBu | - n-(CH$_2$)$_3$CH$_3$ |
| nPent | = n-(CH$_2$)$_4$CH$_3$ |
| nHex | = n-(CH$_2$)$_5$CH$_3$ |
| nOct | = n-(CH$_2$)$_7$CH$_3$ |
| PE | = Petroleum ether |
| Tol | = Toluene |
| EA | = Ethyl acetate |
| Et$_2$O | = Diethyl ether |

| Solvents | |
|---|---|
| I | PE:Et$_2$O 10:1 |
| II | PE:Et$_2$O 5:1 |
| III | PE:Dichloromethane 5:1 |
| IV | Tol:EA 10:1 |
| V | Cyclohexane:Dichloromethane 5:1 |
| VI | Tol:EA 5:1 |
| VII | Tol:EA 1:1 |
| VIII | Tol:EA 5:3 |
| IX | PE:Dichloromethane 1:1 |
| X | Tol:EA 20:1 |
| XI | PE:EA 5:1 |
| XII | Tol:EA 8:1 |
| XIII | EA:Acetone 20:1 |
| XIV | PE:EA 10:1 |
| XV | Dichloromethane:Formic acid 40:1 |
| XVI | Tol:EA 3.1 |
| XVII | Dichloromethane:Et$_2$O 10:1 |
| XVIII | Tol:EA 1:2 |
| XIX | EA.Acetone 20:3 |
| XX | EA.Acetone 10:1 |
| XXI | Dichloromethane:Formic acid 10:1 |
| XXII | Tol.EA:Formic acid 10:1:0.05 |
| XXIII | Dichloromethane:Methanol.Conc. NH$_3$ 10:1:0.5 |
| XXIV | Dichloromethane:Ethanol 20:1 |
| XXV | Dichloromethane:Methanol 10:1 |
| XXVI | Dichloromethane:Methanol 5:1 |
| XXVII | Tol:EA 2:1 |
| XXVIII | Hexane.EA 4:1 |
| XXIX | Tol:EA 15:1 |
| XXX | Toluene |
| XXXI | Toluene:EA 30:1 |
| XXXII | Dichloromethane:Methanol 19:1 |
| XXXIII | Dichloromethane:Methanol 9:1 |
| XXXIV | Dichloromethane:Methanol 4:1 |
| XXXV | Ethyl acetate |
| XXXVI | Cyclohexane:Ethyl acetate 3:1 |
| XXXVII | Cyclohexane:Ethyl acetate:Methanol 10:2:1 |
| XXXVIII | n-Hexane:Ethyl acetate 2:1 |
| XXXIX | Dichloromethane:Methanol 3:1 |
| XL | Ethyl acetate:Methanol 4:1 |
| XLI | Dichloromethane:Methanol 95:5 |
| XLII | EA:Isooctane 1:1 |
| XLIII | EA:Cyclohexane 8:2 |
| XLIV | EA:Cyclohexane 3:7 |
| XLV | Dichloromethane:Methanol:Triethylamine 9:1:0.1 |
| XLVI | Dichloromethane:Methanol 98:2 |

| Mass spectroscopy methods | |
|---|---|
| A | EI |
| B | DCI, NH$_3$ |
| C | ESI |
| D | FAB |
| E | DCI, isobutane |

STARTING COMPOUNDS

EXAMPLE 1 A

A solution of 1-naphthol (102 g; 0.709 mol) in DMF (800 ml) is treated with K$_2$CO$_3$ (97.9 g; 0.709 mol) and stirred at RT for 2 h. After dropwise addition of a solution of 4-fluoro-1-nitrobenzene (100 g; 0.709 mol) in DMF (200 ml), the reaction mixture is stirred overnight at RT. The solvent is then distilled off in vacuo and the residue is treated with ethyl acetate (600 ml). After filtration, the largest part of the solvent is distilled off in vacuo. Precipitated product is filtered off, washed with a little ethyl acetate and dried in vacuo.

Yield: 107 g

A further 25 g of product are additionally obtained by further evaporation of the mother liquor.

Total yield: 132 g (69% of theory)

M.p.: 143° C.

MS (EI): m/e 265 (M)

The compounds shown in Table I are prepared in analogy to Example 1 A.

TABLE 1
R¹—D—G—NO₂
| Ex. No. | R¹ | D | G | Yield (% of theory) | M.P. (° C.) | R_f | MS (m/e) |
|---|---|---|---|---|---|---|---|
| 2A | 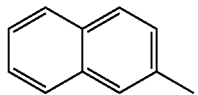 | O | 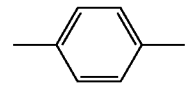 | 53 | 102–3 | 0.59 (I) | 283 (M + NH₄) (B) |
| 3A | 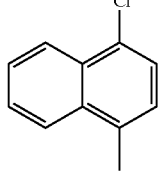 | O | 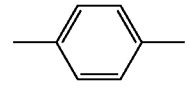 | 67 | 82–83 | 0.56 (I) | 317 (M + NH₄) (B) |
| 4A | 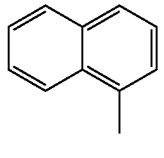 | O | 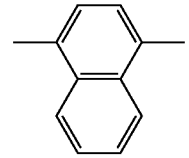 | 55 | 93–95 | 0.62 (II) | 333 (M + NH₄) (B) |
| 5A | 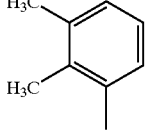 | O | 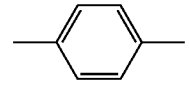 | 30 | 77 | 0.17 (III) | 261 (M + NH₄) (B) |
| 6A | 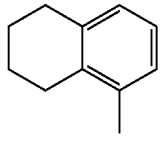 | O | 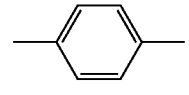 | 37 | 81 | 0.21 (III) | 287 (M + NH₄) (B) |
| 7A | 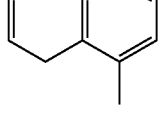 | O | 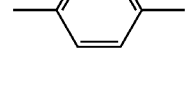 | 82 | 60–62 | 0.85 (IV) | 285 (M + NH₄) (B) |
| 8A | 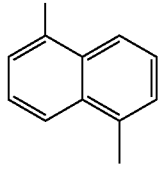 | O | 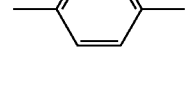 | 92 | 80–81 | 0.89 (V) | 383 (M + NH₄) (B) |
| 9A | 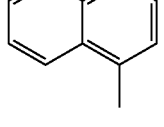 | O | 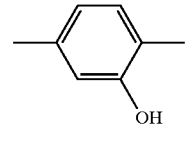 | 11 | 94 | 0.15 (V) | 299 (M + NH₄) (B) |
| 10A | 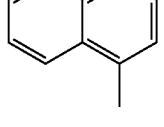 | O | 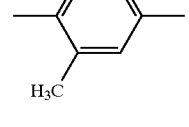 | 86 | — | 0.23 (V) | 297 (M + NH₄) (B) |

TABLE 1-continued
R¹—D—G—NO₂
| Ex. No. | R¹ | D | G | Yield (% of theory) | M.P. (° C.) | R_f | MS (m/e) |
|---|---|---|---|---|---|---|---|
| 11A | 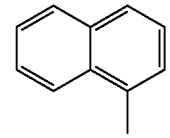 | O | 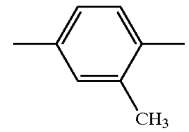 | 58 | 73 | 0.19 (V) | 297 (M + NH₄) (B) |
| 12A | 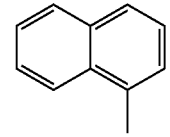 | O | 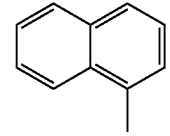 a) | 77 | 89 | 0.7 (VI) | 267 (M + NH₄) (B) |
| 13A | 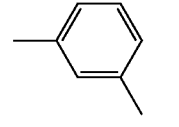 | O | 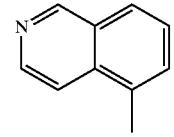 | 26 | — | 0.90 (IV) | 283 (M + NH₄) (B) |
| 14A | 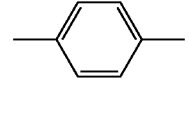 | O | 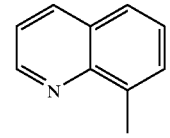 | 72 | 96–98 | 0.43 (VII) | 267 (M + NH₄) (B) |
| 15A | 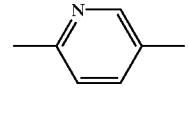 | O | 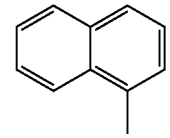 | 93 | 132–3 | 0.54 (VIII) | 268 (M + H) (B) |
| 16A | 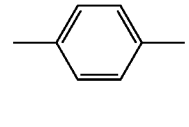 | S^c) | 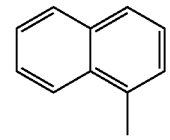 | 64 | 83 | 0.51 (IX) | 299 (M + NH₄) (B) |
| 17A | 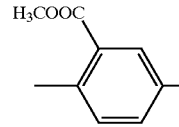 | O | 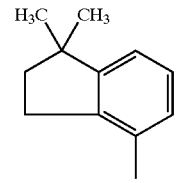 | 90 | 144 | 0.72 (IV) | 341 (M + NH₄) (B) |
| 18A | 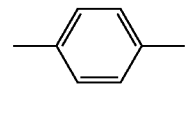 | O | 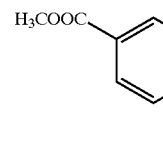 | 55 | 70 | 0.86 (IV) | 301 (M + NH₄) (B) |
| 19A^f) | 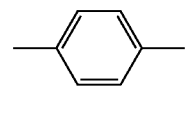 | O |  | 76 | 125–6 | 0.80 (VI) | 311 (M + NH₄) (B) |

TABLE 1-continued

R¹—D—G—NO₂

| Ex. No. | R¹ | D | G | Yield (% of theory) | M.P. (° C.) | $R_f$ | MS (m/e) |
|---|---|---|---|---|---|---|---|
| 20A | 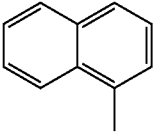 | O | 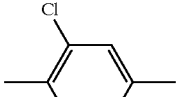 | 95 | 86 | 0.30 (III) | 317 (M + NH₄) (B) |
| 21A[d)] | 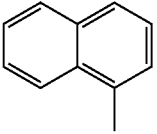 | NH | 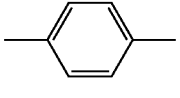 | 72 | 169–71 | 0.58 (VI) | 282 (M + NH₄) (B) |
| 22A | 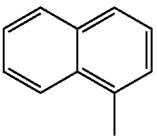 | O | 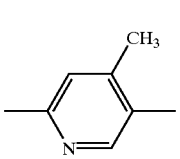 e) | 80 | 68 | 0.76 (X) | 281 (M + H) (B) |
| 23A | 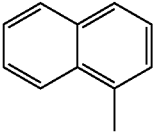 | O | 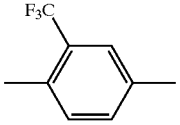 | 98 | — | 0.89 (IV) | 351 (M + NH₄) (B) |
| 24A | 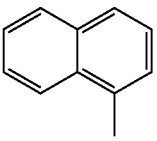 | O | 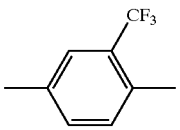 | 95 | 106–8 | 0.89 (V) | 351 (M + NH₄) (B) |

[a)]Starting material:

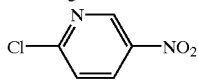

[b)]Reaction at 140° C.
[c)]Starting material 1-thionaphthol
[d)]Reaction of 1-aminonaphthalene and 4-fluoro-1-nitrobenzene analogously to J. Chem. Soc. Perkin Trans I, 1988, 1331
[e)]Starting material:

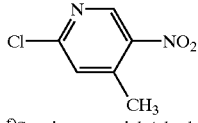

[f)]Starting material 1-hydroxy-6-methoxycarbonylnaphthalene, prepared according to J. Chem. Soc. 1923, 123, 1649 and subsequent esterification

EXAMPLE 25 A 1-(Naphthyl-1-methyloxy)-4-nitrobenzene

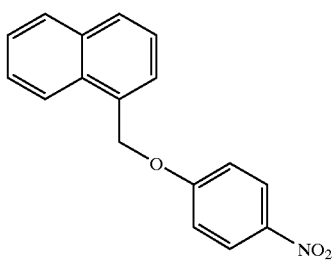

A solution of 4-nitrophenol (15.7 g; 113 mmol) in DMF (300 ml) is treated with K₂CO₃ (30.8 g; 223 mmol) and stirred at RT for 1 h. After addition of 1-naphthylmethyl bromide (25.0 g; 113 mmol), the reaction mixture is stirred at 50° C. overnight. The solvent is distilled off in vacuo and the residue is taken up using ethyl acetate (600 ml) and water (250 ml). After filtration, the phases are separated and the aqueous phase is extracted with ethyl acetate (3×300 ml). The combined organic phases are washed with water (200 ml), dried over MgSO₄ and largely concentrated in vacuo. Precipitated crude product is filtered off with suction, stirred in ethyl acetate/petroleum ether, filtered off with suction again and dried. The product is purified by recrystallization from CH₂Cl₂/methanol.

Yield: 15.7 g (50% of theory)
M.p.: 145–146° C.
MS (DCI, NH₃): m/e=297 (M+NH₄)
$R_f$=0.83 (IV).

The examples shown in Table II are prepared in analogy to the procedure of Example 25 A.

TABLE II

R¹—(CH₂)ₙ—O—(CH₂)ₘ—G

| Ex. No. | R¹ | n | m | G | Yield (% of theory) | M.p. (° C.) | $R_f$ | MS (m/e) |
|---|---|---|---|---|---|---|---|---|
| 26A | 2-naphthyl | 1 | 0 | 4-NO₂-phenyl | 93 | 151–2 | 0.86 (X) | 297 (M + NH₄) (B) |
| 27AI | 1-naphthyl | 0 | 1 | 4-NO₂-phenyl | 29 | 137–9 | 0.70 (IV) | 297 (M + NH₄) (B) |
| 28A | 1-naphthyl | 0 | 1 | 3-NO₂-phenyl | 82 | 68–72 | 0.82 (IV) | 297 (M + NH₄) (B) |

Reduction of the Nitro Groups of Examples 1 A-29 A

Method A

EXAMPLE 29 A

1-Amino-4-(2,3-dimethylphenyl-1-oxy)benzene

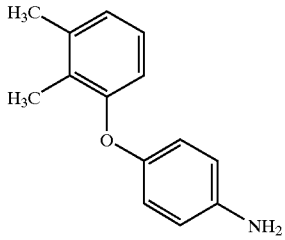

A suspension of Example 5 A (13.5 g; 55.6 mmol) and 10% palladium on active carbon (1.45 g) in methanol (132 ml) is heated to reflux under argon. After dropwise addition of hydrazine hydrate (5.4 ml, 111 mmol), the mixture is stirred under reflux for a further 2 h. The reaction mixture is filtered through kieselgur, washed with methanol and then concentrated in vacuo. The residue is chromatographed on silica gel using toluene: ethyl acetate (10:1).

Yield: 0.33 (IV)

MS (DCI, NH₃): m/e=231 (M+NH₄)

Method B

EXAMPLE 30 A n-Butyl 5-(4-aminophenyl-1-oxy)naphthalene-1-carboxylate

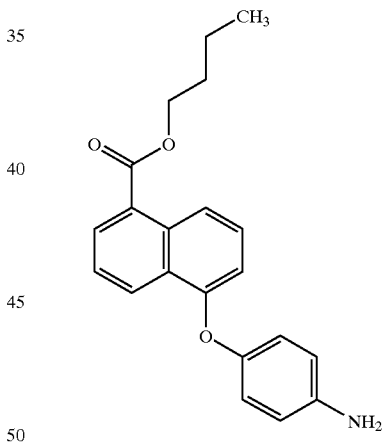

A solution of Example 8 A (10.96 g; 30.0 mmol) in THF (100 ml) is treated with 10% palladium on active carbon (0.25 g) and hydrogenated at normal pressure for 5 h. The reaction mixture is filtered through silica gel, washed with THF and concentrated in vacuo. The residue is stirred in diethyl ether, filtered off and dried in vacuo.

Yield: 8.38 g (83% of theory)

M.p.: 104–105° C.

$R_f$=0.31 (IV)

MS (ESI): m/e=336 (M+H)

Method C

EXAMPLE 31 A

1-Amino-4-(5,8-dihydro-naphthyl-1-oxy)benzene

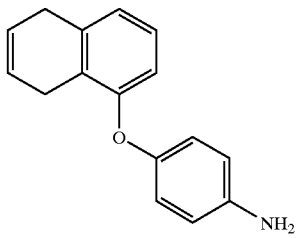

A 15% strength solution of titanium(III) chloride in 10% hydrochloric acid (212 ml, 243 mmol) is added dropwise to a solution of the compound from Example 7 A (10.7 g; 40.0 mmol) in glacial acetic acid (380 ml) and water (80 ml) and the mixture is stirred overnight. The solvents are distilled off in vacuo and the residue is taken up in ethyl acetate/water. A pH of 9–10 is set by addition of 3 N sodium hydroxide solution and after phase separation the aqueous phase is extracted 3× with ethyl acetate. The combined organic phases are washed 2× with water, dried over $MgSO_4$ and concentrated in vacuo. The residue is chromatographed on silica gel using toluene/ethyl acetate (20:1).

Yield: 2.1 g (22% of theory)

$R_f$=0.25 (X)

MS (DCI, $NH_3$): m/e=238 (M+H)

The examples shown in Table III are prepared in analogy to Examples 29 A–31 A:

TABLE III $R^1$—$(CH_2)_n$—D—$(CH_2)_m$—G—$NH_2$

| Ex. No. | Method | $R^1$ | n | D | m | G | Yield (% of theory) | M.p. (° C.) | $R_f$ | MS (m/e) |
|---|---|---|---|---|---|---|---|---|---|---|
| 32A | A | 2-methylnaphthyl | 0 | O | 0 | 1,4-phenylene | 86 | 115–7 | 0.14 (II) | 253 (M + $NH_4$) (B) |
| 33A | A | 1-chloro-4-methylnaphthyl | 0 | O | 0 | 1,4-phenylene | 45 | — | 0.33 (IV) | 287 (M + $NH_4$) (B) |
| 34A | A | 1-methylnaphthyl | 0 | O | 0 | 1,4-naphthylene | 71 | 107–8 | 0.39 (IV) | 303 (M + $NH_4$) (B) |
| 35A | A | 1-methyl-tetrahydronaphthyl | 0 | O | 0 | 1,4-phenylene | 91 | — | 0.33 (IV) | 257 (M + $NH_4$) (B) |
| 36A | B | 2-methylnaphthyl | 1 | O | 0 | 1,4-phenylene | 97 | 135 | 0.23 (VI) | 267 (M + $NH_4$) (B) |
| 37A | A | 1-methylnaphthyl | 0 | O | 0 | 2-hydroxy-5-methylphenyl | 85 | 134 | 0.16 (IV) | 252 (M + H) (B) |
| 38A | B | 1-methylnaphthyl | 1 | O | 0 | 1,4-phenylene | 85 | — | 0.15 (IV) | 267 (N + $NH_4$) (B) |

TABLE III-continued $$R^1-(CH_2)_n-D-(CH_2)_m-G-NH_2$$

| Ex. No. | Method | R¹ | n | D | m | G | Yield (% of theory) | M.p. (° C.) | R_f | MS (m/e) |
|---|---|---|---|---|---|---|---|---|---|---|
| 39A | A | 1-naphthyl | 0 | O | 0 | 2-methyl-1,4-phenylene | 77 | — | 0.31 (VI) | 267 (M + NH₄) (B) |
| 40A | A | 1-naphthyl | 0 | O | 0 | 3-methyl-1,4-phenylene | 99 | — | 0.35 (XII) | 267 (M + NH₄) (B) |
| 41A | B | 1-naphthyl | 0 | O | 1 | 1,4-phenylene | 99 | — | 0.30 (IV) | 267 (M + NH₄) (B) |
| 42A | B | 1-naphthyl | 0 | O | 1 | 1,3-phenylene | 99 | — | 0.38 (IV) | 267 (M + NH₄) (B) |
| 43A | A | 1-naphthyl | 0 | O | 0 | 2,5-pyridinediyl | 79 | 87–88 | 0.41 (VII) | 237 (M + H) (B) |
| 44A | A | 5-isoquinolinyl | 0 | O | 0 | 1,4-phenylene | 71 | 122–3 | 0.38 (VII) | 237 (M + NH₄) (B) |
| 45A | A | 1-naphthyl | 0 | O | 0 | 1,3-phenylene | 71 | — | 0.59 (IV) | 236 (M + H) (B) |
| 46A | A | 8-quinolinyl | 0 | O | 0 | 2,5-pyridinediyl | 48 | 157 | 0.09 (XIII) | 238 (M + H) (B) |
| 47A | A | 1-naphthyl | 0 | S | 0 | 1,4-phenylene | 16 | 81 | 0.17 (IX) | 251 (M) (A) |

TABLE III-continued
$$R^1-(CH_2)_n-D-(CH_2)_m-G-NH_2$$
| Ex. No. | Method | R¹ | n | D | m | G | Yield (% of theory) | M.p. (° C.) | $R_f$ | MS (m/e) |
|---|---|---|---|---|---|---|---|---|---|---|
| 48A | B | 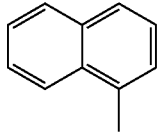 | 0 | O | 0 | 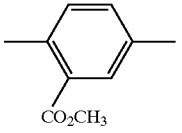 | 99 | — | 0.23 (IV) | 316 (M + Na) (C) |
| 49A | A | 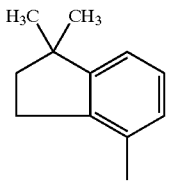 | 0 | O | 0 | 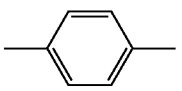 | 92 | — | 0.56 (VII) | 253 (M) (A) |
| 50A | B | 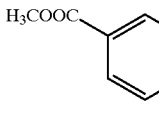 | 0 | O | 0 |  | 98 | — | 0.17 (VI) | 293 (M) (B) |
| 51A | A | 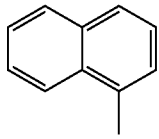 | 0 | O | 0 |  | 89 | 56 | 0.33 (IV) | 236 (M + H) (C) |
| 52A | A | 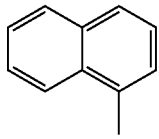 | 0 | O | 0 | 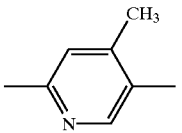 | 58 | 131 | 0.36 (VII) | 251 (M + H) (B) |
| 53A | A | 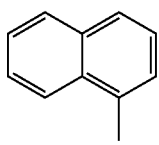 | 0 | NH | 0 | 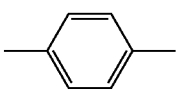 | 82 | 73–75 | 0.51 (IV) | 235 (M + H) (B) |
| 54A | B | 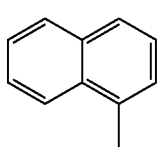 | 0 | O | 0 | 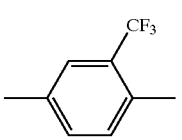 | 87 | — | 0.66 (IV) | 304 (M + H) (B) |
| 55A | B | 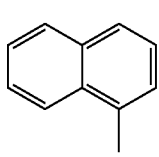 | 0 | O | 0 | 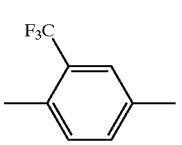 | 97 | — | 0.66 (IV) | 303 (M) (A) |

EXAMPLE 56A 4-(Naphthyl-1-oxy)phenol

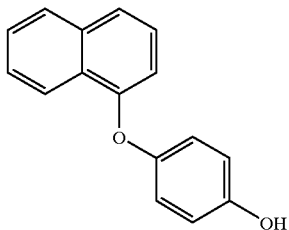

A solution of $NaNO_2$ (7.6 g; 110 mmol) in water (45 ml) is added dropwise at 0° C. to a suspension of the compound 51 A (25.8 g; 110 mmol) in 50% strength aqueous $H_2SO_4$ (400 ml) and stirred for 10 minutes. The reaction mixture is then heated at 100° C. for 2.5 h and extracted with dichloromethane (3×150 ml) after cooling. The combined organic phases are washed with water (1×100 ml), dried ($Na_2SO_4$) and concentrated in vacuo. The residue is chromatographed on silica gel using dichloromethane.

Yield: 6.1 g (24% of theory)

$R_f$=0.39 (IV)

MS (DCI, $NH_3$): m/e=237 (M+H)

EXAMPLE 57 A

3-Methyl-4-(naphthyl-1-oxy)phenol

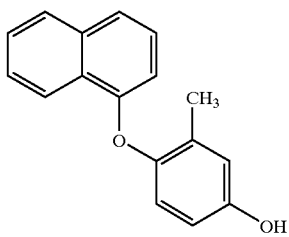

Preparation is carried out in analogy to the synthesis of Example 56 A starting from Example 39 A (5 0 g; 20 mmol).

Yield: 2.1 g (42% of theory)

$R_f$=0.36 (IV)

MS (DCI, $NH_3$): 251 (M+H)

EXAMPLE 58 A

[4-(Naphthyl-1-oxy)phenyl]aminosulphonic acid

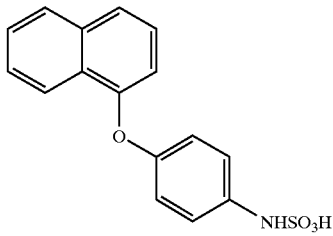

Triethylamine (6.44 g; 63.8 mmol) is added dropwise at 5° C. under argon to a solution of chlorotrimethylsilane (6.93 g; 63.8 mmol) in cyclohexane and the mixture is stirred for 1 h with ice-cooling. The compound from Example 51 A (15.0 g; 63.8 mmol) is dissolved in cyclohexane (350 ml) with heating and the solution is added dropwise at 5° C. to a solution of chlorotrimethylsilane/triethylamine. The reaction mixture is stirred at RT overnight and precipitated triethylammonium chloride is filtered off. It is washed with cyclohexane and the filtrate is concentrated in vacuo. The residue is taken up in dichloromethane (120 ml) and trimethylsilyl chlorosulphonate (12.0 g; 63.8 mmol) is added dropwise under argon at −15° C. over a period of 40 min. The reaction mixture is stirred at −15° C. overnight, then filtered under argon, treated dropwise at −15° C. with trifluoroacetic acid (7.3 g; 63.8 mmol) and stirred at −15° C. for a further 3 h. Precipitated product is filtered off, washed with dichloromethane and dried in vacuo.

Yield: 5.6 g (28% of theory)

M.p.: 220° C.

MS (FAB): m/e=316 (M+H)

EXAMPLE 59 A

4-Amino-2-(naphthyl-2-oxy)-pyridine

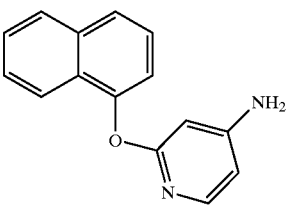

A suspension of 4-amino-2-chloropyridine (4.20 g; 32.7 mmol), 1-naphthol (7.06 g; 49.0 mmol) and potassium carbonate (6.77 g; 49.0 mmol) in pyridine (50 ml) in heated to reflux and treated with copper(II) oxide (5 8 g; 73 5 mmol), and the mixture is stirred at reflux for a further 18 hours.

Pyridine is then distilled off in vacuo, the residue is taken up in dichloromethane (100 ml) and the mixture is filtered through kieselgur. The filtrate is washed with water and the aqueous phase is extracted twice with dichloromethane. The combined dichloromethane phases are dried ($Na_2SO_4$) and concentrated in vacuo. The residue is chromatographed on silica gel using toluene:ethyl acetate (10:1).

Yield: 4.63 g (60% of theory)

M.p: 156° C.

$R_f$=0.12 (VI)

MS (CDCl, $NH_3$): m/e=237 (M+H)

EXAMPLE 60 A

6-Amino-2-(naphthyl-1-oxy)-pyridine

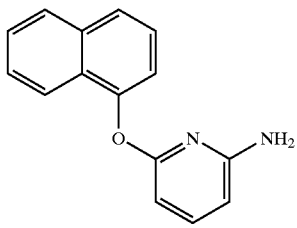

6-Amino-2-chloropyridine (6.60 g; 51.3 mmol) and 1-naphthol (11.1 g; 77.0 mmol) were reacted in analogy to Example 59 A.

Yield: 4.04 g (33% of theory)

$R_f$=0.59 (IV)

MS (ESI): m/e=237 (M+H)

EXAMPLES 61 A and 62 A

4-Amino-2-chloro-6-(naphthyl-1-oxy)pyridine
(Example 61 A)

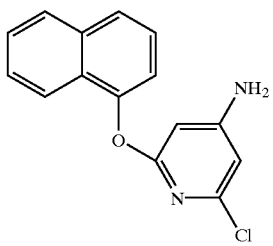

4-Amino-2,6-[bis(naphthyl)-1-oxy]pyridine
(Example 62 A)

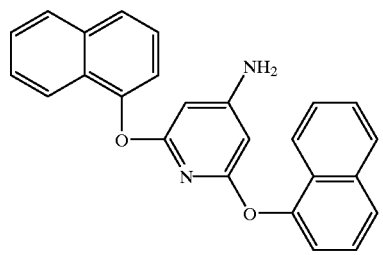

4-Amino-2,6-dichloropyridine (4.96 g; 30.4 mmol) and 1-naphthol (6.58 g; 45.6 mmol) were reacted in analogy to Example 59 A.

Yield: (Example 61 A): 0.14 g (1.8% of theory)

M.p.: 174° C.

$R_f$=0.37 (IV)

MS (DCI/NH$_3$): m/e=271 (M+H)

Yield: (Example 62 A): 3.59 g (44% of theory)

M.p.: 169° C.

$R_f$=0.48 (IV)

MS (DCI/NH$_3$): m/e=379 (M+H)

EXAMPLE 63 A 3-(Naphthyl-1-oxy)phenol

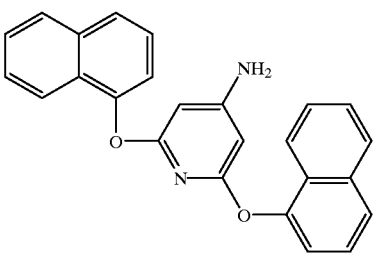

Preparation is carried out in analogy to the synthesis of Example 56 A, starting from Example 45 A (9.40 g; 40.0 mmol).

Yield: 3 08 g (33% of theory)

$R_f$=0.41 (CH$_2$Cl$_2$)

MS (DCI/NH$_3$): m/e=237 (M+H)

EXAMPLE 64 A

3-Bromo-5-(naphthyl-1-oxy)pyridine

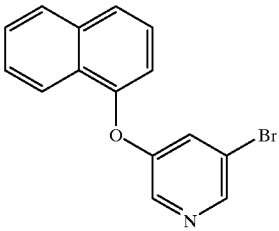

3,5-Dibromopyridine (24.9 g; 105 mmol), 1-naphthol (15.1 g; 105 mmol) and potassium carbonate (21.8 g; 158 mmol) are initially introduced into pyridine (200 ml) under argon. The reaction mixture is heated to reflux, treated after 15 min with copper(II) oxide (0.8 g; 10 mmol) and then heated to reflux for a further 10 h.

After cooling to room temperature, the reaction mixture is filtered and the residue is washed with dichloromethane. The filtrate is concentrated in vacuo. The residue is taken up in dichloromethane, and after fresh filtration the dichloromethane solution is washed with water. The aqueous phase is extracted with dichloromethane and the combined dichloromethane phases are dried (MgSO$_4$) and concentrated in vacuo. The residue is chromatographed on silica gel using toluene:ethyl acetate (10:1). The product thus obtained is recrystallized from diethyl ether/petroleum ether.

Yield: 2.9 g (10% of theory)

M.p.: 59–61° C.

$R_f$=0.54 (IV)

MS (DCI/NH$_3$): m/e=300, 302 (M+H)

EXAMPLE 65 A

3-Amino-5-(naphthyl-1-oxy)pyridine

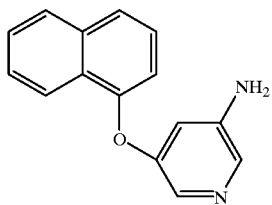

A solution of Example 64 A (1.98 g; 6.6 mmol) in THF (15 ml) is added dropwise at −33° C. to potassium amide [26.4 mmol, prepared from potassium (1.03 g) and cat amounts of FeCl$_3$] in liquid ammonia (50 ml)

After 10 min, NH$_4$Cl (2.0 g) is added and the ammonia is allowed to evaporate The residue is treated with a conc. aqueous NH$_4$Cl solution (25 ml) and water (25 ml) and extracted with dichloromethane (5×25 ml). The combined org. phases are washed with water (1×25 ml), dried and concentrated in vacuo.

Yield: 1.40 g (90% of theory)

M.p.: 91–92° C.

R$_f$=0.22 (VII)

MS (ESI): m/e=237 (M+H)

The compounds shown in Table IV are prepared in analogy to Example 1 A

TABLE IV $R^1$—D—G—NO$_2$

| Ex. No. | R$^1$ | D | G | Yield (% of theory) | M.p. (° C.) | R$_f$ | MS (m/e) |
|---|---|---|---|---|---|---|---|
| 66A | naphthyl-methyl | 0 | 2,4-dimethyl-CO$_2$CH$_3$-phenyl a) | 85 | — | 0.53 (XXXIX) | 341 (M + NH$_4$) (B) |
| 67A | CH$_3$O$_2$C-(3-methyl)phenyl | 0 | phenyl | 74 | 66–7.5 | 0.46 (V) | 296 (M + Na) (C) |
| 68A | 2-methylbiphenyl | 0 | phenyl | 81 | 72.5–4 | 0.66 (IV) | 314 (M + Na) (C) |
| 69A | 4-tert-butylphenyl | 0 | phenyl | 60 | 53–6 | 0.69 (IV) | 294 (M + Na) (C) |
| 70A | 3-isopropylphenyl | 0 | phenyl | 90 | 44–6 | 0.71 (XXX) | 280 (M + Na) (C) |

TABLE IV-continued
R¹—D—G—NO₂
| Ex. No. | R¹ | D | G | Yield (% of theory) | M.p. (° C.) | $R_f$ | MS (m/e) |
|---|---|---|---|---|---|---|---|
| 71A | 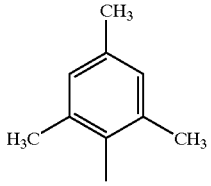 | 0 |  | 71 | 72–5 | 0.68 (XXX) | 280 (M + Na) (C) |
| 72A | 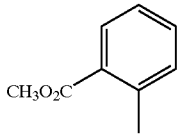 | 0 | 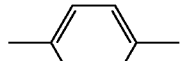 | 84 | 68.5–71.5 | 0.43 (IV) | 296 (M + Na) (C) |
| 73A | 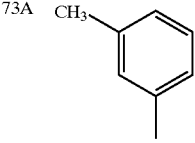 | 0 |  | 61 | 62–4 | 0.65 (IV) | 252 (M + Na) (C) |
| 74A | 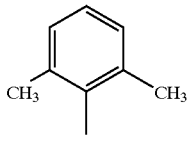 | 0 |  | 59 | — | 0.69 (IV) | 266 (M + Na) (C) |
| 75A | 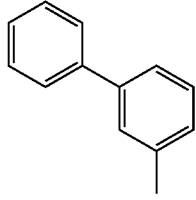 | 0 | 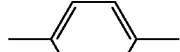 | 98 | — | — | — |
| 76A | 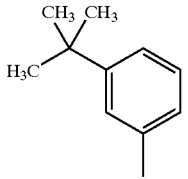 | 0 | 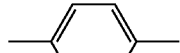 | 95 | — | — | — |
| 77A | 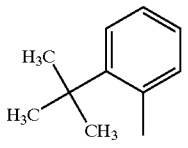 | 0 | 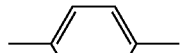 | 88 | 106–9 | 0.58 (XXX) | 294 (M + Na) (C) |
| 78A | 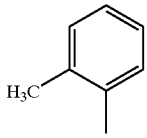 | 0 | 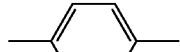 | 88 | — | 0.66 (IV) | 252 (M + Na) (C) |

TABLE IV-continued

R¹—D—G—NO₂

| Ex. No. | R¹ | D | G | Yield (% of theory) | M.p. (° C.) | R_f | MS (m/e) |
|---|---|---|---|---|---|---|---|
| 79A | H₃C—⌬(CH₃) | O | —⌬— | 89 | 59–61 | 0.75 (IV) | 280 (M + Na) (C) |
| 80A | H₃C(CH₃)—⌬(CH₃)—CH(CH₃)₂ | O | —⌬— | 51 | 81–3 | 0.72 (XXX) | 322 (M + Na) (C) | a)Reaction temperature 80° C.

EXAMPLE 81 A

Methyl 4-fluoro-2-nitrobenzoate

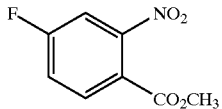

Thionyl chloride (31.5 ml; 0.432 mol) was slowly added dropwise at 0° C. to a solution of 4-fluoro-2-nitrobenzoic acid (16.0 g; 86.4 mmol) in methanol (240 ml). After warming to RT, stirring overnight and boiling under reflux for 4 h, the reaction solution was concentrated in vacuo and partitioned between ethyl acetate and potassium hydrogencarbonate solution. Drying and concentration of the organic phase afforded a yellow oil.

Yield: 15.7 g (85% of theory)

$R_f$=0.53 (XXIX)

MS (EI): m/e=199 (M)

The compounds in shown in Table V are prepared in analogy to Examples 29 A (method A) and 30 A (method B):

TABLE V

R¹—O—G—NH₂

| Ex. No. | Method | R¹ | G | Yield (% of theory) | M.p. (° C.) | R_f | MS (m/e) |
|---|---|---|---|---|---|---|---|
| 82A | B | naphthyl | —⌬(CH₃)—CO₂CH₃ | 84 | — | 0.49 (IV) | 294 (M + H) (B) |
| 83A | A | CH₃O₂C—⌬ | —⌬— | 99 | — | 0.17 (IV) | 244 (M + H) (C) |
| 84A | A | 2-biphenyl | —⌬— | 96 | — | 0.29 (IV) | 262 (M + H) (C) |

TABLE V-continued
R¹—O—G—NH₂
| Ex. No. | Method | R¹ | G | Yield (% of theory) | M.p. (° C.) | R$_f$ | MS (m/e) |
|---|---|---|---|---|---|---|---|
| 85A | A | 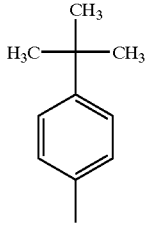 | 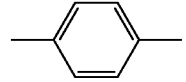 | 91 | — | 0.30 (IV) | 242 (M + H) (C) |
| 86A | A | 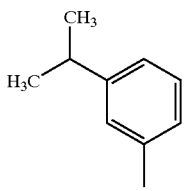 | 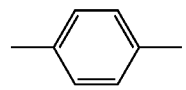 | 79 | — | 0.31 (IV) | 228 (M + H) (C) |
| 87A | A | 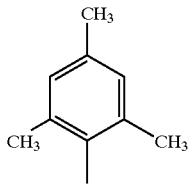 | 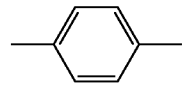 | 89 | 90–3 | 0.15 (X) | 228 (M + H) |
| 88A | A | 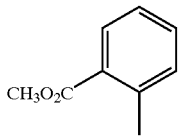 | 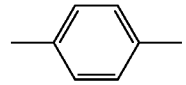 | 38 | 76 | 0.10 (X) | 244 (M + H) (C) |
| 89A | A | 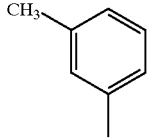 | 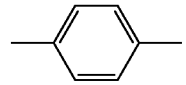 | 86 | 66–72 | 0.14 (X) | 200 (M + H) (C) |
| 90A | A | 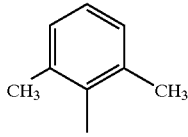 |  | 81 | 88–90 | 0.14 (X) | 214 (M + H) (C) |
| 91A | A | 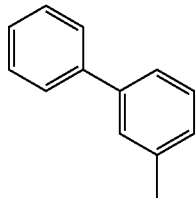 | 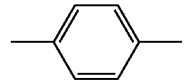 | 86 | 85–8 | 0.16 (X) | 262 (M + H) (C) |
| 92A | A | 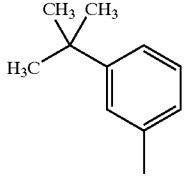 | 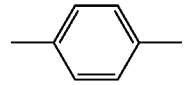 | 95 | — | 0.21 (X) | 242 (M + H) (C) |

TABLE V-continued $R^1$—O—G—NH$_2$

| Ex. No. | Method | $R^1$ | G | Yield (% of theory) | M.p. (° C.) | $R_f$ | MS (m/e) |
|---|---|---|---|---|---|---|---|
| 93A | A | 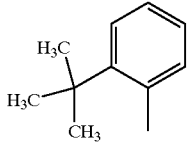 | 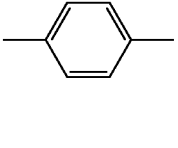 | 93 | — | 0.18 (X) | 242 (M + H) (C) |
| 94A | A | 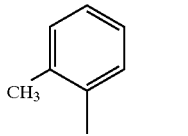 |  | 88 | 52–6 | 0.20 (X) | 199 (M) (D) |
| 95A | A | 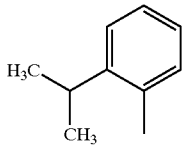 | 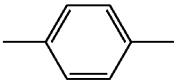 | 95 | — | 0.22 (X) | 227 (M) (D) |
| 96A | A | 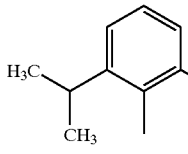 |  | 96 | 92–5 | 0.18 (X) | 269 (M) (D) |

EXAMPLE 97 A 4-(2-Ethoxycarbonylindan-4-oxy)-1-nitrobenzene

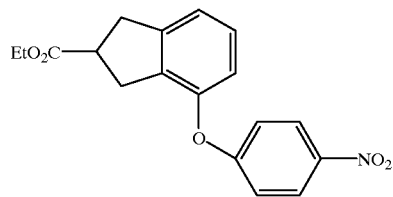

Preparation was carried out in analogy to the preparation of Example 1 A, starting from 4-fluoro-1-nitrobenzene (3.76 g; 26.7 mmol) and ethyl 4-hydroxy-indan-2-carboxylate (5.50 g; 26.7 mmol; EP 425 946).

Yield: 0.70 g (7.5% of theory)

$R_f$=0.37 (X)

MS (DCI, NH$_3$): m/e=345 (M+NH$_4$)

EXAMPLE 98 A 4-(2-Ethoxycarbonyl-indan-4-oxy)-aniline

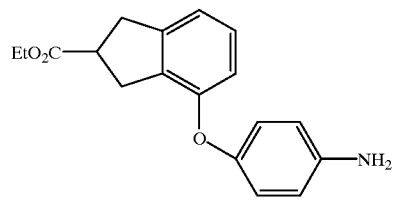

Preparation was carried out in analogy to the preparation of Example 30 A, starting from Example 97 A (0.70 g; 2.14 mmol).

Yield: 0 616 g (94% of theory)

$R_f$=0.12 (XXXI)

MS (DCI, NH$_3$): m/e=315 (M+NH$_4$)

EXAMPLE 99 A

3-Fluoro-5-(naphthyl-1-oxy)-1-nitrobenzene

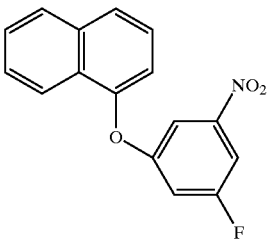

Preparation was carried out in analogy to the preparation of Example 13 A, starting from 1-naphthol (13.59 g; 94.3 mmol) and 3,5-difluoronitrobenzene (15.00 g; 94.3 mmol).

Yield: 17.9 g (67% of theory)

$R_f$=0.32 (III)

MS (DCI, NH$_3$): m/e=425 (M+NH$_4$)

EXAMPLES 100 A and 101 A

3-Fluoro-5-(naphthyl-1-oxy)-aniline (Example 100 A)

N-[3-Fluoro-5-(naphthyl-1-oxy)-phenyl] hydroxylamine (Example 101 A)

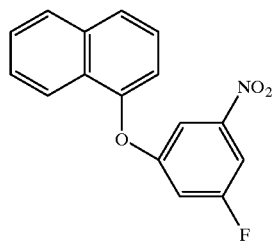

Example 100 A

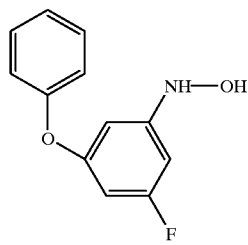

Example 101 A

A solution of Example 99 A in methanol (200 ml) and THF (15 ml) is treated with palladium, 10% on active carbon (0.2 g) and hydrogenated at 1 atm until 1.8 l of hydrogen has been absorbed. The reaction mixture is filtered through kieselgur and the filtrate is concentrated in vacuo. The residue is chromatographed on silica gel using toluene:ethyl acetate (10:1).

Yield: (Example 100 A): 3.92 g (44% of theory)

$R_f$=0.55 (IV)

MS (DCI, $NH_3$): m/e=254 (M+H)

Yield: (Example 101 A): 5.2 g (47% of theory)

$R_f$=0.33 (IV)

MS (DCI, $NH_3$): m/e=270 (M+H)

The examples shown in Table VI are prepared in analogy to the preparation of Example 1 A:

TABLE VI $R^1$—O—⟨phenyl⟩—$NO_2$

| Ex. No. | $R^1$ | Yield (% of theory) | M.p. (° C.) | $R_f$ | MS (m/e) |
|---|---|---|---|---|---|
| 102 A | [N-acetyl-4-methylnaphthalen-1-yl] | 84 | 205 | 0.34 (XVI) | 321 (M − H) (C) |
| 103 A | b) [2-methyl-5-methyl-1,2,3,4-tetrahydroisoquinolin-yl] | 74 | 80 | 0.17 (XXXV) | 285 (M + H) (C) |
| 104 A | c) [2-allyl-5-methyl-1,2,3,4-tetrahydroisoquinolin-yl] | 99 | — | 0.80 (VII) | 311 (M + H) (C) |

TABLE VI-continued

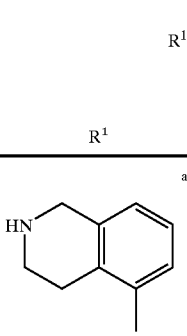

| Ex. No. | R¹ | Yield (% of theory) | M.p. (° C.) | $R_f$ | MS (m/e) |
|---|---|---|---|---|---|
| 105 A | a) 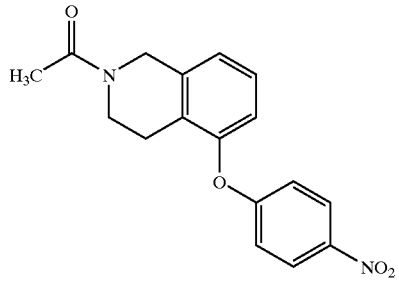 | 74 | 215 | — | 269 (M − H) (C) | a)Starting from 2-acetyl-1,2,3,4H-tetrahydroisoquinolin-5-ol
b)Starting from N-methyl-1,2,3,4H-tetrahydroisoquinolin-5-ol which was prepared from isoquinolin-5-ol according to Bull. Soc. Chim. Fr. 1961, 270
c)Starting from N-allyl-1,2,3,4H-tetrahydroisoquinolin-5-ol which was prepared from isoquinolin-5-ol according to DOS [German Offenlegungsschrift] 3329098

EXAMPLE 106 A 1-(2-Acetyl-1,2,3,4H-tetrahydroisoquinolin-5-oxy)-4-nitrobenzene

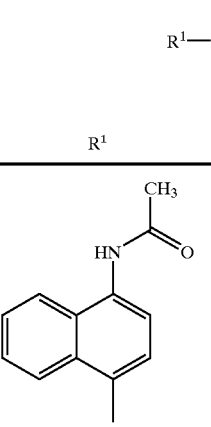

A solution of Example 105 A (12 g; 45 mmol), acetic anhydride (4.3 ml; 45 mmol) and pyridine (3.6 ml; 45 mmol) in dichloromethane was boiled under reflux for 4 h. After cooling to RT, the reaction batch was added to ice, and the organic phase was washed four times with water and concentrated. The residue was recrystallized from dichloromethane/petroleum ether.

Yield: 11.1 g (79% of theory)

M.p.: 137° C.

MS (ESI): m/e=313 (M+H)

The examples shown in Table VII were prepared in analogy to the preparation of Example 29 A (method A) and Example 30 A (method B)

TABLE VII

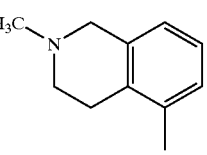

| Ex. No. | R¹ | Method | Yield (% of theory) | M.p. (° C.) | $R_f$ | MS (m/e) |
|---|---|---|---|---|---|---|
| 107 A | | A | 61 | 173 | 0.21 (VII) | — |
| 108 A | | A | 98 | — | 0.13 (XXXV) | — |

TABLE VII-continued

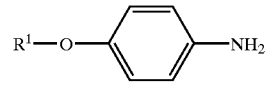

| Ex. No. | R¹ | Method | Yield (% of theory) | M.p. (° C.) | $R_f$ | MS (m/e) |
|---|---|---|---|---|---|---|
| 109 A |  | a) B | 74 | — | 0.13 (VIII) | 283 (M + H) (C) |
| 110 A | 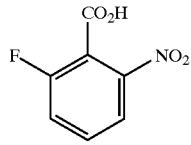 | B | 86 | 97–98 | 0.23 (XXVII) | 283 (M + H) (C) | a)Starting from Example 104 A

EXAMPLE 111 A

2-Fluoro-6-nitrobenzoic acid

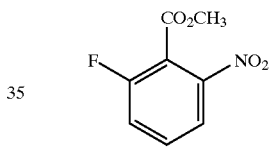

Example 111 A was prepared in analogy to Kaminski et al. J. Med. Chem. 1987, 30, 2047.

Yield: 70% of theory
M.p.: 149–51° C.
$R_f$=0.35 (XXXIX)
MS 185 (M) (A)

EXAMPLE 112 A

Methyl 2-fluoro-6-nitrobenzoate

Example 112 A was prepared in analogy to the procedure of Example 81 A.

Yield: 93% of theory
M.p.: 60–1° C.
$R_f$=0.83 (XXVII)
MS 199 (M) (A)

The examples of Table VIII were prepared in analogy to the procedure of Example 1 A.

TABLE VIII

| Ex. | | Yield (%) | M.p. (° C.) $R_f$ | MS (m/e) |
|---|---|---|---|---|
| 113 A | 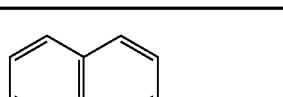 | 20 | Öl 0.61 (IV) | 346 (M + NO₂) (C) |

TABLE VIII-continued

| Ex. | | Yield (%) | M.p. (° C.) | $R_f$ | MS (m/e) |
|---|---|---|---|---|---|
| 114 A[a)] | (structure: N-methyl tetrahydroquinoline with 8-O-(4-nitrophenyl), HClx) | 48 | | 0.76 (XXXVIII) | 285 (M − Cl) (C) |

[a)] After preparation of the hydrochloride by treatment of the free amine with 1N HCl/ether; starting from N-methyl-1,2,3,4H-tetrahydroquinolin-8-ol which was prepared from quinolin-8-ol according to DOS [German Offenlegungsschrift] 750339

The examples of Table IX were prepared in analogy to the procedure of Example 30 A.

TABLE IX

| Ex. | | Yield (%) | M.p. (° C.) | $R_f$ | MS (m/e) |
|---|---|---|---|---|---|
| 115 A | (naphthyl-O-phenyl with CO2CH3 and NH2) | 71 | Öl | 0.42 (VI) | 294 (M + H) (C) |
| 116 A | (N-methyl tetrahydroquinoline with 8-O-(4-aminophenyl)) | 12 | Öl | 0.6 (XXXVIII) | 455 (M + H) (C) |

EXAMPLE 117 A

2-Propyl-5-(4-hydroxyphenoxy)-[1,2,3,4H]-tetrahydroisoquinoline

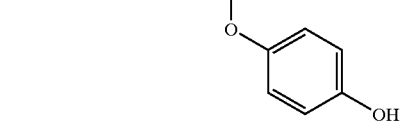

Example 117 A was prepared in analogy to Example 56 A and precipitation with 1N HCl/ether.

Yield: 47% of theory

M.p.: 239–40° C.

$R_f$=0 58 (XL)

MS 284 (M+H) (C)

TABLE X
The examples shown in Table X were prepared in analogy to the preparation of Example 1 A.
R¹—O—G—NO₂
| Ex. No. | R¹ | G | Yield (%) | $R_f$ | M.p. (° C.) | MS (m/e) |
|---|---|---|---|---|---|---|
| 518 A | 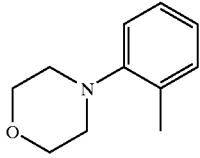 | 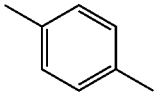 | 78.5 | 0.46 (XVI) | — | 301 (M + H) (E) |
| 119 A | 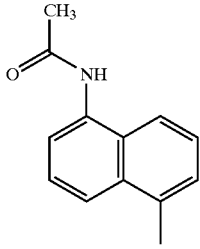 | 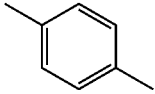 | 78.8 | 0.19 (VII) | 215 | 321 (M − 1) (APCI) |
| 120 A[a)] | 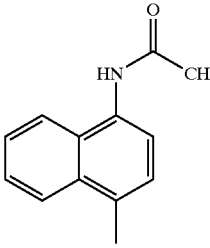 | 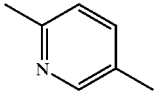 | 72 | 0.67 (XXXIII) | 211 | 324 (M + H) (E) |
| 121 A[b)] | 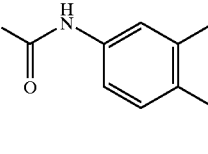 | 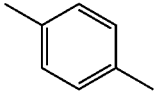 | 54 | 0.38 (XLI) | 199 | 280 (A) |
| 122 A | 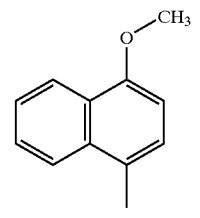 | 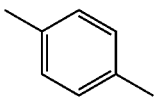 | 45.2 | 0.55 (X) | 145–48° C. | 296 (M + H) (E) |
| 123 A[a)] | 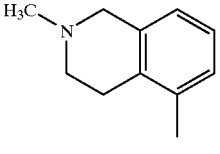 | 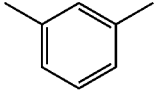 | 24 | 0.48 (XXXIII) | 112 | 285 (M + H) (E) |
| 124 A | 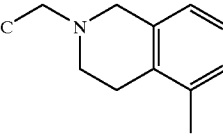 | 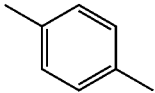 | 4.1 | 0.29 (XLI) | | |
[a)] Reaction at 140° C.
[b)] 5 After reaction complete acetylation with acetic anhydride, pyridine, RT.

The examples shown in Table XI were prepared in analogy to the preparation of Example 29 A.
TABLE XI
R¹—O—G—NH₂
| Ex. No. | R¹ | G | Yield (%) | $R_f$ | M.p. (° C.) | MS (m/e) |
|---|---|---|---|---|---|---|
| 125 A | 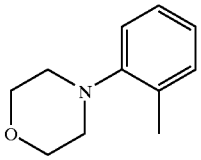 | 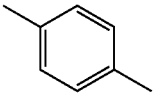 | 100 | 0.32 (XVI) | 128 | |
| 126 A | 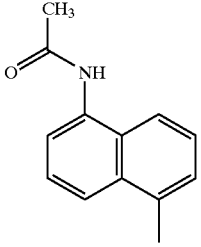 | 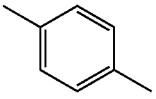 | 100 | 0.11 (VII) | 210 | |
| 127 A | 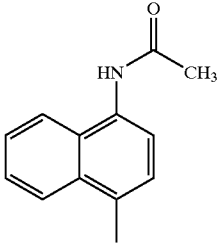 | 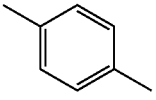 | 91 | 0.53 (XXXIV) | 187 | 294 |
| 128 A | 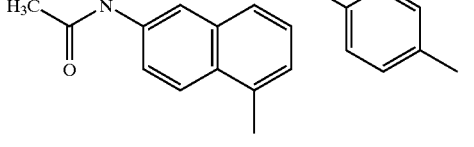 | 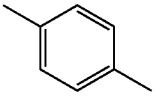 | 38 | 0.28 (XLI) | | 293 (M + H) (E) |
| 129 A | 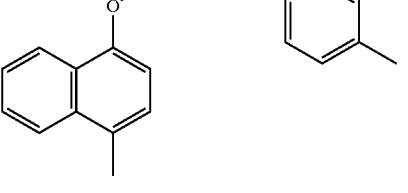 | 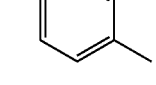 | 95 | 0.32 (XLII) | 109 | 266 (M + H) (E) |
| 130 A | 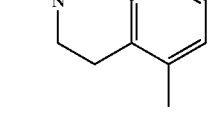 |  | 86 | 0.3 (XLI) | amorph | 255 (M + H) (E) |

EXAMPLE 131 A 4-(2-Methyl-1,2,3-4-tetrahydroisoquinolin-5-yl-oxy)-phenol semi-hydrosulphate

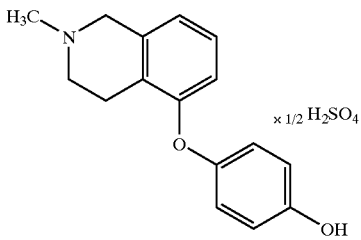

A 5% strength aqueous NaNO₂ solution (30 ml, 21.7 mmol) is added dropwise at a temperature of 3–4° C. in the course of 60 min to a suspension of the compound from Example 108 A (5 g; 19.7 mmol) in 20% strength sulphuric acid (200 g). Excess nitrite is then destroyed by addition of 200 mg of amidosulphuric acid and the batch is heated at 100° C. for 4 h. The reaction mixture is cooled to 3° C., and the deposited precipitate is filtered off and washed with isopropanol.

Yield: 4.1 g (68% of theory)

$R_f$=0.28 (XXXIII)

M.p.: 207° C.

MS (DCI, isobutane): m/e=256 (M+H)

EXAMPLE 132 A

Methyl 5-hydroxy-naphthalene-2-carboxylate

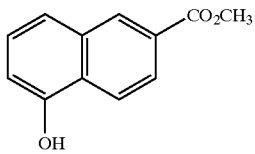

5-Methoxy-2-naphthoic acid (49 7 g; 0 246 mol, J Med Chem 1993, 36, 2485) in glacial acetic acid (450 ml) and in 48% strength aqueous hydrobromic acid solution (450 ml) is heated to reflux for 15 h After cooling, the reaction mixture is concentrated in vacuo and is extracted with dichloromethane after addition to water The organic phase is washed with water, dried over MgSO₄ and concentrated in vacuo. The residue is dissolved in MeOH (1.6 l) The solution is saturated with hydrogen chloride (about 1 h), the reaction mixture heating to reflux temperature. The solvent is then stripped off in vacuo, the residue is taken up in ethyl acetate, and the mixture is washed with satd NaCl solution, dried (MgSO₄) and concentrated in vacuo. The residue is chromatographed on silica gel using dichloromethane:ethyl acetate (20:1). The product thus obtained is stirred with dichloromethane/petroleum ether, filtered off with suction and dried in vacuo.

Yield: 31.5 g (63% of theory)

M.p.: 116–117° C.

$R_f$=0.33 (IV)

MS (ESI): m/e=220 (M+NH₄)

EXAMPLE 133 A

6-Hydroxymethyl-1-naphthol

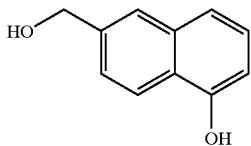

A 1N solution of lithium aluminium hydride in THF (112.5 ml; 112.5 mmol) is added dropwise to a solution of Example 132 A (18.2 g; 90 mmol) in THF (500 ml) at 20–25° C. After 3 h, the mixture is treated with conc. aqueous NH₄Cl solution (250 ml) and extracted with ethyl acetate (3x). The combined organic phases are washed with conc. aqueous NH₄Cl solution (2x), dried (MgSO₄) and concentrated in vacuo. The residue is recrystallized from ethyl acetate.

Yield: 11.7 g (75% of theory)

M.p.: 169–170° C.

$R_f$=0.22 (dichloromethane:ethyl acetate=10 l)

MS (DCI): m/e=192 (M+NH₄)

EXAMPLE 134 A

1-Bromo-6-hydroxymethyl-naphthalene

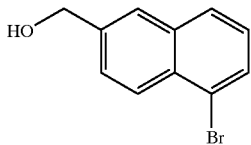

Preparation was carried out in analogy to the preparation of Example 133 A, starting from methyl 5-bromo-naphthalene-2-carboxylate (104.7 g; 395 mmol; Aust. J. Chem. 1965, 18, 1351).

Yield: 78.7 g (84% of theory)

$R_f$=0.52 (VII)

MS (DCI/NH₃): m/e=254 (M+NH₄)

EXAMPLE 135 A

4-Hydroxy-2-hydroxymethyl-indan

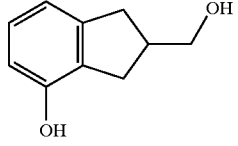

Preparation was carried out in analogy to the preparation of Example 133 A, starting from ethyl 4-hydroxyindan-2-carboxylate (10.0 g; 48 5 mmol; EP 425 946).

Yield: 7.0 g (84% of theory)

M.p.: 101° C.

$R_f$=0 33 (VII)

MS (DCI/NH₃): m/e=224 (M+NH₄)

EXAMPLE 136 A 4-(1-Naphthyloxy)-pyridine

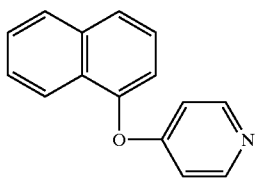

A suspension of 1-naphthol (24.00 g; 166.5 mmol), 4-chloropyridine hydrochloride (24.97 g; 166.5 mmol) and potassium carbonate (46.02 g; 332.9 mmol) is deoxygenated in pyridine (200 ml) using argon. Copper(II) oxide (26.48 g; 332.9 mmol) is then added and the reaction mixture is stirred under argon overnight under reflux. The pyridine is then stripped off in vacuo, and the residue is taken up in dichloromethane, washed with water, dried ($Na_2SO_4$) and concentrated in vacuo. The residue is chromatographed on silica gel using toluene:EA(10:1). The product thus obtained is stirred in diethyl ether, filtered off and dried in vacuo.

Yield: 6.80 g (18% of theory)

M.p.: 85–86° C.

$R_f$=0.29 (VII)

MS (DCI/$NH_3$): m/e=222 (M+H)

EXAMPLE 137 A 4-(1-Naphthyloxy)-pyridine-N-oxide

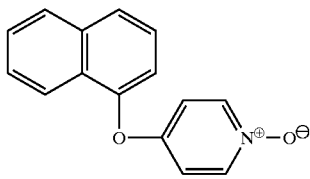

A solution of Example 136 A (6.62 g; 29 9 mmol) in dichloromethane (40 ml) is treated with m-chloroperbenzoic acid, 80% strength (7 10 g; 32 9 mmol), stirred at room temperature for 24 h and then heated to reflux for a further 2 h The reaction mixture is washed twice with satd aqueous $NaHCO_3$ solution. The combined aqueous phases are extracted with dichloromethane and the combined dichloromethane phases are dried ($Na_2SO_4$) and concentrated in vacuo. The residue is crystallized from dichloromethane/petroleum ether.

Yield: 3.85 g (54% of theory)

M.p.: 128° C.

MS (ESI): m/e=260 (M+Na)

EXAMPLE 138 A

2-Chloro-4-(1-naphthyloxy)-pyridine

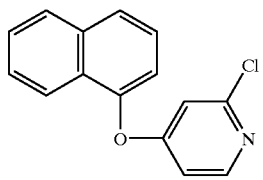

A suspension of Example 137 A (4.50 g; 19.0 mmol) in phosphoryl chloride (50 ml) is heated to reflux temperature in the course of 1.5 h and stirred at this temperature overnight. The phosphoryl chloride is stripped off in vacuo, the residue is treated with ice water and the mixture is extracted with dichloromethane. The organic phase is washed with sat. $NaHCO_3$ solution, dried ($Na_2SO_4$) and concentrated in vacuo. The residue is chromatographed on silica gel using toluene:EA (5:1).

Yield: 2.99 (60% of theory)

$R_f$=0.58 (IV)

MS (ESI): m/e=256 (M+H)

EXAMPLE 139 A

2-Amino-4-(1-naphthyloxy)-pyridine

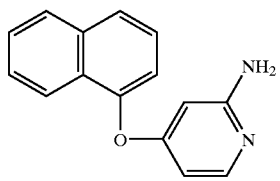

Preparation was carried out in analogy to the preparation of Example 65 A, starting from Example 138 A (2.08 g; 8.13 mmol).

Yield: 1.32 g (69% of theory)

M.p.: 97–99° C.

$R_f$=0.23 (VII)

MS(ESI): m/e=237 (M+H)

EXAMPLE 140 A 1-(6-Hydroxymethyl-naphthyl-2-oxy)-3-nitrobenzene

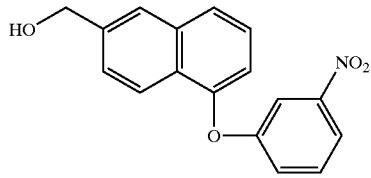

A solution of Example 133 A (9.40 g; 54.0 mmol) in DMF (200 ml) is treated with potassium carbonate (7.50 g; 54.0 mmol) and stirred at room temperature for 1 h. After addition of 3-fluoro-1-nitrobenzene (7.60 g; 54.0 mmol), the reaction mixture is stirred at 155° C. (bath temperature) overnight under argon. The DMF is then evaporated off in vacuo, and the residue is taken up with water and ethyl acetate (1:1) and filtered. After phase separation, the aqueous phase is extracted a further three times with ethyl acetate. The combined organic phases are washed twice with sat. aqueous NaCl solution, dried (MgSO$_4$) and concentrated in vacuo in a rotary evaporator. The residue is chromatographed on silica gel using dichloromethane:EA (20:1).

Yield: 1.75 g (11% of theory)

R$_f$=0.56 (dichloromethane:EA=20:3)

MS (DCI/NH$_3$): m/e 313 (M+NH$_4$)

EXAMPLE 141 A 3-(6-Methyl-naphthyl-1-oxy)-aniline

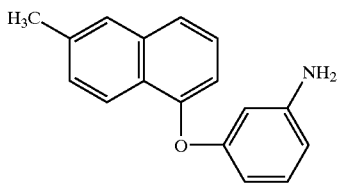

A suspension of Example 140 A (1.94 g; 6.60 mmol) and palladium on active carbon, 10% strength (0.6 g) in THF:MeOH (1:1, 50 ml) is hydrogenated for 3 h at a hydrogen pressure of 3 bar. The reaction mixture is filtered through silica gel. The filtrate is concentrated in vacuo and the residue is chromatographed on silica gel using dichloromethane.

Yield: 1.05 g (64% of theory)

R$_f$=0.60 (dichloromethane)

MS (ESI): m/e=250 (M+H)

EXAMPLE 142 A 2-(6-Hydroxymethyl-naphthyl-1-oxy)-5-nitro-pyridine

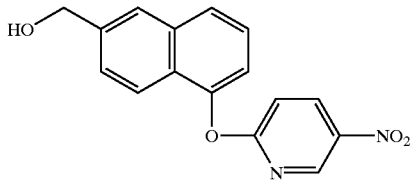

Preparation was carried out in analogy to the preparation of Example 12 A, starting from Example 133 A (10.0 g; 57.4 mmol).

Yield: 15.2 g (88% of theory)

M.p.: 94° C.

R$_f$=0.12 (IV)

MS (ESI): m/e=297 (M+H)

EXAMPLE 143 A

5-Amino-2-(6-hydroxymethyl-naphthyl-1-oxy)-pyridine

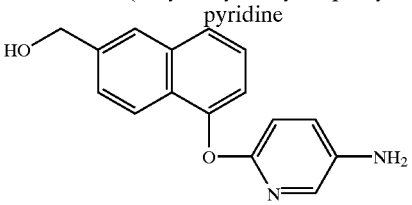

A suspension of Example 142 A (10.3 g; 34.8 mmol) and platinum on active carbon, 10% strength (1.0 g) in THF (80 ml) is hydrogenated for 4 h at room temperature and 1 bar of hydrogen. The reaction mixture is filtered through kieselgur and concentrated in vacuo.

Yield: 9.2 g (89% of theory)

M.p.: 163° C.

R$_f$=0.09 (VII)

MS (ESI): m/e=267 (M+H)

EXAMPLE 144 A 3-(6-Methoxymethyl-naphthyl-1-oxy)-aniline

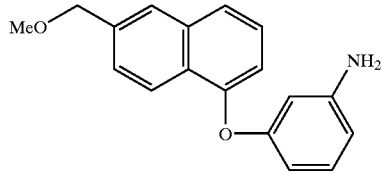

Iodomethane (0.853 g; 6.01 mmol) is added at 50° C. (bath temperature) to sodium hydride, 60% strength in liquid paraffin (0.152 g; 3.80 mmol) in THF (5 ml), then a solution of Example 140 A (0.901 g; 3.05 mmol) in THF (10 ml) is added dropwise in the course of 15 min and the mixture is stirred at 50° C. for a further 10 min. After addition of water, it is extracted with ethyl acetate. The organic phases are washed twice with satd aqueous NaCl solution, dried (MgSO$_4$) and concentrated in vacuo. The residue is chromatographed on silica gel using dichloromethane. The 1-(6-methoxymethylnaphthyl-1-oxy)-3-nitrobenzene obtained (0.43 g) is hydrogenated for 3 h at room temperature and 1 bar of hydrogen using platinum on active carbon, 10% strength (0.1 g) in THF (15 ml) without further purification. The reaction mixture is filtered through kieselguhr and concentrated in vacuo. The residue is chromatographed on silica gel using dichloromethane:EA (20:1).

Yield: 0.070 g (7% of theory)

R$_f$=0.50 (dichloromethane:EA=10:1)

MS (EI): m/e=279 (M)

EXAMPLE 145 A (R,S)-1-(2-Hydroxymethyl-indanyl-4-oxy)-3-nitrobenzene

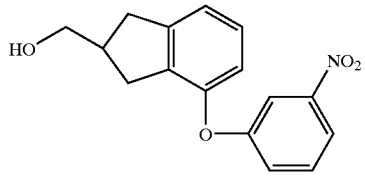

Preparation was carried out in analogy to the preparation of Example 140 A, starting from Example 135 A (60.0 g; 365.4 mmol).

Yield: 34.4 g (32% of theory)

M.p.: 77–79° C.

$R_f$=0.24 (VI)

MS (ESI): m/e=286 (M+H)

EXAMPLE 146 A (R,S)-3-(2-Hydroxymethyl-indanyl-4-oxy)-aniline

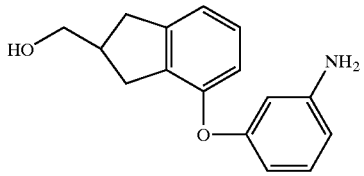

Preparation was carried out in analogy to the preparation of Example 30 A; starting from Example 145 A (4.45 g; 15.60 mmol).

Yield: 3.93 g (97% of theory)

$R_f$=0.42 (VII)

MS (ESI): m/e=256 (M+H)

EXAMPLE 147 A (R,S)-3-(2-Hydroxymethyl-indanyl-4-oxy)-phenol

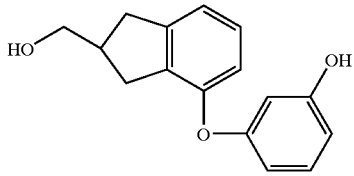

Preparation was carried out in analogy to the preparation of Example 56 A; starting from Example 146 A (3.07 g; 12.0 mmol).

Yield: 1.17 g (38% of theory)

$R_f$=0.49 (VII)

MS (DCI, $NH_3$): m/e=272 (M+$NH_4$)

EXAMPLE 148 A 3-(6-Hydroxymethyl-naphthyl-1-oxy)-phenol

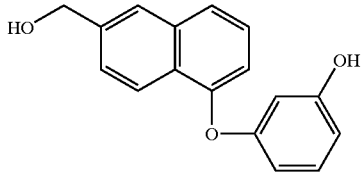

A solution of Example 134 A (88.9 g; 375 mmol) and 3-methoxyphenol (88.3 g; 651 mmol) in pyridine (1000 ml) is treated with potassium carbonate (89.9 g; 651 mmol), deoxygenated using argon and heated to reflux temperature under argon. After addition of copper(II) oxide (38.8 g; 488 mmol), the reaction mixture is heated to reflux overnight. After cooling to room temperature, the reaction mixture is filtered and the filtrate is concentrated in vacuo. The residue is taken up in ethyl acetate, filtered again and the filtrate is washed three times with water, dried ($MgSO_4$) and concentrated in vacuo in a rotary evaporator. The residue is chromatographed on silica gel using dichloromethane:EA (5:2). The mixture of 3-(6-hydroxymethylnaphthyl-1-oxy)-anisole ($R_f$=0.56 (VII), Example 134 A ($R_f$=0.51 (VII) and 3-methoxyphenol ($R_f$=0.6 (VII)) in the ratio 49%:32%:5% (HPLC) thus obtained is initially introduced into N-methylpyrrolidone (470 ml), treated with anhydrous sodium sulphide (111.2 g; 1.42 mmol) and stirred at 140° C. for 3 h. The reaction mixture is then introduced into 2 N HCl (1000 ml) and adjusted to pH 2–3 using 20% strength hydrochloric acid. The mixture is then extracted three times with ethyl acetate and the combined organic phases are washed twice with water, dried over $MgSO_4$ and concentrated in vacuo.

The residue is chromatographed on silica gel using toluene:EA (10:3).

Yield: 8.7 g (9% of theory)

$R_f$=0.54 (tol:EA=5.4)

MS (DCI/$NH_3$): m/e=284 (M+$NH_4$)

EXAMPLE 149 A 3-(2,3-Dimethylphenyloxy)-anisole

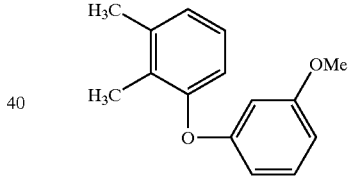

2,3-Dimethyl-1-bromobenzene (80.0 g; 0.432 mol), 3-methoxyphenol (107.3 g; 0.865 mol) and potassium carbonate (119.5 g; 0.865 mol) are initially introduced into pyridine (350 ml) under argon and heated to 100° C. After addition of copper(II) oxide (51.6 g; 0.648 mol), the batch is stirred at 140° C. After 15 h and 40 h, 2,3-dimethyl-1-bromobenzene (80.0 g; 0.432 mol after 15 h and 66.0 g; 0.357 mol after 40 h) is added again. After 64 h, the batch is concentrated in vacuo, the residue is taken up in ethyl acetate and the mixture is adjusted to pH 2–3 using half-conc. hydrochloric acid. After phase separation, the organic phase is washed with satd NaCl solution, dried ($Na_2SO_4$) and concentrated in vacuo in a rotary evaporator. The residue is chromatographed on silica gel using tol:EA=5:1.

Yield: 94.9 g (36% of theory)

$R_f$=0.76 (toluene)

MS (DCI, $NH_3$): m/e=246 (M+$NH_4$)

EXAMPLE 150 A 3-(2,3-Dimethylphenyloxy)-phenol

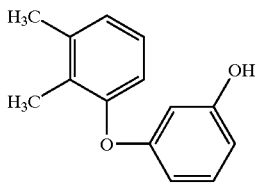

Example 149 A (109.6 g; 480 mmol) is initially introduced into 48% aqueous hydrogen bromide (900 ml) and acetic acid (1500 ml) and the mixture is stirred under reflux overnight. The batch is then concentrated in vacuo, the residue is taken up in water and the mixture is extracted three times with ethyl acetate. The combined organic phases are washed twice with water, dried (MgSO$_4$) and concentrated in vacuo. The residue is chromatographed on silica gel using toluene:EA (10:1).

Yield: 86.5 g (83% of theory)

R$_f$=0.15 (toluene)

MS (ESI): m/e=215 (M+H)

EXAMPLE 151 A 4,4,4-Trifluorobutyl thiocyanate

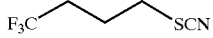

A stirred solution of 4,4,4-trifluorobutanol (35 g; 0.027 mol) and triethylamine (28.3 g; 0.280 mol) in 200 ml of dichloromethane was treated dropwise at 0° C. with a solution of methanesulphonyl chloride (32.1 g; 0.280 mol) in 100 ml of dichloromethane. After the end of the addition, the mixture was stirred for a further 30 min, then poured onto ice and the phases were subsequently separated. The organic phase was dried over magnesium sulphate and concentrated under reduced pressure. 55 g of crude 4,4,4-trifluorobutyl methanesulphonate were obtained as an orange oil.

The mesylate (55 g) was boiled under reflux for 6 h with sodium thiocyanate (30.6 g; 0.30 mol) in acetone (300 ml). After cooling to room temperature, the mixture was poured onto ice, the phases were separated and the organic phase was dried over magnesium sulphate. After filtration and concentration under reduced pressure, 41 g (89% of theory) of 4,4,4-trifluorobutyl thiocyanate were obtained as an oil.

$^{19}$F-NMR (376 MHz, CDCl$_3$; CFCl$_3$) δ [ppm]: −66.3
$^1$H-NMR (400 MHz, CDCl$_3$, TMS) δ [ppm]: 2.15 (m, 2H); 2.3 (m, 2H); 3.05 (t, J=7.1 Hz, 2H)

The compounds shown in Table XII were prepared analogously to Example 151 A.

TABLE XII

R$^{51}$—CF$_2$—CR$^{49}$R$^{50}$—U—CH$_2$—CH$_2$—SCN

| Ex. No. | U | R$^{49}$ | R$^{50}$ | R$^{51}$ | Yield [%] |
|---|---|---|---|---|---|
| 152 A | O | H | H | F | 91.5 |
| 153 A | O | CF$_3$ | H | F | 94 |
| 154 A | CH$_2$ | F | F | F | 93 |
| 155 A | — | Cl | F | Cl | 55 |

EXAMPLE 156 A 4,4,4-Trifluorobutanesulfonyl chloride

Chlorine was passed at 20 to 40° C. into a solution of Example 151 A (40 g; 0.236 mol) in aqueous acetic acid (150 ml of acetic acid and 70 ml of water) and the progress of the reaction was monitored by gas chromatography. When the chlorination was complete, the excess chlorine was displaced by means of passage of a stream of nitrogen, 200 ml of water were added and the reaction mixture was extracted several times with dichloromethane. The combined organic phases were dried over magnesium sulphate, filtered off therefrom and concentrated under reduced pressure. 44 g (89% of theory) of 4,4,4-trifluorobutanesulfonyl chloride were obtained as a yellow oil.

$^{19}$F-NMR (376 MHz, CDCl$_3$; CFCl$_3$) δ [ppm]: −66.65 (t, J=10 Hz) $^1$H-NMR (400 MHz, CDCl$_3$, TMS) δ [ppm]: 3.8 (m, 2H); 2.35 (m, 4H)

The compounds shown in Table XIII were prepared analogously to Example 156 A

TABLE XIII

R$^{51}$—CF$_2$—CR$^{49}$R$^{50}$—U—CH$_2$—CH$_2$—SO$_2$—Cl

| Ex. No. | U | R$^{49}$ | R$^{50}$ | R$^{51}$ | NMR-Data(CDCl$_3$) $^{19}$F:CFCl$_3$/$^1$H:TMS: δ[ppm] | Yield [%] |
|---|---|---|---|---|---|---|
| 157 A | O | H | H | F | −74.5(t, 8Hz)/4.2(m, 2H); 3.95(m, 4H) | 87 |
| 158 A | O | CF$_3$ | H | F | −74.2/4.45(m, 2H); 4.2 (m, 1H); 3.95(m, 2H) | 75 |
| 159 A | CH$_2$ | F | F | F | −74.2(CF$_3$); −118(CF$_2$)/ 3.8(m, 2H); 2.4(m, 4H) | 91 |
| 160 A | — | Cl | F | Cl | −68.5(2F); −120(1F) | 60 |

PREPARATION EXAMPLES

Example 1

Method A

1-N-(1-Butylsulfonyl)amino-4-(naphthyl-1-oxy)benzene

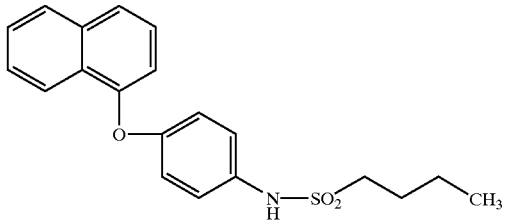

A solution of n-butylsulfonyl chloride (9.5 ml; 72.0 mmol) in dichloromethane (100 ml) is added dropwise under argon at RT to a solution of Example 51 A (17.0 g; 72.3 mmol) in dichloromethane (300 ml) and the mixture is stirred at RT for 1 h. After addition of pyridine (11.7 ml, 140 mmol), the mixture is stirred at RT overnight. The reaction mixture is washed successively with water, 1 N hydrochloric acid (2×), water (2×), dried ($Na_2SO_4$) and concentrated in vacuo. The residue is recrystallized hot from ethanol and then dissolved in dichloromethane. After addition of active carbon, it is filtered, concentrated in vacuo and recrystallized from methanol.

Yield: 12.7 g (49% of theory)

M.p.: 108–109° C.

$R_f$=0.32 (IV)

MS (DCI, $NH_3$): m/e=373 (M+$NH_4$)

Examples 2 and 3
Method B 3-(Naphthyl-1-oxy)-1-N-(1-propylsulfonyl)-aminobenzene (Example 2)

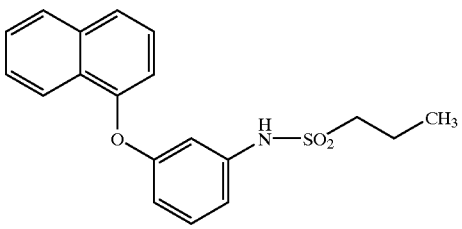

3-(Naphthyl-1-oxy)-1-bis-N-(1-propylsulfonyl)aminobenzene (Example 3)

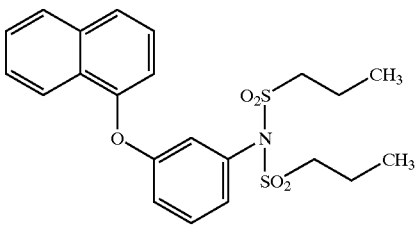

1-Propanesulfonyl chloride (224 mg; 1.57 mmol) and triethylamine (304 mg; 3.00 mmol) are added dropwise at RT under argon to a solution of Example 45 A (353 mg; 1.50 mmol) in dichloromethane (10 ml) and the solution is stirred at RT overnight. After addition of dichloromethane (40 ml), it is washed with water (50 ml), 2 N hydrochloric acid (2×50 ml), 5% strength sulphuric acid (70 ml) and water (50 ml). The organic phase is dried over $Na_2SO_4$ and concentrated in vacuo. The residue is chromatographed on silica gel using dichloromethane:formic acid (200:1).

Yield: (Example 2) 259 mg (51% of theory)
$R_f$=0.40 (XV)
MS (DCI, $NH_3$): m/e=359 (M+$NH_4$)
Yield: (Example 3) 111 mg (16% of theory)
M.p.: 112° C.
$R_f$=0.48 (XV)
MS (DCI, $NH_3$): m/e=465 (M+$NH_4$)

The examples shown in Table 1 are prepared in analogy to the preparation of Example 1 (Method A) and Examples 2 and 3 (Method B):

| | | | | | | | R¹—(CH₂)ₙ—D—(CH₂)ₘ—G—N(R¹⁹)—SO₂—R² | | | | | |
|---|---|---|---|---|---|---|---|---|---|---|---|---|
| Ex.-No. | Method | R¹ | n | D | m | G | R¹⁹ | R² | Yield (% of theory) | M.p. (° C.) | R_f | MS m/e |
| 4 | A | naphthalen-1-yl | 0 | O | 0 | p-phenylene | H | CH₃ | 81 | 138–9 | 0.09 (IV) | 331 (M + NH₄) (B) |
| 5 | A | naphthalen-1-yl | 0 | O | 0 | p-phenylene | H | Et | 66 | 125–6 | 0.13 (IV) | 345 (M + NH₄) (B) |
| 6 | A | naphthalen-1-yl | 0 | O | 0 | p-phenylene | H | nPr | 84 | 150–1 | 0.56 (XVI) | 359 (M + NH₄) (B) |
| 7 | A | naphthalen-2-yl | 0 | O | 0 | p-phenylene | H | nBu | 86 | 108 | 0.35 (IV) | 373 (M + NH₄) (B) |
| 8 | A | 4-chloronaphthalen-1-yl | 0 | O | 0 | p-phenylene | H | nBu | 46 | 107 | 0.40 (IV) | 407 (M + NH₄) (B) |
| 9 | A | 2,3-dimethylphenyl | 0 | O | 0 | p-phenylene | H | nBu | 84 | 105 | 0.43 (IV) | 351 (M + NH₄) (B) |

-continued
| Ex.-No. | Method | R¹ | n | D | m | G | R¹⁹ | R² | Yield (% of theory) | M.p. (° C.) | $R_f$ | MS m/e |
|---|---|---|---|---|---|---|---|---|---|---|---|---|
| 10 | A | 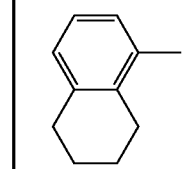 | 0 | O | 0 |  | H | nBu | 66 | 88 | 0.38 (IV) | 377 (M + NH₄) (B) |
| 11 | A | 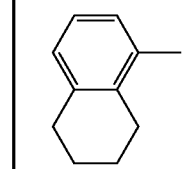 | 0 | O | 0 |  | H | nBu | 75 | 121–2 | 0.87 (XVII) | 423 (M + NH₄) (B) |
| 12 | A | 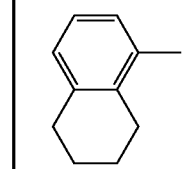 | 0 | O | 0 |  | H | nBu | 44 | 84 | 0.32 (IV) | 375 (M + NH₄) (B) |
| 53 | B | 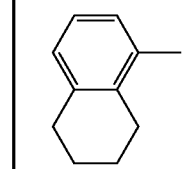 | 0 | O | 0 |  | H | 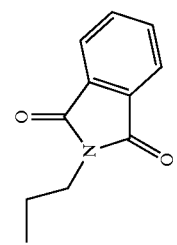 | 52 | 159 | 0.11 (IV) | 490 (M + NH₄) (B) |
| 14 | B | 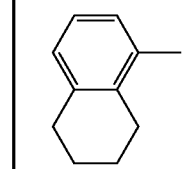 | 0 | O | 0 |  | H | 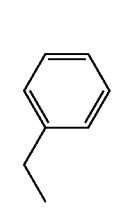 | 37 | 134 | 0.29 (X) | 407 (M + NH₄) (B) |

-continued $$R^1-(CH_2)_n-D-(CH_2)_m-G-N(R^{19})-SO_2-R^2$$

| Ex.-No. | Method | R¹ | n | D | m | G | R¹⁹ | R² | Yield (% of theory) | M.p. (°C.) | $R_f$ | MS m/e |
|---|---|---|---|---|---|---|---|---|---|---|---|---|
| 15 | A | naphthyl | 0 | O | 0 | 2-methyl-5-hydroxyphenyl | H | nBu | 81 | 130 | 0.16 (IV) | 389 (M + NH₄) (B) |
| 16 | A | 1-naphthyl-8-CO₂nBu | 0 | O | 0 | p-tolyl | H | nBu | 85 | 64 | 0.28 (IV) | 473 (M + NH₄) (B) |
| 17 | B | naphthyl | 0 | O | 0 | p-tolyl | H | nOct | 52 | 79 | 0.40 (IV) | 429 (M + NH₄) (B) |
| 18 | A | naphthyl | 1 | O | 0 | p-tolyl | H | nBu | 43 | 120 | 0.31 (IV) | 387 (M + NH₄) (B) |
| 19 | A | 2-naphthyl | 1 | O | 0 | p-tolyl | H | nBu | 49 | 135 | 0.25 (IV) | 387 (M + NH₄) (B) |
| 50 | A | naphthyl | 0 | O | 0 | 2,5-dimethylphenyl | H | nBu | 89 | 89 | 0.29 (IV) | 387 (M + NH₄) (B) |

-continued $$R^1-(CH_2)_n-D-(CH_2)_m-G-N(R^{19})-SO_2-R^2$$

| Ex.-No. | Method | R¹ | n | D | m | G | R¹⁹ | R² | Yield (% of theory) | M.p. (°C.) | R_f | MS m/e |
|---|---|---|---|---|---|---|---|---|---|---|---|---|
| 21 | A | 1-naphthyl | 0 | O | 0 | 1,4-phenylene | H | iPr | 32 | 123 | 0.73 (VII) | 359 (M + NH₄) (B) |
| 22 | B | 1-naphthyl | 0 | O | 0 | 1,4-phenylene | H | –CH=CH–CH₃ (styryl/propenyl phenyl) | 45 | 121 | 0.61 (VI) | 419 (M + NH₄) (B) |
| 23 | B | 1-naphthyl | 0 | O | 0 | 1,4-phenylene | H | –CH₂–CF₃ | 51 | 91 | 0.45 (VI) | 399 (M + NH₄) (B) |
| 24 | A | 1-naphthyl | 0 | O | 0 | 2-methyl-1,4-phenylene | H | nBu | 68 | 107 | 0.42 (IV) | 387 (M + NH₄) (B) |
| 25 | A | 1-naphthyl | 0 | O | 0 | 2-methyl-1,4-phenylene | H | –CH₂CH₂–Ph | 54 | 99–101 | 0.41 (IV) | 421 (M + NH₄) (B) |
| 26 | A | 1-naphthyl | 0 | O | 1 | 1,4-phenylene | H | nBu | 53 | 135 | 0.37 (IV) | 392 (M + Na) (C) |

-continued
$$R^1-(CH_2)_n-D-(CH_2)_m-G-\underset{R^{19}}{N}-SO_2-R^2$$
| Ex.-No. | Method | R¹ | n | D | m | G | R¹⁹ | R² | Yield (% of theory) | M.p. (° C.) | R_f | MS m/e |
|---|---|---|---|---|---|---|---|---|---|---|---|---|
| 57 | A |  | 0 | O | 1 | 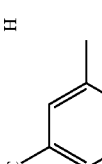 | H | nBu | 39 | — | 0.41 (IV) | 392 (M + Na) (C) |
| 28 | A | 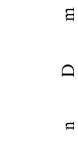 | 0 | O | 0 | 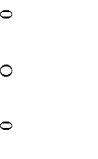 | H |  | 71 | 114 | 0.43 (IV) | 421 (M + NH₄) (B) |
| 29 | B |  | 0 | O | 0 | 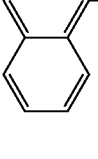 | H | 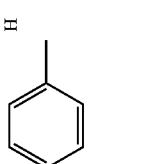 | 75 | 68–70 | 0.58 (VII) | 472 (M + Na) (C) |
| 30 | B |  | 0 | O | 0 |  | H | nPent | 66 | 75 | 0.37 (IV) | 387 (M + NH₄) (B) |
| 31 | B | 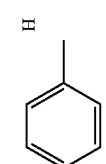 | 0 | O | 0 |  | H | nHex | 62 | 68 | 0.45 (IV) | 401 (M + NH₄) (B) |

-continued $$R^1-(CH_2)_n-D-(CH_2)_m-G-\overset{R^{19}}{N}-SO_2-R^2$$

| Ex.-No. | Method | R¹ | n | D | m | G | R¹⁹ | R² | Yield (% of theory) | M.p. (° C.) | R_f | MS m/e |
|---|---|---|---|---|---|---|---|---|---|---|---|---|
| 32 | A | 1-naphthyl | 0 | O | 0 | 2,5-pyridyl | H | nBu | 83 | 127–28 | 0.73 (VII) | 357 (M + H) (B) |
| 33 | A | 1-naphthyl | 0 | O | 0 | 2,5-pyridyl | H | benzyl | 60 | 161–2 | 0.74 (VII) | 391 (M + H) (B) |
| 54 | A | 1-naphthyl | 0 | O | 0 | 1,3-phenyl | H | nBu | 63 | — | 0.38 (X) | 373 (M + NH₄) (B) |
| 35 | A | 5-isoquinolyl | 0 | O | 0 | 1,4-phenyl | H | nBu | 83 | 103–4 | 0.20 (VII) | 357 (M + H) (B) |
| 36 | B | 1-naphthyl | 0 | O | 0 | 1,4-phenyl | H | 2-nitrophenyl | 72 | 104.5 | 0.51 (XVIII) | 452 (M + NH₄) (B) |
| 37 | B | 1-naphthyl | 0 | O | 0 | 1,4-phenyl | H | 4-chlorophenyl | 60 | 163 | 0.66 (IV) | 441 (M + NH₄) (B) |

-continued
R¹—(CH₂)ₙ—D—(CH₂)ₘ—G—N(R¹⁹)—SO₂—R²
| Ex.-No. | Method | R¹ | n | D | m | G | R¹⁹ | R² | Yield (% of theory) | M.p. (° C.) | Rf | MS m/e |
|---|---|---|---|---|---|---|---|---|---|---|---|---|
| 38 | A | 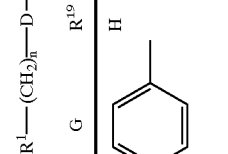 | 0 | O | 0 | 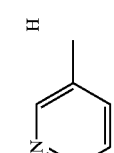 | H | 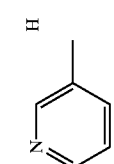 | 70 | 150–1 | 0.27 (VII) | 429 (M + H) (C) |
| 39 | A | 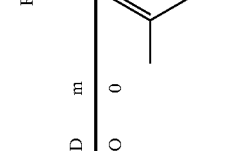 | 0 | O | 0 | 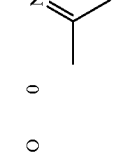 | H | nBu | 81 | 171–3 | 0.70 (XIX) | 358 (M + K) (B) |
| 40 | A | 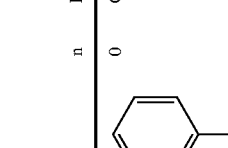 | 0 | O | 0 | 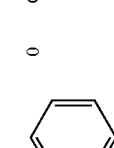 | H | 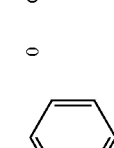 | 63 | 205–7 | 0.70 (XX) | 392 (M + K) (B) |
| 51 | A | 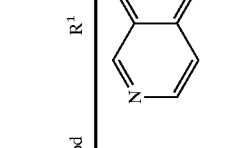 | 0 | O | 0 | 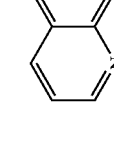 | H | 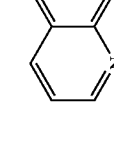 | 81 | 159 | 0.32 (IV) | 452 (M + NH₄) (B) |
| 42 | A | 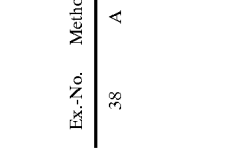 | 0 | O | 0 | 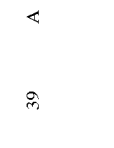 | H | 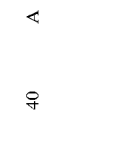 | 38 | 111 | 0.83 (VII) | 385 (M + NH₄) (B) |
| 43 | A |  | 0 | O | 0 |  | H | nBu | 92 | — | 0.32 (IV) | 452 (M + K) (C) |

-continued $$R^1-(CH_2)_n-D-(CH_2)_m-G-\overset{R^{19}}{N}-SO_2-R^2$$

| Ex.-No. | Method | R¹ | n | D | m | G | R¹⁹ | R² | Yield (% of theory) | M.p. (° C.) | R_f | MS m/e |
|---|---|---|---|---|---|---|---|---|---|---|---|---|
| 44 | A | naphthyl | 0 | S | 0 | p-phenylene | H | nBu | 86 | 100 | 0.95 (VII) | 389 (M + NH₄) (B) |
| 45 | A | 1,1-dimethylindanyl | 0 | O | 0 | p-phenylene | H | nBu | 76 | — | 0.80 (X) | 391 (M + NH₄) (B) |
| 46 | B | naphthyl | 0 | O | 0 | p-phenylene | H | 2-chlorophenyl | 59 | 108 | 0.44 (IV) | 462 (M + K) (C) |
| 47 | B | naphthyl | 0 | O | 0 | p-phenylene | H | 3-chlorophenyl | 27 | 146 | 0.41 (IV) | 441 (M + NH₄) (B) |
| 58 | B | naphthyl | 0 | O | 0 | p-phenylene | H | 2-chloro-5-pyridyl | 71 | 141 | 0.12 (IV) | 463 (M + K) (C) |

-continued

| Ex.-No. | Method | R$^1$ | n | D | m | G | R$^{19}$ | R$^2$ | Yield (% of theory) | M.p. (° C.) | R$_f$ | MS m/e |
|---|---|---|---|---|---|---|---|---|---|---|---|---|
| 49 | B | naphthyl | 0 | O | 0 | p-phenylene | H | 4-Br-C$_6$H$_4$-CH$_2$CH$_2$- | 16 | 178 | 0.38 (IV) | 485,487 (M + NH$_4$) (B) |
| 50 | B | naphthyl | 0 | O | 0 | p-phenylene | H | (CH$_3$)$_2$CH-CH$_2$CH$_2$CH$_3$ (sec-pentyl-like) | 56 | 95 | 0.43 (IV) | 374 (M + NH$_4$) (B) |
| 51 | A | naphthyl | 0 | O | 0 | m-phenylene | H | C$_6$H$_5$-CH$_2$CH$_2$- | 77 | 139.5 | 0.28 | 407 (M + NH$_4$) (B) |
| 52 | A | naphthyl | 0 | O | 0 | m-phenylene | H | nPent | 57 | — | 0.30 (X) | 387 (M + NH$_4$) (B) |
| 53 | B | naphthyl | 0 | O | 0 | 2,5-pyridinediyl | H | nPent | 39 | 140 | 0.19 (IV) | 371 (M + H) (B) |
| 54 | B | naphthyl | 0 | O | 0 | 2,5-pyridinediyl | —SO$_2$-Pent | nPent | 20 | 100 | 0.68 (IV) | 505 (M + H) (B) |

-continued
R¹—(CH₂)ₙ—D—(CH₂)ₘ—G—N(R¹⁹)—SO₂—R²
| Ex.-No. | Method | R¹ | n | D | m | G | R¹⁹ | R² | Yield (% of theory) | M.p. (° C.) | R_f | MS m/e |
|---|---|---|---|---|---|---|---|---|---|---|---|---|
| 55 | B | 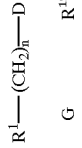 | 0 | O | 0 | 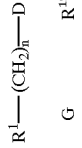 | H | nHex | 56 | — | 0.69 (XXI) | 401 (M + NH₄) (B) |
| 56 | B | 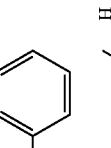 | 0 | O | 0 | 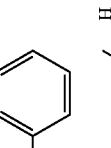 | H | Et | 41 | 108 | 0.48 (XV) | 345 (M + NH₄) (B) |
| 57 | B |  | 0 | O | 0 |  | —SO₂Et | Et | 48 | 55 | 0.82 (XV) | 437 (M + NH₄) (B) |
| 58 | B | 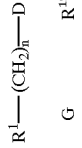 | 0 | O | 0 | 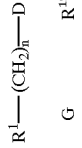 | H | Me | 60 | — | 0.35 | 331 (M + NH₄) (B) |
| 59 | B | 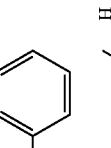 | 0 | O | 0 | 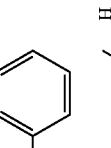 | —SO₂Me | Me | 22 | 145 | 0.69 (XV) | 409 (M + NH₄) (B) |
| 60 | B |  | 0 | O | 0 |  | H | nBu | 31 | — | 0.34 (VI) | 431 (M + NH₄) (B) |

-continued $$R^1-(CH_2)_n-D-(CH_2)_m-G-N(R^{19})-SO_2-R^2$$

| Ex.-No. | Method | R¹ | n | D | m | G | R¹⁹ | R² | Yield (% of theory) | M.p. (° C.) | Rf | MS m/e |
|---|---|---|---|---|---|---|---|---|---|---|---|---|
| 61 | B | 1-naphthyl, 4-CO$_2$CH$_3$ | 0 | O | 0 | 1,4-phenylene | —SO$_2$nBu | nBu | 38 | 114–6 | 0.74 (VI) | 551 (M + NH$_4$) (B) |
| 62 | B | 1-naphthyl | 0 | O | 0 | 1,4-phenylene | H | 4-CH$_3$-phenylethyl | 8 | 165–7 | 0.58 (VI) | 421 (M + NH$_4$) (B) |
| 63 | B | 1-naphthyl | 0 | O | 0 | 1,4-phenylene | H | 3-CH$_3$-phenylethyl | 41 | 141–2 | 0.58 (VI) | 421 (M + NH$_4$) (B) |
| 64 | B | 1-naphthyl | 0 | O | 0 | 1,3-phenylene | H | nOct | 51 | — | 0.64 (XV) | 429 (M + NH$_4$) (B) |
| 65 | A | 1-naphthyl | 0 | O | 0 | 1,4-phenylene | H | Cl-butyl | 58 | 115 | 0.58 (IV) | 393 (M + NH$_4$) (B) |
| 66 | A | 1-naphthyl | 0 | O | 0 | 2,4-dimethylpyridin-3-yl | H | nBu | 89 | — | 0.69 (VII) | 371 (M + H) (B) |

-continued

R¹—(CH₂)ₙ—D—(CH₂)ₘ—G—N(R¹⁹)—SO₂—R²

| Ex.-No. | Method | R¹ | n | D | m | G | R¹⁹ | R² | Yield (% of theory) | M.p. (° C.) | Rf | MS m/e |
|---|---|---|---|---|---|---|---|---|---|---|---|---|
| 67 | A | naphthyl | 0 | O | 0 | 2,5-dimethylpyridin-4-yl (CH₃) | H | benzyl (ethylphenyl) | 69 | 156.5 | 0.71 (VII) | 405 (M + H) (B) |
| 68 | A | naphthyl | 0 | O | 0 | 2-methyl-5-COOCH₃-phenyl | H | benzyl (ethylphenyl) | 79 | — | 0.29 (IV) | 465 (M + NH₄) (B) |
| 69 | A | naphthyl | 0 | NH | 0 | 4-methylphenyl | H | nBu | 83 | 105–7 | 0.42 (VI) | 372 (M + NH₄) (B) |
| 70 | A | naphthyl | 0 | NH | 0 | 4-methylphenyl | H | benzyl (ethylphenyl) | 61 | 100–2 | 0.42 (VI) | 406 (M + NH₄) (B) |
| 71 | A | naphthyl | 0 | O | 0 | 3-methylphenyl | H | 4-Br-ethylphenyl | 43 | — | 0.45 (IV) | 485,487 (M + NH₄) (B) |

Examples 71 and 73

1-N-[1-Methyl)butylsulphonyl]amino-4-(naphthyl-1-oxy)benzene (Example 72)

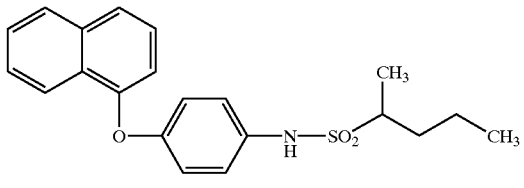

1-N-[1-(1,1-Dimethyl)butylsulphonyl]amino-4-(naphthyl-1-oxy)benzene (Example 73)

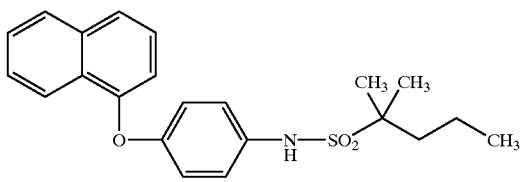

n-Butyllithium, 1.6 N in hexane (1.84 ml; 2.94 mmol), is added dropwise under argon at −70° C. to −78° C. to a solution of Example 1 (500 mg, 1.40 mmol) in THF (15 ml) and the mixture is stirred at −20° C. to −30° C. for 2 h. The reaction mixture is cooled to −70° C. to −78° C. and a solution of iodomethane (199 mg; 1.40 mmol) in THF (5 ml) is added dropwise at this temperature. The mixture is stirred at −70° C. to −78° C. for 1 h and the batch is allowed to warm to RT. After addition of 1 N hydrochloric acid (10 ml), it is diluted with ethyl acetate (30 ml) and shaken. After phase separation, the aqueous phase is extracted with ethyl acetate (2×20 ml). The combined organic phases are washed with 5% strength aqueous sodium thiosulphate solution (2×20 ml) and with water (3×40 ml), dried ($MgSO_4$) and concentrated in vacuo. The residue (442 mg) is dissolved in THF (10 ml) and, after addition of Example 1 (60.0 mg, 0.17 mol), n-butyllithium, 1.6 N in hexane (1.8 ml; 2.94 mmol) is added dropwise at −70° C. to −78° C. under argon. The reaction mixture is then stirred at 0° C. for 2 h, cooled to −70° C. to −78° C. and a solution of iodomethane (199 mg, 1.40 mmol) in THF (5 ml) is added dropwise. After a stirring time of 1 h at −70° C. to −78° C., the batch is warmed to RT and worked up as described above. The crude product (523 mg) consists of a mixture of Examples 72, 73 and 1 in the ratio 66:18:16. The separation of the compounds 72 and 73 from this mixture is carried out by preparative HPLC (column: 250×20 mm packed with Kromasil 100, C-18, 5 μm; flow rate: 15 ml/min; eluent: 25% water, 75% methanol; T=40° C.).

Yield: (Example 72): 222 mg (38% of theory)

Retention time (HPLC): 7.07 min

MS (DCI), $NH_3$): m/e=387 (M+$NH_4$)

Yield: (Example 73): 59 mg (10% of theory)

M.p.: 97–98° C.

Retention time (HPLC): 8.45 min

MS (DCI, $NH_3$): m/e=401 (M+$NH_4$)

Example 74

5-[4-(n-Butylsulphonyl)aminophenyl-1-oxy]-naphthalene-1-carboxylic acid

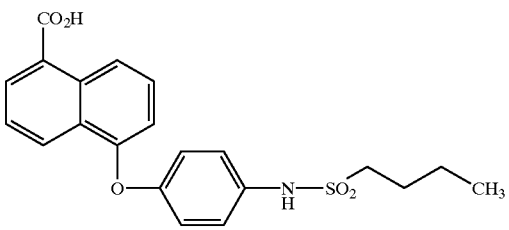

A solution of potassium hydroxide (1.51 g; 27.0 mmol) in water (10 ml) is added dropwise at RT to a solution of Example 16 (4.10 g; 9.0 mmol) in dioxane (20 ml) and the mixture is stirred at RT overnight. After addition of water (100 ml), it is extracted with ethyl acetate (100 ml). The organic phase is discarded and the aqueous phase is adjusted to pH 3 using 2 N hydrochloric acid. Precipitated product is filtered off, washed with water (50 ml) and dried in vacuo.

Yield: 3.16 g (88% of theory)

M.p.: 193° C. $R_f$=0.24 (XXII) MS (DCI, $NH_3$): m/e=417 (M+$NH_4$)

Example 75

5-[N-(n-Butylsulphonyl)amino]-2-(naphthyl-1-oxy)benzoic acid

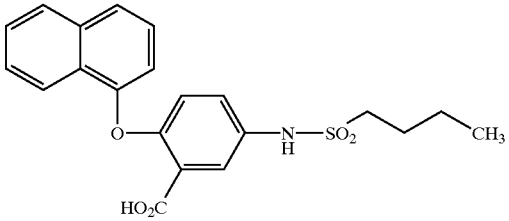

The title compound was prepared in analogy to the preparation of Example 74, starting from Example 43 (3.74 g; 9.4 mmol).

M.p.: 162° C. $R_f$=0.22 (XXII) MS (DCI, $NH_3$): m/e=417 (M+$NH_4$)

Example 76

1-[N-(n-Butylsulphonyl)amino]-2-methoxy-4-(naphthyl-1-oxy)benzene

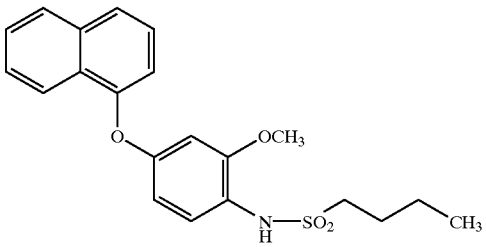

A solution of Example 15 (463 mg; 1.25 mmol) in acetone (10 ml) is treated at RT with $K_2CO_3$ (345 mg; 2.50 mmol)

and after 10 min with iodomethane (177 mg; 1.25 mmol). The reaction mixture is stirred at RT for 48 h and the solvent is then distilled off in vacuo. The residue is taken up in water (50 ml) and extracted with ethyl acetate (3×50 ml). The combined organic phases are dried (Na$_2$SO$_4$) and concentrated in vacuo. The crude product is chromatographed on silica gel using toluene:ethyl acetate (10:1).

Yield: 180 mg (39% of theory)

M.p.: 119° C.

R$_f$=0.35 (IV)

MS (ESI): 424 (M+K)

Example 77

1-[N-(Nonafluorobutylsulphonyl)amino]-4-(naphthyl-1-oxy)benzene

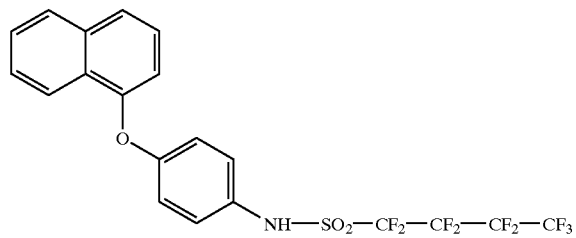

n-Butyllithium, 1.6 N in hexane (3.50 ml, 5.61 mmol) is added dropwise under argon at −70° C. to −75° C. to a solution of the compound from Example 51 A (1.20 g; 5.10 mmol) in THF (20 ml) and the mixture is stirred for 30 min. The resulting reaction mixture is added dropwise at −70° C. to −75° C. to a solution of perfluorobutane-1-sulphofluoride (1.54 g; 5.10 mmol) in THF (20 ml). The batch is allowed to warm to RT, the solvent is stripped off in vacuo, and the residue is taken up in dichloromethane (40 ml). The solution is washed with 1 N hydrochloric acid (2×40 ml), filtered through kieselguhr, washed with water (40 ml) and dried over Na$_2$SO$_4$, and the solvent is stripped off in vacuo. The residue is chromatographed on silica gel using toluene:ethyl acetate (20:1).

Yield: 665 mg (25% of theory)

M.p.: 75° C.

R$_f$=0.38 (X)

MS (FAB): m/e=517 (M)

Example 78

4-(Naphthyl-1-oxy)-1-[N-(2-phenylethylsulphonyl)amino]benzene

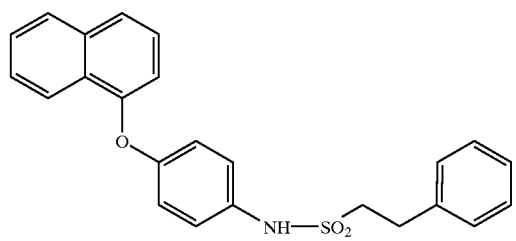

A solution of Example 22 (630 mg; 1.57 mmol) in ethanol (30 ml) and THF (20 ml) is treated with 5% palladium on active carbon (100 mg) and hydrogenated under 3 bar of H$_2$ for 43 h. After filtering off with suction through kieselguhr, the solvent is stripped off in vacuo and the residue is chromatographed on silica gel using petroleum ether:diethyl ether (5:1). A mixture of Examples 22 and 78 is obtained in the ratio 1.3:1 (R$_f$=0.74 (II)), which is taken up in ethanol (20 ml) and hydrogenated again at 40° C. and 3 bar of H$_2$ after addition of 5% palladium on active carbon (100 mg). The reaction mixture is filtered off with suction through kieselguhr, the solvent is stripped off in vacuo, and the residue is recrystallized from methanol.

Yield: 260 mg (41% of theory)

M.p.: 109.5° C.

R$_f$=0.74 (II)

MS (DCI, NH$_3$): m/e=421 (M+NH$_4$)

Example 79

Methyl 5-[4-(n-butylsulphonyl)aminophenyl-1-oxy]-naphthalene-1-carboxylate

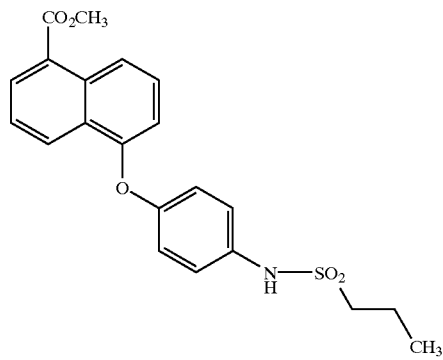

Methanol (0.64 ml; 15.8 mmol), 4-N,N-dimethylaminopyridine (38 mg; 0.32 mmol) and N'-(3-dimethylaminopropyl)-N-ethylcarbodiimide hydrochloride (0.66 g; 3.46 mmol) are successively added at −10° C. to a suspension of the compound from Example 74 (1.25 g; 3.15 mmol) in dichloromethane (14 ml) and the batch is allowed to warm to RT overnight with stirring. After addition of dichloromethane, it is washed with water (50 ml), satd aqueous NaHCO$_3$ solution (2×50 ml) and water 50 ml), dried (Na$_2$SO$_4$) and concentrated in vacuo. The residue is chromatographed on silica gel using toluene:ethyl acetate (10:1).

Yield: 0.94 g (72% of theory)

M.p.: 98° C.

R$_f$=0.23 (IV)

MS (DCI, NH$_3$): m/e=431 (M+NH$_4$)

The examples shown in Table 2 are prepared in analogy to the preparation of Example 79:

TABLE 2

| Ex. No. | $R^{60}$ | Yield (% of theory) | M.p. (° C.) | $R_f$ | MS m/e |
|---|---|---|---|---|---|
| 80 | COOiPr | 21 | 109 | 0.28 (IV) | 459 (M + NH$_4$) (B) |
| 81 | -C(=O)-O-CH$_2$CH$_2$-N(CH$_3$)$_2$ | 56 | 142.5 | 0.27 (XXIV) | 471 (M + H) (B) |
| 82 | -C(=O)-N(piperazinyl)-N-CH$_3$ | 25 | 84 | 0.28 (XXV) | 428 (M + H) (C) |
| 83 | -C(=O)-N(CH$_3$)$_2$ | 25 | 76 | 0.64 (XXV) | 459 (M + Na) (C) |

Example 84

5-[N-(n-Butylsulphonyl)amino]-2-(naphthyl-1-oxy) benzamide

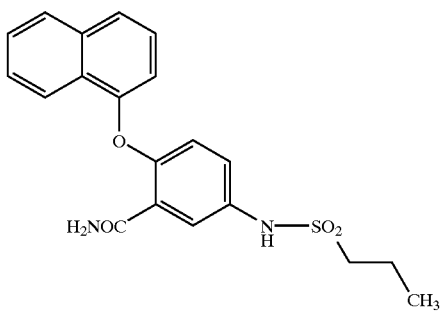

Isobutyl chloroformate (0.40 ml; 3.00 mmol) is added dropwise at −15° C. under argon to a solution of Example 75 (799 mg; 2.00 mmol) and N-methylmorpholine (0.33 ml; 3.00 mmol) in ethyl acetate (10 ml) and the mixture is stirred at −15° C. for 1 h. 25% strength aqueous ammonia solution (0.47 ml; 6.3 mmol) is then added dropwise and the batch is allowed to warm to RT. After addition of ethyl acetate (80 ml) and THF (20 ml), it is washed with 50% strength aqueous Na$_2$CO$_3$ solution (50 ml) and satd NaCl solution (50 ml), dried over Na$_2$SO$_4$ and the solvent is stripped off in vacuo. The residue is stirred with ethyl acetate/diethyl ether (2:1, 6 ml). Precipitated product is filtered off, washed with diethyl ether and dried in vacuo.

Yield: 630 mg (79% of theory)

M.p.: 214° C.

$R_f$=0.11 (XXII)

MS (DCI, NH$_3$): m/e=416 (M+NH$_4$)

The compounds shown in Table 3 are prepared in analogy to the procedure of Example 84:

TABLE 3

| Ex. No. | $R^{61}$ | $R^{62}$ | Yield (% of theory) | M.p. (° C.) | $R_f$ | MS m/e |
|---|---|---|---|---|---|---|
| 85 | CONH$_2$ | H | 32 | 206 | 0.45 (XXII) | 416 (M + NH$_4$) (B) |
| 86 | H | CONHCH$_3$ | 82 | 204 | 0.11 (XXII) | 430 (M + NH$_4$) (B) |

The preparation of the compounds shown in Table 4 is carried out in analogy to the procedure of Example 29 A:

TABLE 4

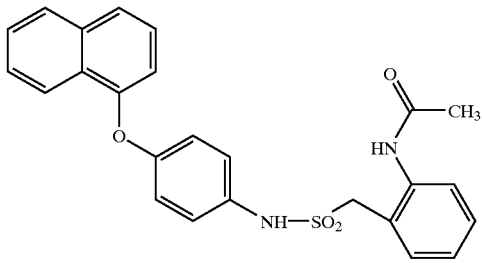

| Ex. No. | Starting material Ex. No. | X | Y | Yield (% of theory) | M.p. (° C.) | $R_f$ | MS m/e |
|---|---|---|---|---|---|---|---|
| 87 | 36 | NH$_2$ | H | 57 | 103.5 | 0.50 (VII) | 405 (M + H) (B) |
| 88 | 41 | H | NH$_2$ | 70 | 182 | — | 405 (M + H) (C) |

Example 89

1-[N-(2-Acetylaminophenylmethylsulphonyl)amino-4-(naphthyl-1-oxy)benzene

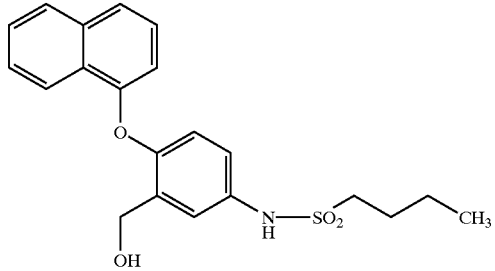

Acetyl chloride (49 mg; 0.62 mmol) is added dropwise to a solution of the compound from Example 87 (250 mg; 0.62 mmol) and triethylamine (125 mg; 1.24 mmol) in dichloromethane (5 ml) and the mixture is stirred at RT for 3 h. The reaction mixture is washed with water (5 ml), 2 N hydrochloric acid (2×5 ml) and water (5 ml), dried (Na$_2$SO$_4$) and concentrated in vacuo. The residue is taken up in THF (8 ml), treated dropwise at 0° C. with a solution of LiOH×H$_2$O (52 mg; 1.24 mmol) and stirred at RT overnight. The THF is stripped off in vacuo and a pH of 2 is set by addition of 1 N hydrochloric acid. The product is extracted with ethyl acetate. The ethyl acetate phases are dried (Na$_2$SO$_4$) and concentrated in vacuo.

Yield: 209 mg (75% of theory)

M.p.: 173.5° C.

$R_f$=0.38 (VII)

MS (DCI, NH$_3$): m/e=464 (M+NH$_4$)

Example 90

1-[N-(3-Acetylaminophenylmethylsulphonyl)amino-4-(naphthyl-1-oxy)benzene

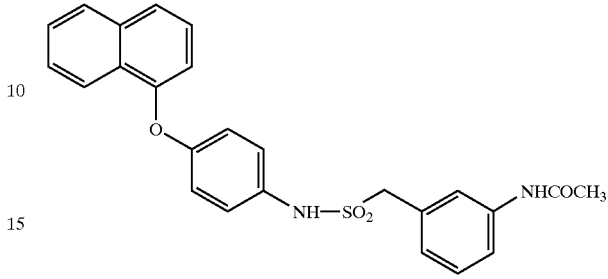

Preparation is carried out in analogy to the preparation of Example 89, starting from Example 88 (500 mg; 1.23 mmol).

Yield: 232 mg (42% of theory)

M.p.: 169° C.

MS (DCI, NH$_3$): m/e=464 (M+NH$_4$)

Example 91

1-[N-(Butylsulphonyl)amino]-3-hydroxymethyl-4-(naphthyl-1-oxy)benzene

A solution of Example 43 (750 mg; 1.81 mmol) in THF (6 ml) is added dropwise under argon at RT to a 1 N solution of lithium aluminium hydride in THF (2.0 ml; 2.0 mmol) and THF (5 ml) and the mixture is stirred at RT overnight. After addition of satd aqueous NH$_4$Cl solution (30 ml), it is extracted with ethyl acetate (3×30 ml). The combined organic phases are dried (Na$_2$SO$_4$) and concentrated in vacuo.

Yield: 698 mg (100%)

$R_f$=0.61 (VII)

MS (DCI, NH$_3$): m/e=403 (M+NH$_4$)

The compounds shown in Table 5 are prepared in analogy to the procedure of Example 91:

TABLE 5

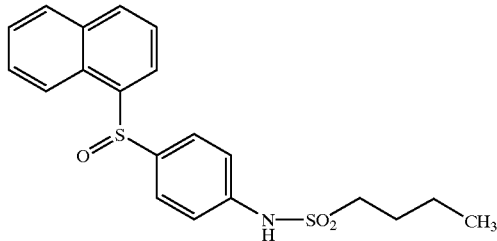

| Ex. No. | $R^{63}$ | $R^{64}$ | Yield (% of theory) | M.p. (° C.) | $R_f$ | MS m/e |
|---|---|---|---|---|---|---|
| 92 | $CH_2OH$ | H | 51 | 200 | 0.06 (IV) | 403 (M + $NH_4$) (B) |
| 93 | H | $CH_2OH$ | 91 | — | 0.13 (VI) | 403 (M + $NH_4$) (B) |

Example 94

1-Naphthyl 4-[N-(n-butylsulphonyl)amino]phenyl sulphoxide

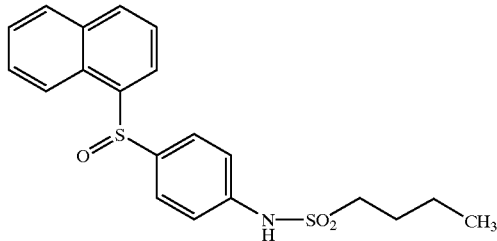

A solution of Example 44 (500 mg; 1.34 mmol) in dichloromethane (15 ml) is treated with m-chloroperbenzoic acid, 80% strength (290 mg; 1.34 mmol) and stirred at RT overnight. The reaction mixture is washed with water (2×20 ml), dried ($Na_2SO_4$) and concentrated in vacuo. The residue is recrystallized from diethyl ether.

Yield: 402 mg (78% of theory)

M.p.: 161° C.

$R_f$=0.40 (VII)

MS (ESI): m/e=426 (M+K)

Example 95

1-Naphthyl 4-[N-(n-butylsulphonyl)amino]phenyl sulphone

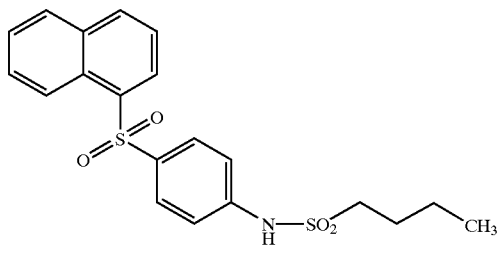

A solution of Example 44 (500 mg; 1.34 mmol) in dichloromethane (15 ml) is treated with m-chloroperbenzoic acid, 80% strength (580 mg; 2.68 mmol) and stirred at RT overnight. After filtration, the filtrate is washed with water (2×15 ml), dried ($Na_2SO_4$) and evaporated in vacuo. The residue is stirred in diethyl ether and then chromatographed on silica gel using toluene:ethyl acetate (8:1).

Yield: 218 mg (40% of theory)

M.p.: 180° C.

$R_f$=0.67 (VII)

MS (ESI): m/e=442 (M+K)

Example 96

1-[N-(n-Butylsulphinylamino)-4-(naphthyl-1-oxy) benzene

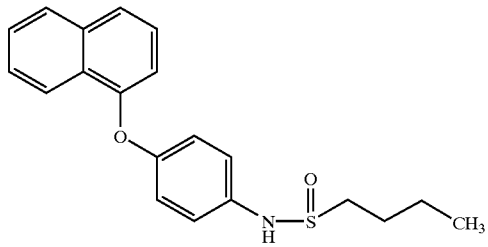

n-Butanesulphinyl chloride (2.20 g; 15.8 mmol; preparation according to JOC, 1968, 33, 2104) is added to a solution of Example 51 A (3.50 g; 15.0 mmol) and pyridine (2.40 g; 30.0 mmol) in dichloromethane and the mixture is stirred at RT overnight. The reaction mixture is introduced into dichloromethane (70 ml) and water (30 ml) and stirred. Precipitated product is filtered off, washed with water and dried.

Yield: 440 mg (9% of theory)

M.p.: 138–139° C.

$R_f$=0.06 (VI)

MS (ESI): m/e=362 (M+Na)

Example 97

1-(n-Butylsulphonyloxy)-4-(naphthyl-1-oxy)benzene

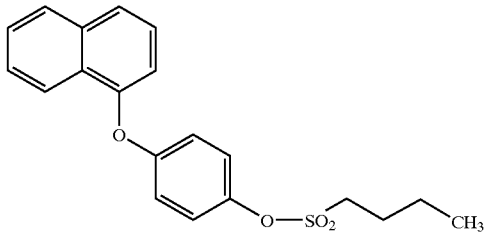

Triethylamine (0.35 ml; 2.54 mmol) and 1-butanesulphonyl chloride (0.18 ml; 1.33 mmol) are added at RT to a solution of Example 56 A (300 mg; 1.27 mmol) in dichloromethane (10 ml) and the mixture is stirred at RT overnight. After addition of dichloromethane (50 ml), it is washed with water (50 ml), 1 N hydrochloric acid (2×50 ml) and water (50 ml), dried over $Na_2SO_4$ and the solvent is stripped off in vacuo. The residue is chromatographed on silica gel using toluene.

Yield: 384 mg (85% of theory)

$R_f$=0.44 (toluene)

MS (DCI, $NH_3$): m/e=374 (M+$NH_4$)

The compounds shown in Table 6 are prepared in analogy to the procedure of Example 97:

TABLE 6

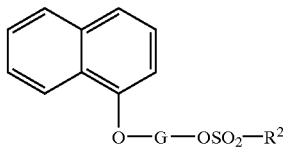

| Ex. No. | G | $R^2$ | Yield (% of theory) | M.p. (° C.) | $R_f$ | MS m/e |
|---|---|---|---|---|---|---|
| 98 | ![2-methyl-4-(NHSO2nBu)phenyl] | nBu | 80 | — | 0.43 (IV) | 509 (M + $NH_4$) (B) |
| 99 | ![1,4-phenylene] | n-Pent | 88 | — | 0.53 (Toluene) | 388 (M + $NH_4$) (B) |
| 100 | ![1,4-phenylene] | ![CH2-phenyl] | 29 | 90 | 0.43 (Toluene) | 408 (M + $NH_4$) (B) |
| 101 | ![2-methyl-1,4-phenylene] H₃C | nBu | 73 | — | 0.83 (IV) | 388 (M + $NH_4$) (B) |
| 102 | ![2-methyl-1,4-phenylene] H₃C | ![CH2-phenyl] | 87 | | 0.82 (IV) | 422 (M + $NH_4$) (B) |

Example 103

1-[N-(1-Propyloxysulphonyl)amino]-4-(naphthyl-1-oxy)benzene

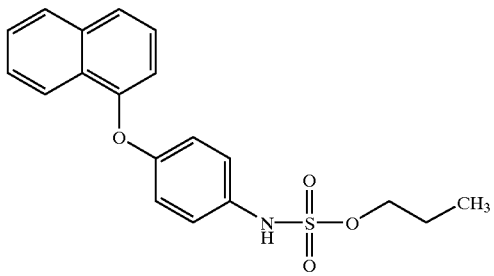

The compound from Example 58 A (3.20 g; 10.0 mmol) is initially introduced into toluene (80 ml). After addition of phosphorus pentachloride (2.08 g; 10.0 mmol), the reaction mixture is slowly heated to reflux temperature in the course of 1 h and stirred under reflux for a further 1.5 h. It is then cooled to RT, and the solution is decanted off from poorly soluble, viscous constituents and concentrated in vacuo. 1.73 g (about 5 mmol) of the resulting aminesulphonyl chloride (about 3.4 g) are taken up in dichloromethane (40 ml) and treated successively with $NA_2CO_3$ (3.0 g), benzyltriethylammonium chloride (228 mg, 1.0 mmol) and 1-propanol (301 mg; 5.0 mmol). The batch is heated to reflux overnight, filtered and concentrated in vacuo. The residue is chromatographed on silica gel using toluene:ethyl acetate (12:1).

Yield: 700 mg (39% of theory)

M.p.: 95° C.

$R_f$=0.40 (IV)

MS (DCI; $NH_3$): m/e=375 (M+$NH_4$)

Example 104

1-[N-(1-Propylaminosulphonyl)amino-4-(naphthyl-1-oxy)benzene

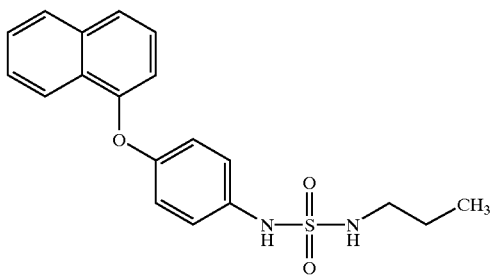

Preparation is carried out in analogy to the synthesis of Example 103, using n-propylamine instead of n-propyl alcohol.

Yield: 280 mg (16% of theory)

M.p.: 113–15° C.

$R_f$=0.38 (IV)

MS (DCI; $NH_3$): m/e=374 (M+$NH_4$)

Example 105

1-(N-1-Butylsulphonyl-N-methyl)amino-4-(naphthyl-1-oxy)benzene

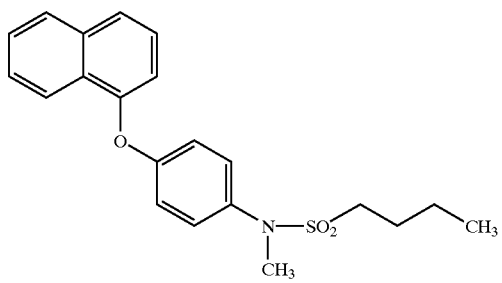

Methyl iodide (0.18 ml; 2,8 mmol) was added to a mixture of 51 A (500 mg; 1.41 mmol) and potassium carbonate (389 mg; 2.81 mmol) in DMF (10 ml). After stirring at RT for 30 min, the reaction solution was added to water and extracted twice with ethyl acetate. The combined organic phases were washed with water, dried over sodium sulphate and concentrated in order to afford 190 mg of a resin which gradually solidified.

Yield: 190 mg (37% of theory)

$R_f$=0.67 (XVI)

MS (DCI, $NH_3$): m/e=387 (M+$NH_4$)

Example 106 and Example 107

1-N-(4-Azido-1-propyl-sulphonyl)amino-4-naphthyl-1-oxy)benzene (Example 106)

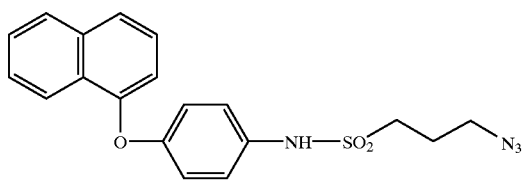

N-(4-Naphthyl-1-oxy)phenyl-1,3-propanesultam
(Example 107)

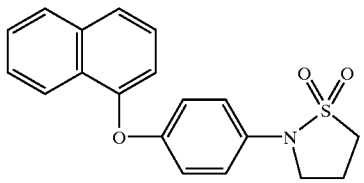

A solution of Example 65 (15.51 g; 41.3 mmol) in DMSO (100 ml) is treated with sodium azide (2.95 g; 45.4 mmol) and heated at 80° C. for 15 h. After addition of water (300 ml), it is extracted with diethyl ether (3×200 ml). The combined organic phases are washed with saturated NaCl solution (200 ml), dried (Na$_2$SO$_4$) and concentrated in vacuo. The residue is chromatographed on silica gel using toluene:diethyl ether (10:1).

Yield: (Example 106): 9.80 g (62% of theory)
M.p.: 77.5° C.
R$_f$=0.29 (IV)
MS (DCI, NH$_3$): m/e=400 [M+NH$_4$]
Yield: (Example 107) 1.61 g (12% of theory)
M.p.: 150° C.
R$_f$=0.21 (IV)
MS (DCI, NH$_3$): m/e=357 [M+NH$_4$]

Example 108

1-N-(4-Amino-1-propylsulphonyl)amino-4-(naphthyl-1-oxy)benzene

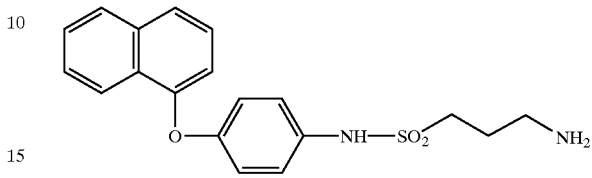

A solution of Example 106 (4.76 g; 12.4 mmol) in methanol (100 ml) is treated with 10% palladium on active carbon (0.5 g) and hydrogenated at 3 bar and room temperature for 3.5 h. The reaction mixture is filtered through kieselgur and concentrated in vacuo.

Yield: 3.67 g (83% of theory)
M.p.: 159° C.
R$_f$=0.08 (XXIII)
MS (DCI, NH$_3$): m/e=357 [M+H]

The examples listed in Table 7 are prepared in analogy to the preparation of Examples 1 to 71 (Methods A and B):

TABLE 7
R¹—(CH₂)ₙ—D—(CH₂)ₘ—G—N(R¹⁹)—SO₂R²
| Ex. No. | Method | R¹ | n | D | m | G | R¹⁹ | R² | Yield (% of theory) | M.p. (°C.) | R_f | MS (m/e) |
|---|---|---|---|---|---|---|---|---|---|---|---|---|
| 109 | B | 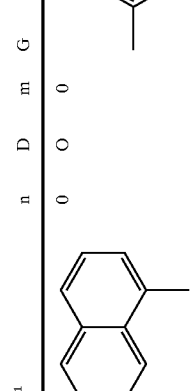 | 0 | 0 | 0 | 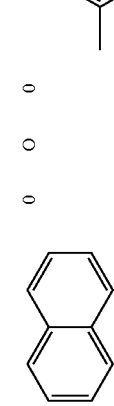 | H | nBu | 34 | 140 | 0.40 (XVI) | 357 (M+H)(C) |
| 110 | B | 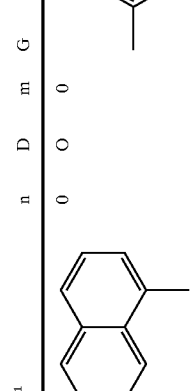 | 0 | 0 | 0 | 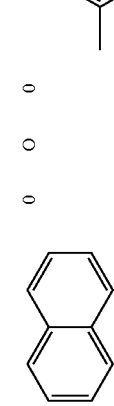 | H | nPent | 34 | 119 | 0.42 (XVI) | 371 (M+H)(C) |
| 111 | B | 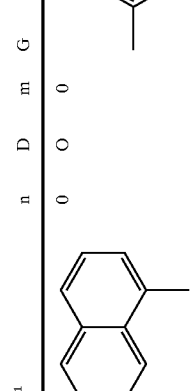 | 0 | 0 | 0 | 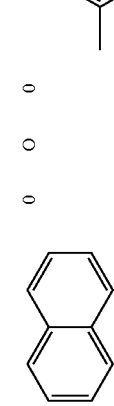 | H | 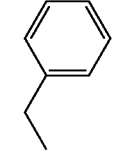 | 39 | 179 | 0.39 (XVI) | 391 (M+H)(C) |
| 112 | A | 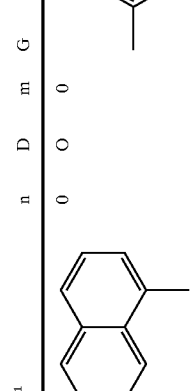 | 0 | 0 | 0 | 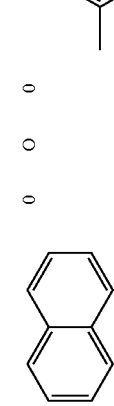 | H | nBu | 20 | — | 0.51 (XVI) | 357 (M+H)(B) |
| 113 | A | 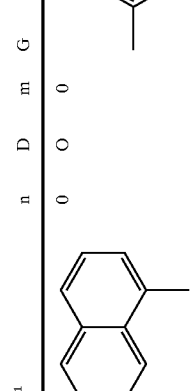 | 0 | 0 | 0 | 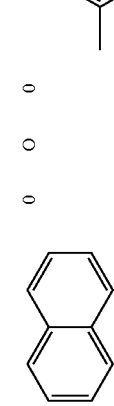 | H | nBu | 85 | 87–88 | 0.37 (CH₂Cl₂) | 441 (M+NH₄)(B) |

TABLE 7-continued $$R^1-(CH_2)_n-D-(CH_2)_m-G-\underset{\underset{R^{19}}{|}}{N}-SO_2R^2$$

| Ex. No. | Method | R¹ | n | D | m | G | R¹⁹ | R² | Yield (% of theory) | M.p. (°C.) | Rf | MS (m/e) |
|---|---|---|---|---|---|---|---|---|---|---|---|---|
| 114 | A | 1-naphthyl | 0 | 0 | 0 | 2,5-dimethyl-3-(CF₃)phenyl | H | CH₂CH₂-phenyl | 88 | — | 0.38 (CH₂Cl₂) | 475 (M + NH₄) (B) |
| 115 | A | 1-naphthyl | 0 | 0 | 0 | 2-CF₃-4-methylphenyl | H | nBu | 19 | 83–85 | 0.60 (CH₂Cl₂) | 441 (M + NH₄) (B) |
| 116 | A | 1-naphthyl | 0 | 0 | 0 | 3,5-dimethylphenyl | H | CH₂CH₂CH₂CF₃ | 58 | — | 0.42 (CH₂Cl₂) | 427 (M + NH₄) (B) |
| 117 | A | 1-naphthyl | 0 | 0 | 0 | 4-methylphenyl | H | CH₂CH₂CH₂CF₃ | 78 | 106–7 | 0.53 (XV) | 427 (M + NH₄) (B) |
| 118 | A | 1-naphthyl | 0 | 0 | 0 | 2-chloro-4,6-dimethylpyridyl | H | CH₂CH₂-phenyl | 44 | 77 | 0.65 (XVI) | 425 (M + H) (C) |

TABLE 7-continued
$$R^1-(CH_2)_n-D-(CH_2)_m-G-\overset{R^{19}}{\underset{|}{N}}-SO_2R^2$$
| Ex. No. | Method | R¹ | n | D | m | G | R¹⁹ | R² | Yield (% of theory) | M.p. (°C.) | R_f | MS (m/e) |
|---|---|---|---|---|---|---|---|---|---|---|---|---|
| 119 | A | 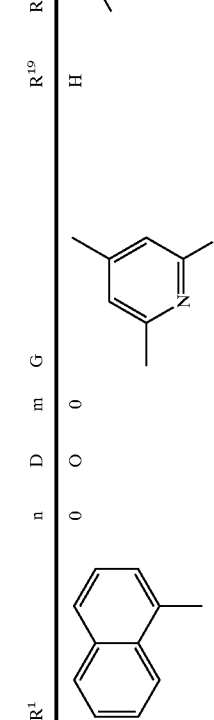 | 0 | O | 0 |  | H | 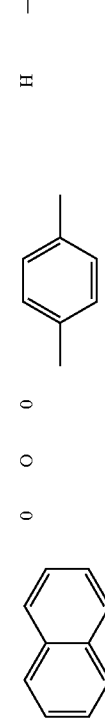 | 33 | 80 | 0.74 (XVI) | 533 (M + H) (C) |
| 120 | A | 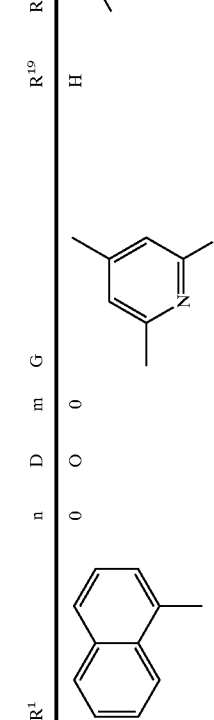 | 0 | O | 0 |  | H | —CH₂CH₂—O—CH₂CF₃ | 81 | 85 | 0.47 (XV) | 443 (M + NH₄) (B) |
| 121 | A | 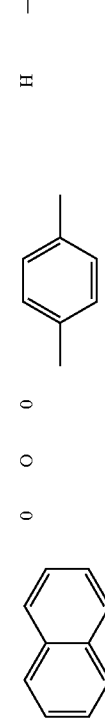 | 0 | O | 0 | 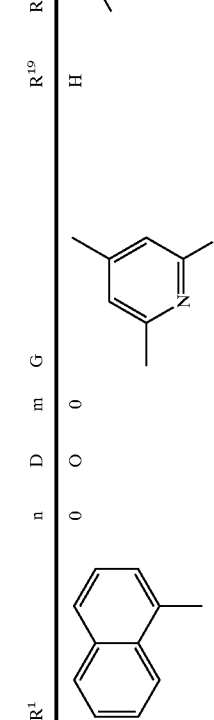 | H | —CH₂CH₂—O—CH₂CF₃ | 60 | — | 0.25 (IV) | 443 (M + NH₄) (B) |
| 122 | A |  | 0 | O | 0 | 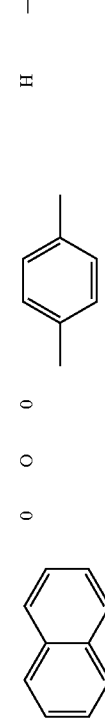 | H | 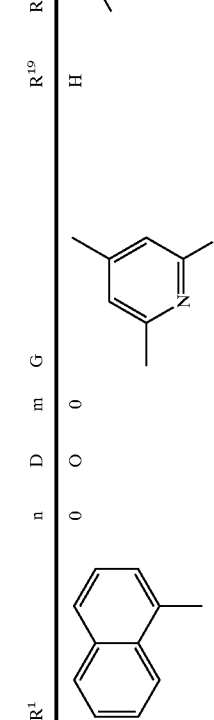 | 54 | 164–6 | 0.45 (XVI) | 425 (M + H) (C) |

TABLE 7-continued
$$R^1\text{—}(CH_2)_n\text{—}D\text{—}(CH_2)_m\text{—}G\text{—}\underset{\underset{R^{19}}{|}}{N}\text{—}SO_2R^2$$
| Ex. No. | Method | R¹ | n | D | m | G | R¹⁹ | R² | Yield (% of theory) | M.p. (°C.) | $R_f$ | MS (m/e) |
|---|---|---|---|---|---|---|---|---|---|---|---|---|
| 123 | A | 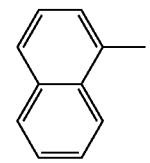 | 0 | O | 0 |  | H | nBu | 68 | 166–8 | 0.50 (VII) | 357 (M + H) (C) |
| 124 | A | 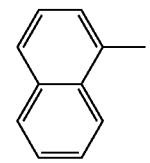 | 0 | O | 0 |  | H |  | 29 | 235–7 | 0.50 (VII) | 391 (M + H) (C) |
| 125 | A | 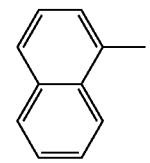 | 0 | O | 0 |  | H | nPent | 74 | 150–2 | 0.54 (VII) | 371 (M + H) (B) |

Example 126

1-(Benzylsulphonyloxy)-3-(naphthyl-1-oxy)benzene

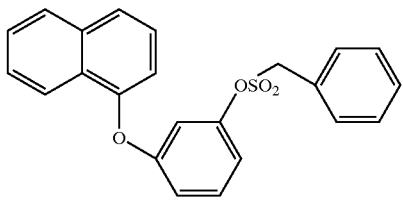

Preparation was carried out in analogy to the preparation of Example 97, starting from Example 63 A (0.709 g; 3.00 mmol).

Yield: 0.680 g (58% of theory)
$R_f$=0.50 (toluene)
MS (DCI, $NH_3$): m/e=408 (M+$NH_4$)

Example 127

3-(Naphthyl-1-oxy)-1-(pentylsulphonyloxy)benzene

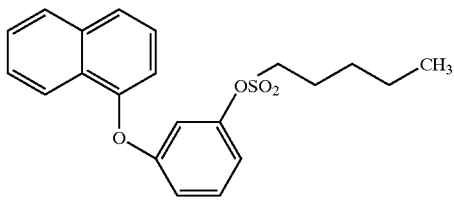

Preparation was carried out in analogy to the preparation of Example 97, starting from Example 63 A (0.709 g; 3.00 mmol).

Yield: 0.800 g (72% of theory)
$R_f$=0.52 (toluene)
MS (DCI, $NH_3$): m/e=388 (M+$NH_4$)

Example 128

2-(Naphthyl-1-oxy)-4-(pentylsulphonylamino)pyridine sodium salt

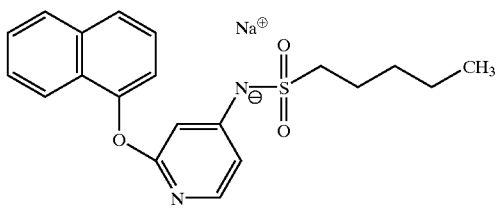

A solution of Example 110 (0.227 g; 0.61 mmol) in tetrahydrofuran (2 ml) is treated at room temperature under argon with a solution of sodium methoxide (0.033 g; 0.61 mmol) in MeOH (1.56 ml). The reaction mixture is stirred for a further 15 min and the solvents are then stripped off in vacuo. The residue is stirred in diethyl ether, filtered off and dried in vacuo.

Yield: 0.240 g (99% of theory)
$R_f$=168° C. (dec.)

The preparation of the compounds listed in Table 8 is carried out in analogy to the procedure of Example 128.

TABLE 8

| Ex. | G | $R^2$ | Yield (% of theory) | M.p. (° C.) |
|---|---|---|---|---|
| 129 | 4-methyl-2-pyridyl | n-Bu | 99 | 165 (D.) |
| 130 | 4-methyl-2-pyridyl | benzyl | 96 | 170 (D.) |
| 131 | 4-methyl-3-trifluoromethyl-phenyl | benzyl | 64 | 118 (D.) |
| 132 | 4,5-dimethyl-2-pyridyl | benzyl | 98 | 72 (D.) |
| 133 | 2,5-pyridyl | nBu | 93 | 160 (d.) |
| 134 | 2,5-pyridyl | benzyl | 89 | 180 (d.) |
| 135 | 2,5-pyridyl | nPent | 91 | 210 (d.) |

Example 136

1-(Naphthyl-1-oxy)-4-(3-pyridylmethylsulphonylamino)benzene

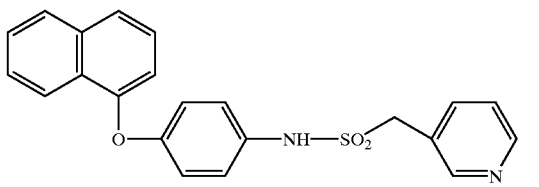

A solution of Example 48 (2.1 g; 5.0 mmol) in THF (40 ml) and methanol (100 ml) is treated with palladium, 10% on active carbon (0.5 g) and hydrogenated for 15 h at 3 bar. The reaction mixture is filtered through kieselgur and the filtrate is concentrated in vacuo.

The residue is chromatographed on silica gel using toluene:ethyl acetate (2:1).

Yield: 0.668 g (34% of theory)

M.p.: 174–76° C.

$R_f$=0.13 (XXVII)

MS (ESI): m/e=391 (M+H)

Example 137

1-(Naphthyl-1-oxy)-3-(3-pyridylmethylsulphonylamino)benzene

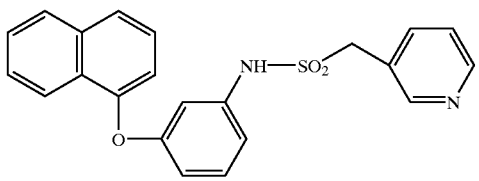

Preparation was carried in analogy to the preparation of Example 136, starting from Example 118 (1.83 g; 4.2 mmol).

Yield: 1.43 g (85% of theory)

$R_f$=0.09 (XVI)

MS (ESI): m/e=391 (M+H)

Example 138

4-(n-Butylsulphonylamino)-2-(N,N-dimethylamino)methyl-1-(naphthyl-1-oxy)benzene

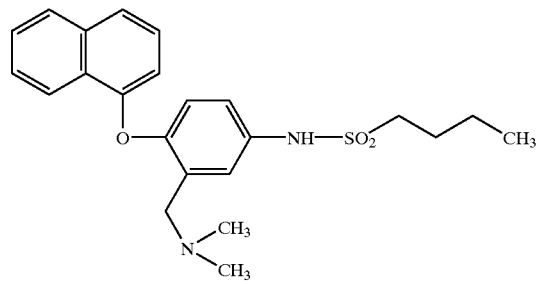

A solution of Example 83 (0.200 g; 0.469 mmol) in THF (5 ml) is treated at room temperature under argon with a 1 N solution of LiAlH$_4$ in THF (0.94 ml; 0.94 mmol) and heated to reflux for 18 h.

After addition of water (20 ml), the reaction mixture is extracted with ethyl acetate (3×20 ml). The combined organic phases are dried (Na$_2$SO$_4$) and concentrated in vacuo.

Yield: 0.190 g (98% of theory)

$R_f$=0.77 (XXVI)

MS (DCI, NH$_3$): m/e=413 (M+H)

The examples listed in Table 9 are prepared in analogy to the preparation of Example 138.

TABLE 9

| Ex No | $R^{47}$ | Yield (% of theory) | M.p (° C.) | $R_f$ | MS [m/e] |
|---|---|---|---|---|---|
| 139 | —CH$_2$—N(piperazine)NCH$_3$ | 97 | | 0.60 (XXVI) | 468 (M + H) (B) |
| 140 | —CH$_2$NHCH$_3$ × HCl[a] | 12 | 120 (D) | 0.40 (XXVI) | 399 (M + H) (B) |

[a] Subsequent conversion into the hydrochloride using a saturated solution of HCl in ether

Example 141

1-[3-(N,N-Dimethylamino]propylsulphonyl)amino-
4-(naphthyl-1-oxy)benzene

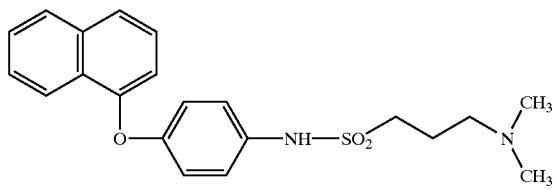

A solution of Example 108 (0.505 g; 1.40 mmol), zinc(II) chloride (0.772 g; 5.70 mmol) and para-formaldehyde (0.170 g; 5.70 mmol) in dichloromethane (25 ml) is stirred at room temperature under argon for 1 h, then treated with sodium borohydride (0.214 g; 5.70 mmol) and stirred at room temperature overnight.

After addition of an aqueous 2.6 N ammonia solution (8.6 ml), the mixture is diluted with water (50 ml) and extracted twice with CH$_2$Cl$_2$ (50 ml). The combined organic phases are dried (Na$_2$SO$_4$) and concentrated in vacuo. The residue is chromatographed on silica gel using dichloromethane:ethanol (5:1).

Yield: 0.107 g (20% of theory)
R$_f$=0.60 (XXVI)

MS (DCI, NH$_3$): m/e=385 (M+H)

Example 142

3-[(4-Naphthyl-1-oxy)-phenyl)aminosulphonyl]
propyl-N,N,N-trimethylammonium iodide

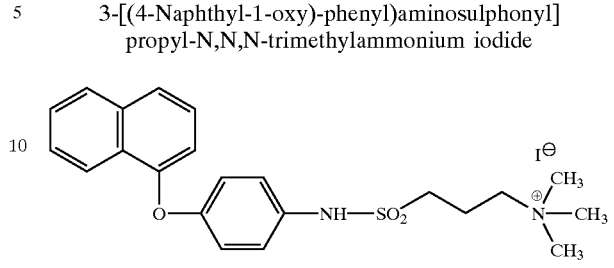

A solution of Example 108 (1.07 g; 3.00 mmol) in THF (50 ml) is treated at room temperature with iodomethane (0.43 g; 3.00 mmol) and stirred at room temperature for 72 h. Precipitated product is filtered off and dried in vacuo.

Yield: 0.341 g (22% of theory)

M.p.: >210° C. (D.)

MS (DCI, NH$_3$): m/e=399 (M+H)

The examples shown in Table 10 are prepared in analogy to the preparation of Examples 1 (Method A) and 2 (Method B).

TABLE 10

$R^1$—O—G—NH—SO$_2$—$R^2$

| Ex. No. | Method | $R^1$ | G | $R^2$ | Yield (% of theory) | M.p. (° C.) | R$_f$ | MS m/e |
|---|---|---|---|---|---|---|---|---|
| 143 | A | CH$_3$O$_2$C-(3-methylphenyl) | 1,4-phenylene | nBu | 72 | 89–90 | 0.25 (VI) | 386 (M + H) (C) |
| 144 | A | 2-biphenyl | 1,4-phenylene | nBu | 67 | 118–9 | 0.41 (VI) | 404 (M + Na) (C) |
| 145 | A | 4-tert-butylphenyl | 1,4-phenylene | nBu | 88 | 84–5 | 0.39 (VI) | 384 (M + Na) (C) |

TABLE 10-continued
R¹—O—G—NH—SO₂—R²
| Ex. No. | Method | R¹ | G | R² | Yield (% of theory) | M.p. (° C.) | R$_f$ | MS m/e |
|---|---|---|---|---|---|---|---|---|
| 146 | A | 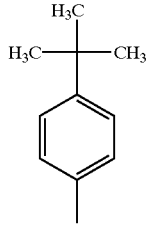 |  | 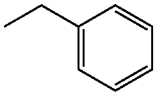 | 80 | 129–30 | 0.40 (VI) | 418 (M + Na) (C) |
| 147 | A | 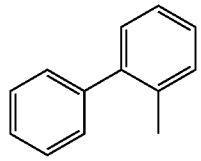 |  | 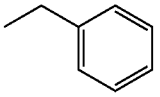 | 97 | 133–4 | 0.43 (VI) | 438 (M + Na) (C) |
| 148 | A | 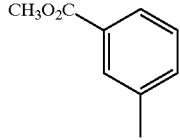 | 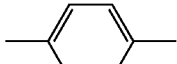 | 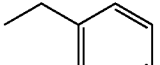 | 54 | 76–8 | 0.31 (VI) | 420 (M + Na) (C) |
| 149 | A | 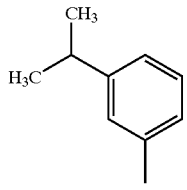 | 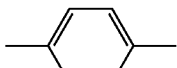 | 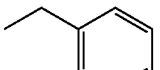 | 80 | 82–5 | 0.46 (VI) | 404 (M + Na) (C) |
| 150 | A | 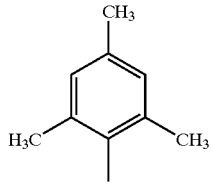 | 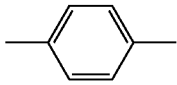 | nBu | 42 | 121–3 | 0.50 (VI) | 370 (M + Na) (C) |
| 151 | A | 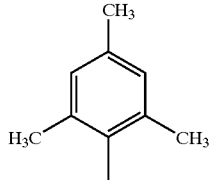 | 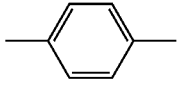 | 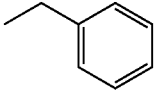 | 52 | 124–6 | 0.51 (VI) | 404 (M + Na) (C) |
| 152 | A | 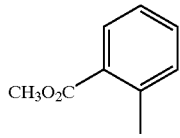 | 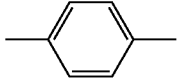 | nBu | 42 | 71–3 | 0.31 (VI) | 386 (M + Na) (C) |
| 153 | A | 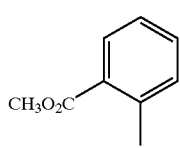 | 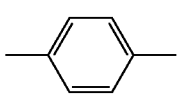 | 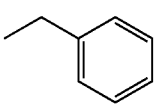 | 69 | 109–12 | 0.30 (VI) | 420 (M + Na) (C) |

TABLE 10-continued

R¹—O—G—NH—SO₂—R²

| Ex. No. | Method | R¹ | G | R² | Yield (% of theory) | M.p. (° C.) | $R_f$ | MS m/e |
|---|---|---|---|---|---|---|---|---|
| 154 | A | 3-isopropylphenyl | 1,4-phenylene | nBu | 71 | 47–8 | 0.41 (VI) | 370 (M + Na) (C) |
| 155 | A | 3-methylphenyl | 1,4-phenylene | nBu | 91 | 75–6 | 0.41 (VI) | 342 (M + Na) (C) |
| 156 | A | 3-methylphenyl | 1,4-phenylene | benzyl | 84 | 115–6 | 0.39 (VI) | 376 (M + Na) (C) |
| 157 | A | 2,6-dimethylphenyl | 1,4-phenylene | nBu | 87 | 107–8 | 0.44 (VI) | 356 (M + Na) (C) |
| 158 | A | 2,6-dimethylphenyl | 1,4-phenylene | benzyl | 82 | 110–1 | 0.39 (VI) | 390 (M + Na) (C) |
| 159 | A | 3-biphenyl | 1,4-phenylene | benzyl | 65 | 157.5–8.5 | 0.38 (VI) | 438 (M + Na) (C) |
| 160 | A | 3-biphenyl | 1,4-phenylene | nBu | 59 | 157–9 | 0.48 (VI) | 404 (M + Na) (C) |
| 161 | A | 3-tert-butylphenyl | 1,4-phenylene | benzyl | 82 | 105–6 | 0.52 (VI) | 394 (M − H) (C) |

TABLE 10-continued
R¹—O—G—NH—SO₂—R²
| Ex. No. | Method | R¹ | G | R² | Yield (% of theory) | M.p. (° C.) | $R_f$ | MS m/e |
|---|---|---|---|---|---|---|---|---|
| 162 | A | 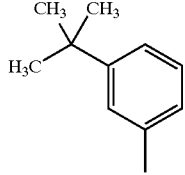 |  | nBu | 90 | 85–7 | 0.50 (VI) | 360 (M − H) (C) |
| 163 | A | 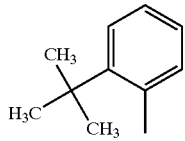 |  | 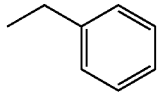 | 86 | 97.5–9 | 0.52 (V) | 394 (M − H) (C) |
| 164 | A | 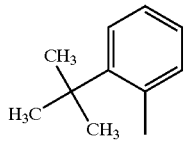 |  | nBu | 76 | 75–6 | 0.48 (VI) | 360 (M − H) (C) |
| 165 | B | 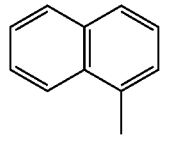 | 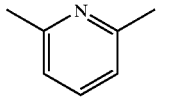 | 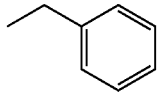 | 8.3 | 151 | 0.16 (XXVIII) | 391 (M + H) (C) |
| 166 | B | 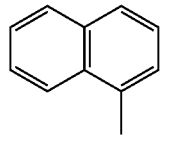 | 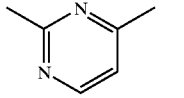 | 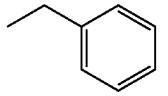 | 5.2 | 154–5 | 0.51 (VII) | 392 (M + H) (B) |
| 167 | B | 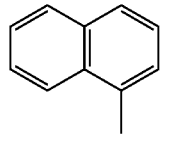 | 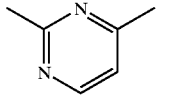 | nBu | 16 | 141–2 | 0.54 (VII) | 358 (M + H) (C) |
| 168 | A | 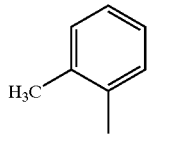 |  | nBu | 82 | 63–4 | 0.44 (VI) | 318 (M − H) (C) |
| 169 | A | 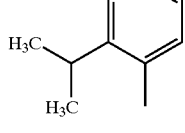 |  | nBu | 96 | — | 0.44 (VI) | 346 (M − H) (C) |
| 170 | A | 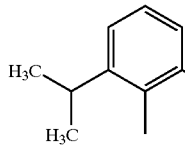 |  | nBu | 42 | 96–7 | 0.47 (VI) | 388 (M − H) (C) |

TABLE 10-continued

R¹—O—G—NH—SO₂—R²

| Ex. No. | Method | R¹ | G | R² | Yield (% of theory) | M.p. (° C.) | $R_f$ | MS m/e |
|---|---|---|---|---|---|---|---|---|
| 171 | A | 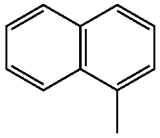 | 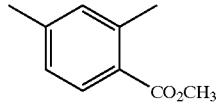 | nBu | 25 | — | 0.26 (XXX) | 431 (M + NH₄) (B) |

Examples 172 and 173

2-N-(n-Butylsulphonyl)amino-4-(naphthyl-1-oxy)benzoic acid (Example 172)

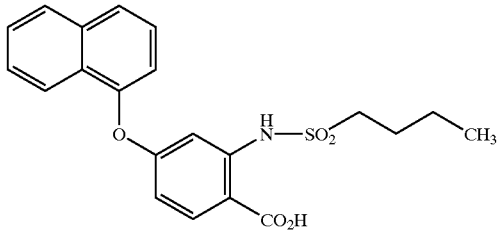

n-Propyl 2-N-(n-butylsulphonyl)amino-4-(naphthyl-1-oxy)benzoate (Example 173)

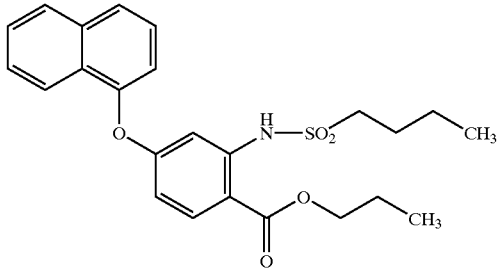

A solution of Example 172 (0.500 g; 1.21 mmol) in 6 ml of n-propanol was treated with 1 N sodium hydroxide solution (2.50 ml) and stirred at 85° C. overnight. The reaction mixture was poured onto water, extracted three times with ethyl acetate, rendered acetic and extracted again with ethyl acetate. All ethyl acetate phases were combined, concentrated in vacuo and chromatographed on silica gel.

Ex. No. 172: Yield: 0.213 g (42% of theory)

M.P.: 145–146° C. $R_f$=0.35 (XXV) MS (ESI): m/e=400 (N+H)

Ex. No. 173: Yield: 0.195 g (36.5% of theory) Yellow oil $R_f$=0.63 (IV) MS (ESI): m/e=364 (M+Na)

Example 174

Sodium salt of 4-N-(n-butylsulphonyl)amino-2-(naphthyl-1-oxy)pyrimidine

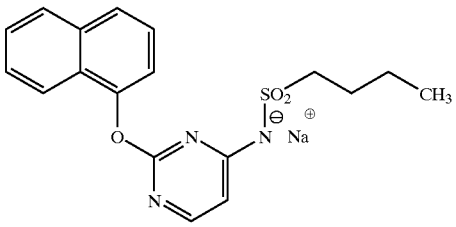

Example 167 (0.310 g; 0.84 mmol) was dissolved in THF (2 ml) and treated with 1 N sodium hydroxide solution (0.84 ml). The THF was stripped off in vacuo and the resulting solution was lyophilized.

Yield: 0.317 g of white powder (100% of theory)

$R_f$=0.47 (VII)

Example 175

Sodium salt of methyl 2-N-(benzylsulphonyl)amino-4-(naphthyl-1-oxy)benzoate

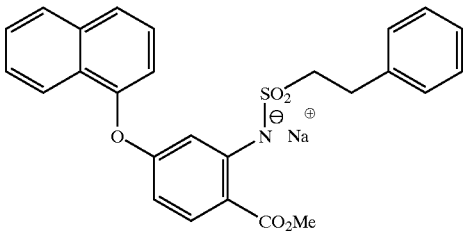

In analogy to the preparation of Example 1, methyl 2-n-(benzylsulphonyl)amino-4-(naphthyl-1-oxy)benzoate was prepared from Example 82 A (0.590 g; 2.01 mmol). The chromatographed product (0.274 g) was dissolved in THF (3 ml) and treated with sodium methoxide (0.033 g; 0.61 mmol). The suspension was dissolved completely by addition of methanol (5 ml), the solution was concentrated, and the solid residue was digested with a little methanol and filtered off.

Yield: 0.186 g of white solid (20% of theory)

$R_f$=0.67 (IV)

MS (corresponding acid, DCI/NH₃): m/e=465 (M+Na)

Example 176

1-(Naphthyl-1-oxy)-4-N-(n-pentanoyl)aminobenzene

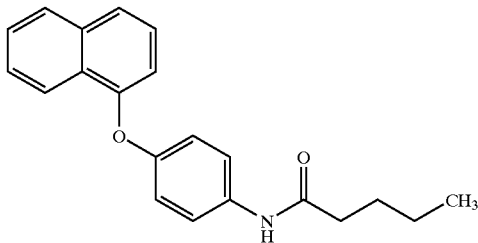

Pyridine (1.0 ml, 3 mmol) was added to a solution of Example 51 A (2.0 g; 8.5 mmol) and valeryl chloride (1.0 ml; 8.5 mmol) in methylene chloride (20 ml) and the mixture was stirred at room temperature overnight. The reaction solution was poured onto water and extracted (2×) with methylene chloride. The organic phases were washed (2×) with water, dried over $Na_2SO_4$ and concentrated. The resultant solid was stirred with ether, filtered off and dried.

Yield: 2.37 g (87% of theory)

M.p.: 80° C.

$R_f$=0.57 (XVI)

MS ($DCI/NH_3$): m/e=320 (M+H)

The examples shown in Table 11 were prepared in analogy to Example 176.

TABLE 11

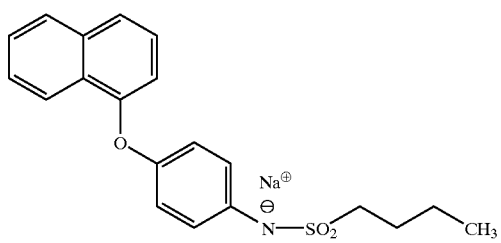

| Ex.-No. | $R^2$ | Yield (%) | M.p. (° C.) | $R_f$ | MS (m/e) |
|---|---|---|---|---|---|
| 177 | cyclohexyl | 64 | 163 | 0.30 (IV) | 346 (M + H) (B) |
| 178 | 2-furyl | 82 | 134 | 0.25 (IV) | 330 (M + H) (B) |
| 179 | —$CH_2$—O—$CH_3$ | 63 | 85 | 0.12 (IV) | 308 (M + H) (B) |

Example 180

1-(Naphthyl-1-oxy)-4-N-(phenylsulphonyl)aminobenzene

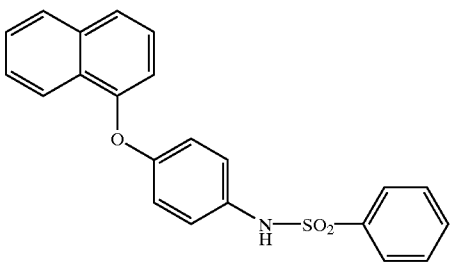

In analogy to the preparation of Example 1, Example 180 was prepared from Example 51 A (2.0 g; 8.5 mmol).

Yield: 2.35 g (74% of theory)

M.p.: 143–4° C.

$R_f$=0.25 (IV)

MS ($DCI/NH_3$): m/e=393 (M+$NH_4$)

Example 181

1-N-(1-Butylsulphonyl)amino-4-(naphthyl-1-oxy)benzene sodium salt

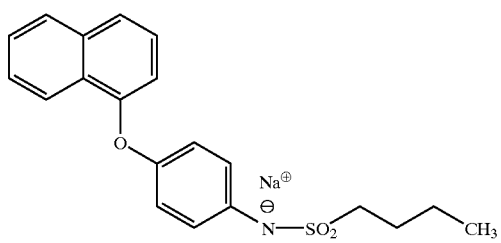

Preparation was carried out in analogy to the preparation of Example 128, starting from Example 1 (0.500 g; 1.41 mmol).

Yield: 0.479 g (91% of theory)

M.p.: >210° C.

$R_f$=0.32 (IV, corresponding acid)

MS (corresponding acid DCI, $NH_3$): m/e=373 (M+$NH_4$)

Example 182

5-(N-Butylsulphonyl)amino-2-(1-naphthyl-1-oxy)pyridine hydrochloride

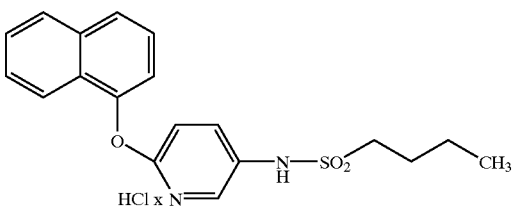

A solution of Example 32 (0.500 g; 1.40 mmol) in THF (10 ml) is treated with a 2.6 N solution of HCl in diethyl ether (0.77 ml; 2.0 mmol), stirred for 10 minutes and concentrated in vacuo until the product begins to precipitate After addition of. diethyl ether, the product is filtered off and dried in vacuo.

Yield: 0.550 g (100% of theory)

M.p.: 136–38° C.

Example 183

Methyl n-butanephosphonate N-(4-(naphthyl-1-oxy) phenyl)amide

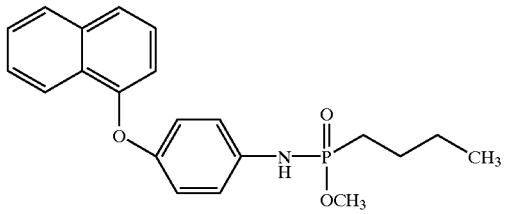

A solution of methanol (0.365 g; 11.4 mmol) in toluene (10 ml) is added dropwise under argon at 0 to 5° C. to a solution of n-butanephosphonyl dichloride (2.00 g, 11.9 mmol) and triethylamine (2.30 g; 22.8 mmol) in toluene (40 ml) and the mixture is stirred at this temperature for 2 h. The reaction mixture is filtered under argon and the filtrate is treated successively at room temperature with triethylamine (2.30 g; 22.8 mmol) and a solution of the compound from Example 51 A (2.35 g; 10.0 mmol) in toluene (10 ml). The reaction mixture is stirred at room temperature overnight and introduced into ethyl acetate (100 ml) and extracted with water (3×50 ml). The organic phase is dried ($MgSO_4$) and concentrated in vacuo. The residue is chromatographed on silica gel using toluene:ethyl acetate (1:1). The product thus obtained is stirred in ether, filtered off and dried in vacuo.

Yield: 2.60 g (70% of theory)

M.p.: 119–20° C.

$R_f$=0.14 (VII)

MS (DCI, $NH_3$): m/e=387 (M+$NH_4$)

Example 184

4-(Naphthyl-1-oxy)-benzenesulphonic acid N-benzylamide

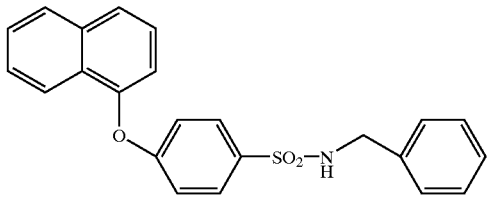

1-Naphthol (10.7 g; 74 mmol) and potassium carbonate (20.5 g; 148 mmol) are initially introduced into DMF (200 ml) and the mixture is stirred at room temperature for 1.5 h. After addition of 4-fluorobenzenesulphonic acid N-benzylamide (19.6 g; 74 mmol; Bull Soc. Chim. Fr. 1961, 488), the reaction mixture is stirred at 80° C. overnight and at 120° C. for 5 h. The DMF is then evaporated off in vacuo, the residue is treated with water and the mixture is extracted four times with ethyl acetate. The combined organic phases are washed twice with water, dried ($MgSO_4$) and concentrated in vacuo. The residue is chromatographed on silica gel using toluene:ethyl acetate (10:1). The product thus obtained is stirred with diethyl ether, filtered off and dried in vacuo.

Yield: 3.45 g (12% of theory)

M.p.: 144–46° C.

$R_f$=0.39 (IV)

MS (ESI): m/e=390 (M+H)

Example 185

1-N-(n-Pentylsulphonyl)amino-4-(2-ethoxycarbonylindan-4-oxy)benzene

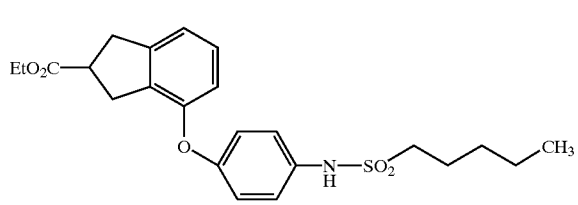

Preparation was carried out in analogy to the preparation of Example 1, starting from Example 98 A (0.546 g; 1.84 mmol) and 1-pentanesulphonyl chloride (0.313 g; 1.84 mmol).

Yield: 0 432 g (70% of theory)

$R_f$=0.45 (VII)

MS (ESI): m/e=432 (M+H)

Example 186

1-N-(n-Pentylsulphonyl)amino-4-(2-hydroxymethylindan-4-oxy)-benzene

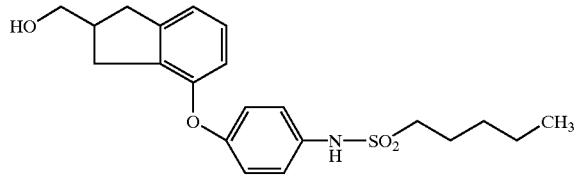

Preparation was carried out in analogy to the preparation of Example 91, starting from Example 185 (0.260 g; 0.60 mmol).

Yield: 0.209 g (87% of theory)

$R_f$=0.56 (VII)

MS (ESI): m/e=412 (M+Na)

Example 187

N-(3-Fluoro-(5-naphthyl-1-oxy)-phenyl)-N-hydroxy-1-pentane-sulphonyl chloride

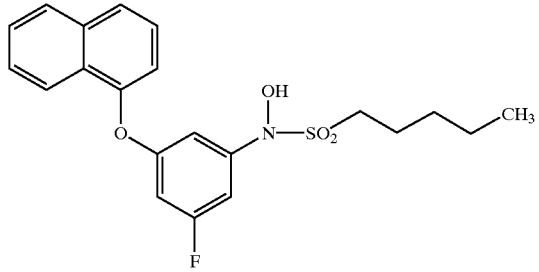

Preparation was carried out in analogy to the preparation of Example 1, starting from Example 101 A (1.29 g; 5.10 mmol) and 1-pentanesulphochloride (0.91 g; 5.36 mmol).

Yield: 0.24 g (12% of theory)
R$_f$=0.27 (X)
MS (FAB): m/e=404 (M+H)

Example 188

1-[(4,4,4-Trifluoro-1-butyl)sulphonyloxy]-3-(naphthyl-1-oxy)benzene

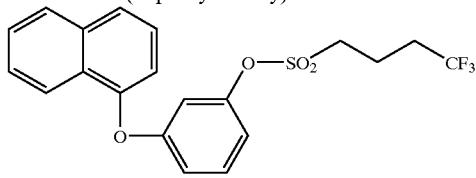

Preparation was carried out in analogy to the preparation of Example 97, starting from Example 63 A (0.709 g; 3.00 mmol).

Yield: 1.10 g (89% of theory)
R$_f$=0.50 (XXX)
MS (DCI, NH$_3$): m/e=428 (M+NH$_4$)

Example 189

5-[(4,4,4-Trifluoro-1-butyl)sulphonylamino]-2-(naphthyl-1-oxy)-pyridine

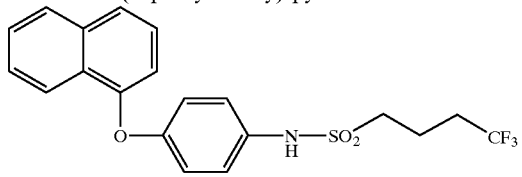

Preparation was carried out in analogy to the preparation of Example 1, starting from Example 43 A (0.945 g; 4.00 mmol).

Yield: 1.20 g (75% of theory)
M.p.: 136–137° C.
R$_f$=0.69 (VII)
MS (DCI, NH$_3$): m/e=411 (M+H)

The examples shown in Table 12 are prepared in analogy to the preparation of Example 1:

TABLE 12

R$^1$—O—G—NH—SO$_2$—R$^2$

| Ex. No. | R$^1$ | G | R$^2$ | Yield (% of theory) | M.p. (° C.) | R$_f$ | MS (m/e) |
|---|---|---|---|---|---|---|---|
| 190 | 1-acetamido-4-methylnaphthyl | p-phenylene | benzyl | 21 | 224 | 0.48 (XXXII) | 447 (M + H) (E) |
| 191 | 1-acetamido-4-methylnaphthyl | p-phenylene | n-Bu | 13 | 184 | 0.63 (XXXIII) | 413 (M + H) (E) |
| 192 | 2-methyl-5-methyl-tetrahydroisoquinolinyl | p-phenylene | benzyl | 14 | 85 | 0.55 (XXXIV) | 409 (M + H) (E) |
| 193 | 2-methyl-5-methyl-tetrahydroisoquinolinyl | p-phenylene | n-Bu | 12 | — | 0.65 (XXVII) | 403 (M + H) (C) |

TABLE 12-continued

R$^1$—O—G—NH—SO$_2$—R$^2$

| Ex. No. | R$^1$ | G | R$^2$ | Yield (% of theory) | M.p. (° C.) | R$_f$ | MS (m/e) |
|---|---|---|---|---|---|---|---|
| 194 | [N-acetyl-tetrahydroisoquinoline, 5-yl] | [p-phenylene] | [CH$_2$-phenyl] | 18 | — | 0.73 (VII) | 437 (M + H) (C) |
| 195 | [H$_3$C-CH$_2$CH$_2$-N-tetrahydroisoquinoline, 5-yl, xHCl] | a) | [p-phenylene] | n-Bu | 50 | 80 (dec.) | 0.17 (VII) | 403 (M − Cl) (B) |
| 196 | [H$_3$C-CH$_2$CH$_2$-N-tetrahydroisoquinoline, 5-yl, xHCl] | a) | [p-phenylene] | [CH$_2$-phenyl] | 72 | 120 (dec.) | 0.17 | 437 (M − Cl) (B) | a)Precipitated as the hydrochloride using HCl/diethyl ether

The preparation of the compounds listed in Table 13 is carried out in analogy to the procedure of Example 2.

TABLE 13

[naphthalen-1-yloxy, 2-CO$_2$CH$_3$, 3-NH—SO$_2$—R$^2$ benzene]

| Ex. | R$^2$ | Yield % | M.p. (° C.) | Rf | MS (m/e) |
|---|---|---|---|---|---|
| 197 | nBu | 49 | 92–3 | 0.23 (XXX) | 436 (M + Na) (C) |
| 198 | Bzl | 14 | 112–3 | 0.44 (XXX) | 470 (M + Na) (C) |
| 199 | nPent | 39 | 88–89 | 0.52 (XXXVI) | 428 (M + H) (C) |
| 200 | CF$_3$-(CH$_2$)$_3$- | 18 | oil | 0.27 (XI) | 490 (M + Na) (C) |

Example 201

2-(n-Butylsulphonylamino)-4-(1-naphthyloxy)-benzoic acid morpholinamide

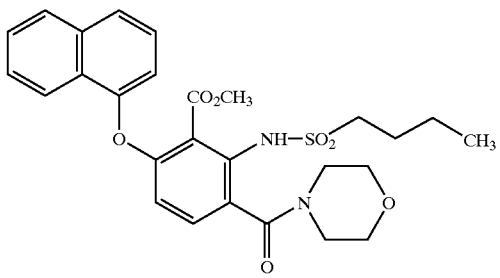

Triethylamine (1.8 ml; 13 mmol) and 20% propanephosphonic anhydride/ethyl acetate (1.04 ml; 1.58 mmol) were added to a solution of Example 172 (0.420 g; 1.05 mmol) and morpholine (90 μl; 11 mmol) in DMF (5 ml) and the mixture was stirred at room temperature overnight. After addition of the same amounts of morpholine, triethylamine and propanephosphonic anhydride solution and stirring overnight, the reaction mixture was poured onto water and extracted with ethyl acetate. The organic phases were dried over $Na_2SO_4$, filtered and concentrated, and the residue was chromatographed on silica gel (methylene chloride:methanol=30:1). Recrystallization from methanol afforded white crystals.

Yield: 33 mg (6.29% of theory)
M.p.: 105–108° C.
$R_f$: 0.55 (XXV)
MS: 469 (M+H) (B)

The preparation of the compounds listed in Table 14 is carried out in analogy to the procedure of Example 201.

The preparation of the compounds listed in Table 15 is carried out in analogy to the procedure of Example 91

TABLE 15

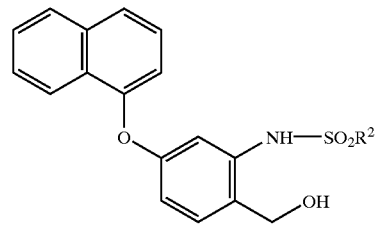

| Ex. | $R^2$ | Ausbeute (%) | M.p. (° C.) | $R_f$ | MS (m/e) |
|---|---|---|---|---|---|
| 206 | nBu | 81 | | 0.45 (XXVII) | 403 (M + $NH_4$) (B) |
| 207 | Bzl | 82 | oil | 0.45 (XXX) | 437 (M + $NH_4$) (B) |

The preparation of the compounds listed in Table 16 is carried out in analogy to the procedure of Example 1.

TABLE 14

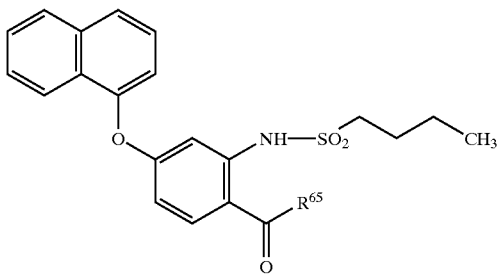

| Ex. | $R^{65}$ | Yield (%) | M.p. (° C.) | $R_f$ | MS (m/e) |
|---|---|---|---|---|---|
| 202 | —N(piperazine)NCH₃ | 3.18 | oil | 0.23 (XXV) | 482 (M + H) (C) |
| 203 | —NH~N(CH₃)₂ | 5.1 | oil | 0.53 (XXVI) | 470 (M + H) (C) |
| 204 | —NH~OCH₃ | 9.0 | oil | 0.64 (XXV) | 457 (M + H) (B) |
| 205[a)] | (piperidine)NCH₃ xHCl | 74 | 190 (dec.) | | 482 (M − Cl) |

[a)] Prepared by treatment of Example 202 with 1 N HCl/ether.

TABLE 16
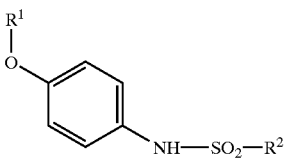
| Ex.[a] | R¹ | R² | Yield (%) | M.p. (° C.) | $R_f$ | MS (m/e) |
|---|---|---|---|---|---|---|
| 208 | 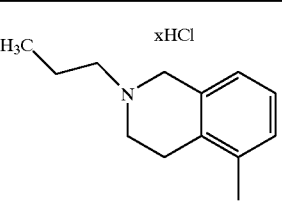 xHCl | 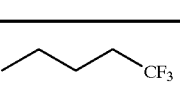 | 33 | 196–7 | 0.79 (XXVI) | 457 (M − Cl) (C) |
| 209 | 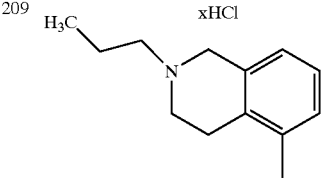 xHCl | 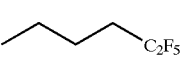 | 29 | 219–20 | 0.76 (XXVI) | 507 (M − Cl) (C) |
| 210 | 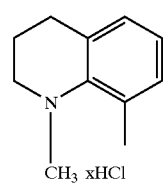 | nPent | 15 | 143–4 | 0.23 (IV) | 389 (M − Cl) (C) |
| 211 | 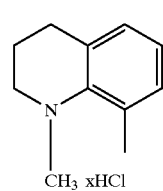 | Bzl | 13 | 192–4 | 0.21 (IV) | 409 (M − Cl) (C) |
| 212 | 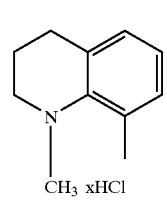 | 1-Naphth | 20 | 207–10 | 0.28 (IV) | 445 (M − Cl) (C) |
| 213 | 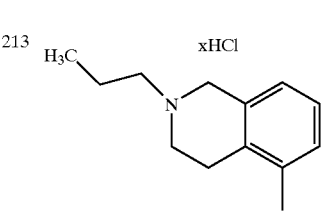 xHCl | nPent | 32 | | 0.24 (XXV) | 417 (M − Cl) (C) |
[a] Prepared by treatment of the corresponding amine with 1 N HCl/ether The preparation of the compounds listed in Table 17 is carried out in analogy to the procedure of Example 97.

TABLE 17

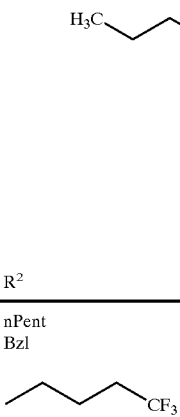

| Ex.[a)] | R² | Yield (%) | M.p. (° C.) | $R_f$ | MS (m/e) |
|---|---|---|---|---|---|
| 214 | nPent | 31 | 151.5–152.5 | 0.38 (XXXVII) | 418 (M − Cl) (C) |
| 215 | Bzl | 48 | 164–168.5 | 0.27 (XXXVII) | 438 (M − Cl) (C) |
| 216 | ~~~CF₃ (propyl-CF3) | 50 | 171–2 | 0.24 (XXXVII) | 458 (M − Cl) (C) |
| 217 | 1-Naphth | 64 | 156–157.5 | 0.31 (XXXVII) | 474 (M − Cl) (C) |

[a)] Prepared by treatment of the corresponding amine with 1 N HCl/ether

The compounds shown in Table 18 were prepared in analogy to the preparation of Preparation Example 1

TABLE 18

R¹—O—G—NH—SO₂—R²

| Ex. | R¹ | G | R² | Yield (% of theory) | $R_f$ | M.p. (° C.) | MS (m/e) |
|---|---|---|---|---|---|---|---|
| 218 | 2-methylphenyl | 1,4-phenylene | benzyl (CH₂C₆H₅) | 53 | 0.76 (XLIII) | 131 | 354 (M + H) (E) |
| 219 | 2-isopropylphenyl | 1,4-phenylene | benzyl | 18 | 0.74 (XLIII) | 82 | 382 (M + H) (E) |
| 220 | 2,6-diisopropyl-3-methylphenyl | 1,4-phenylene | benzyl | 58 | 0.74 (XLIII) | 107 | 424 (M + H) (E) |
| 221 | 2-methyl-6-morpholinophenyl | 1,4-phenylene | nBu | 13 | 0.68 (XLIII) | 274 | 391 (M + H) (E) |

TABLE 18-continued $$R^1\text{—}O\text{—}G\text{—}NH\text{—}SO_2\text{—}R^2$$

| Ex. | R[1] | G | R[2] | Yield (% of theory) | $R_f$ | M.p. (° C.) | MS (m/e) |
|---|---|---|---|---|---|---|---|
| 222 | 2-methyl-morpholinophenyl | p-tolyl | benzyl | 22 | 0.68 (XLIII) | 275 | 425 (M + H) (E) |
| 223 | 5-methyl-1-acetamidonaphthyl | p-tolyl | nBu | 25 | 0.56 (XXXIII) | 195 | 413 (M + H) (E) |
| 224 | 5-methyl-1-acetamidonaphthyl | p-tolyl | benzyl | 18 | 0.52 (XXXIII) | 227 | 447 (M + H) (E) |
| 225 | 4-methyl-1-acetamidonaphthyl | 5-methylpyridin-2-yl | n-Pent | 49 | 0.35 (XXXII) | 82 | 428 (M + H) (E) |
| 226 | 4-methyl-1-acetamidonaphthyl | 5-methylpyridin-2-yl | benzyl | 13 | 0.39 (XXXII) | 188 | 448 (M + H) (E) |
| 227 | 5-methyl-6-acetamidonaphthyl | p-tolyl | n-Pent | 7.5 | 0.41 (XLIII) | amorphous | — |

TABLE 18-continued
R¹—O—G—NH—SO₂—R²
| Ex. | R¹ | G | R² | Yield (% of theory) | $R_f$ | M.p. (° C.) | MS (m/e) |
|---|---|---|---|---|---|---|---|
| 228 | 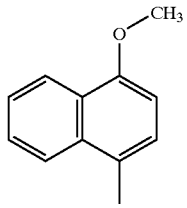 | 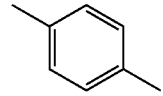 | 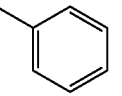 | 30 | — | 168 | 420 (M + H) (E) |
| 229 | 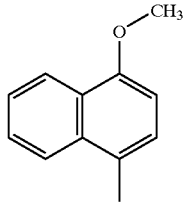 | 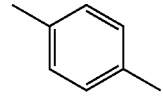 | n-Pent | 54 | 0.41 (XLIV) | 122 | 400 (M + H) (E) |
| 230 | 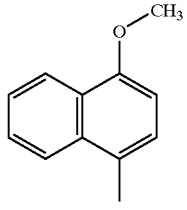 | 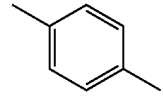 | 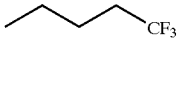 | 42 | 0.34 (XLIV) | 99 | — |
| 231 | 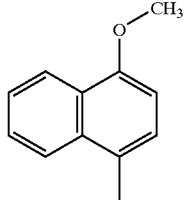 | 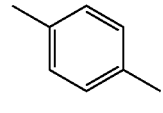 | n-Bu | 39 | 0.38 (XLIV) | 125 | 386 (M + H) (E) |
| 232[a)] | 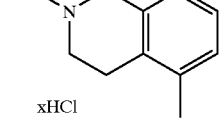 | 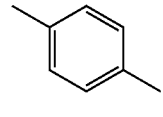 | 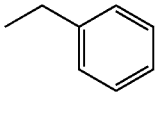 | 24 | 0.55 (XXXIV) | 222 | 409 (M + H) (E) |
| 233[a)] | 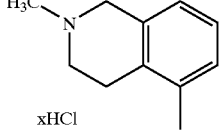 | 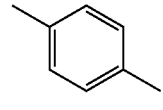 | n-Pent | 18 | 0.67 (XXXIV) | amorphous | 389 (M + H) (E) |
| 234[a)] | 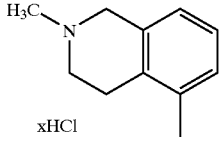 | 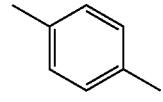 | 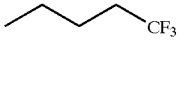 | 34 | 0.57 (XXXIV) | 220 | 429 (M + H) (E) |

TABLE 18-continued

R¹—O—G—NH—SO₂—R²

| Ex. | R¹ | G | R² | Yield (% of theory) | $R_f$ | M.p. (° C.) | MS (m/e) |
|---|---|---|---|---|---|---|---|
| 235[a)] | 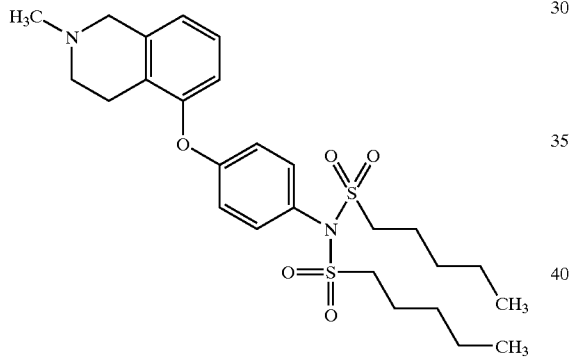 | | CF₃ substituted chain | 33 | 0.43 (XXXIII) | amorphous | 429 (M + H) (E) |
| 236 | 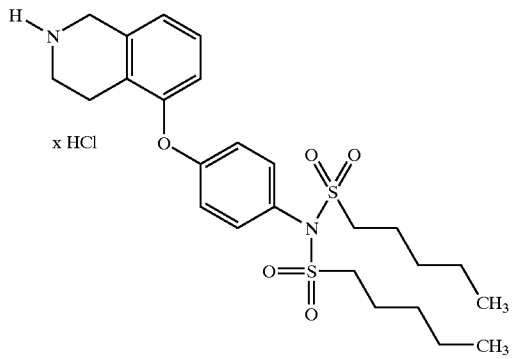 | | n-Hex | 14 | 0.38 (XXXIII) | 115 | — |

[a)]Conversion into the hydrochloride from the free amine

Example 237

1-Bis-N-(1-pentylsulphonyl)amino-4-(2-methyl-1,2,3,4-tetrahydroisoquinolin-5-yl-oxy)-benzene The compound from Example 108 A (3.5 g; 13.8 mmol) is reacted at 35 to 40° C. with 1-pentanesulphonyl chloride (5.17 g; 30.3 mmol) and triethylamine (9.6 ml, 70 mmol) in dichloromethane (30 ml) analogously to the procedure for the compound from Example 3. After complete reaction, the batch is extracted with water, sodium hydrogen carbonate solution and water. The organic phase is dried over sodium sulphate and concentrated in vacuo. The crude product is purified by column chromatography on silica gel (dichloromethane/methanol, 98:2).

Yield: 1.7 g (24% of theory)

$R_f$=0.58 (XLV)

MS (DCI, isobutane): m/e=523 (M+H)

Example 238

1-Bis-N-(1-pentylsulphonyl)amino-4-(1,2,3,4-tetrahydroisoquinolin-5-yl-oxy)-benzene hydrochloride α-Chloroethyl chloroformate (1.1 g; 7.7 mmol) is added at 0° C. to a solution of the compound from Example 237 (1 g; 1.92 mmol) in absolute 1,2-dichloroethane. The mixture is then heated under reflux for 16 hours. The reaction batch is concentrated in vacuo, treated with methanol (20 ml) and heated under reflux for 1 h. After completion of the reaction, the mixture is concentrated in vacuo and the residue is recrystallized from absolute ethanol (13 ml).

Yield: 625 mg (64.0% of theory)

$R_f$=0.22 (XXIII)

M.p.: 162° C.

MS (DCI, isobutane): m/e=509 (M+H)

Example 239

1-Bis-N-(1-pentylsulphonyl)amino-4-(2-isopropyl-1,2,3,4-tetrahydroisoquinolin-5-yl-oxy)-benzene

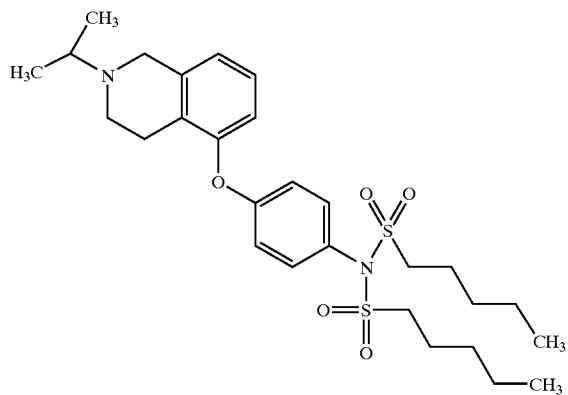

Acetone (1.0 g; 17.2 mmol), molecular sieve (20 beads, 3 Å) and sodium cyanoborohydride (240 mg, 2.81 mmol) are added at room temperature to a solution of the compound from Example 238 (300 mg, 0.55 mmol) in absolute methanol (15 ml). The pH of the reaction batch is set between 5 and 6 using a few drops of acetic acid. The mixture is stirred at room temperature for 20 hours. The batch is then rendered alkaline using sodium hydroxide solution, extracted with dichloromethane, and the organic phase is dried over sodium sulphate and concentrated in vacuo.

Yield: 300 mg of crude product which is directly reacted further to give Example 240.

$R_f$=0.37 (XXXIII)

MS (DCI, isobutane): m/e=551 (M+H)

Example 240

N-(1-Pentylsulphonyl)amino-4-(2-isopropyl-1,2,3,4-tetrahydroisoquinolin-5-yl-oxy)-benzene hydrochloride

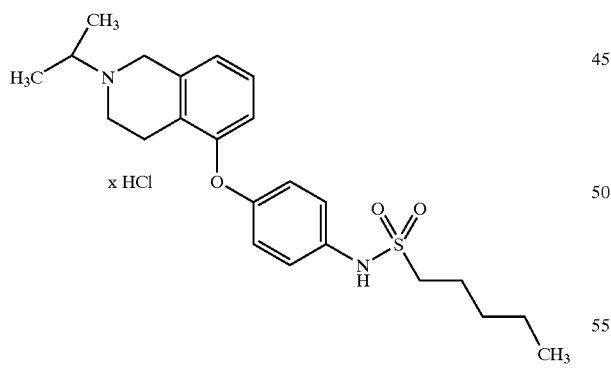

A solution of the compound from Example 239 (370 mg, 0.672 mmol) in tetrahydrofuran (10 ml) and 1 N sodium hydroxide solution (1.35 ml, 1.35 mmol) is stirred at room temperature for 8 hours. The batch is then acidified to pH 1 using 1 N hydrochloric acid and extracted with dichloromethane. The organic phase is dried over sodium sulphate and concentrated in vacuo. The product is purified by column chromatography on silica gel (eluent:dichloromethane/methanol, 98:2). The product is converted into the hydrochloride after dissolving in ethanol, treating with 1 N hydrochloric acid and subsequent concentration in vacuo.

Yield: 239 mg (79% of theory)

$R_f$=0.39 (XXXIII)

M.p.: amorphous

MS (DCI, isobutane): m/e=417 (M+H)

Example 241

1-Bis-N-(1-pentylsulphonyl)amino-4-(2-butyl-1,2,3,4-tetrahydroisoquinolin-5-yl-oxy)-benzene

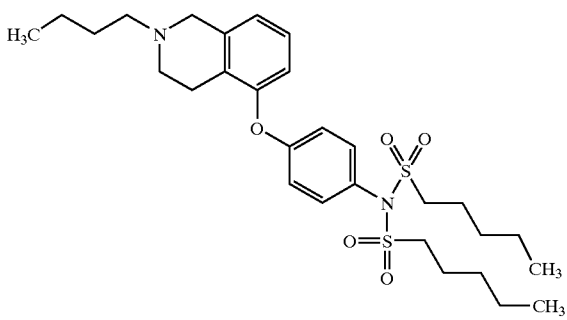

The product is prepared from the compound from Example 238 (215 mg, 0.394 mmol) and butyraldehyde (889 mg; 12.3 mmol) analogously to Example 239.

Yield: 260 mg of crude product which is directly reacted to give Example 242.

$R_f$=0.7 (XXXIII)

MS (DCI, isobutane): m/e=565 (M+H)

Example 242

N-(1-Pentanesulphonyl)amino-4-(2-butyl-1,2,3,4-tetrahydroisoquinolin-5-yl-oxy)-benzene

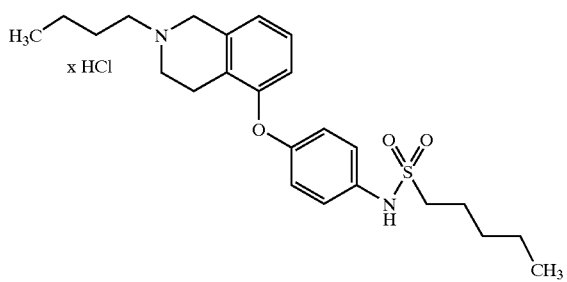

The product is prepared from the compound from Example 241 (255 mg, 0.451 mmol) analogously to Example 240.

Yield: 236 mg (64% of theory)

$R_f$=0.25 (XXXIII)

M.p.: 187° C.

MS (DCI, isobutane): m/e=431 (M+H)

The examples shown in Table 19 were prepared in analogy to the preparation of Example 97:

TABLE 19

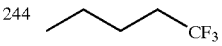

| Ex. | R² | Yield (% of theory) | M.p. (° C.) | R_f (eluent) | MS (m/e) |
|---|---|---|---|---|---|
| 243 | n-Pent | 71 | amorphous | 0.5 (XLV) | 390 (M + H) (E) |
| 244 | ⌇⌇⌇CF₃ | 28 | oil | — | 430 (M + H) (E) |
| 245 | ⌇⌇Ph | 20 | oil | — | 410 (M + H) (E) |

The compounds from Table 19 are converted into the corresponding hydrochlorides shown in Table 20 by dissolving in methanol or ethanol, treating with 1 N hydrochloric acid and subsequently concentrating in vacuo

TABLE 20

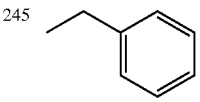

| Ex. | R² | M.p. (° C.) |
|---|---|---|
| 246 | n-Pent | amorphous |
| 247 | ⌇⌇⌇CF₃ | 176 |
| 248 | ⌇⌇Ph | 87 |

Example 249

4-(1,2,3,4-Tetrahydroisoquinolin-5-yl-oxy)-1-(1-pentanesulphonyl)oxy-benzene

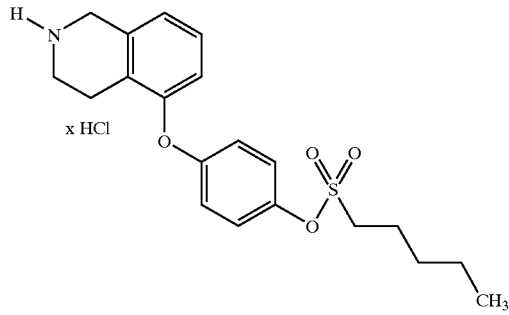

The product is prepared from the compound from Example 243 (2 g; 5.14 mmol) analogously to Example 238.

Yield: 1.60 g (75% of theory)

$R_f$=0.23 (XXXIII)

M.p.: 143° C.

MS (DCI, isobutane): m/e=376 (M+H)

The examples shown in Table 21 were prepared in analogy to the preparation of Example 97. The amines are converted into the hydrochlorides by dissolving in methanol or ethanol, treating with 1 N hydrochloric acid and subsequently concentrating in vacuo.

TABLE 21

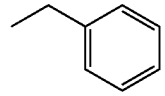

| Ex. | R³ | Yield (% of theory) | M.p. (° C.) | R_f | MS (m/e) |
|---|---|---|---|---|---|
| 250 | Ethyl | 22 | — | 0.48 (XXXIII) | — |
| 251 | Isopropyl | 85 | 185 | 0.56 (XXXIII) | 418 (M + H) (E) |
| 252 | n-Butyl | 55 | 151 | 0.69 (XXXIII) | 432 (M + H) (E) |

Example 253

1-(4-Aminonaphth-1-yl-oxy)-4-(benzylsulphonylamino)-benzene hydrochloride

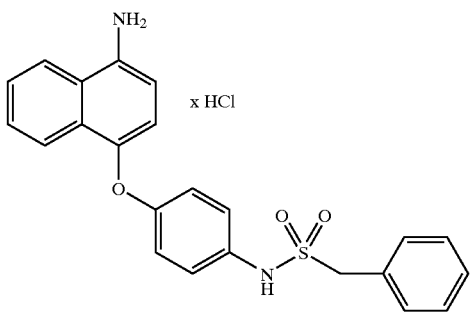

The compound from Example 190 (374 mg, 0.839 mmol) is dissolved in warm ethanol (200 ml). After addition of half-concentrated hydrochloric acid (200 ml), the mixture is heated under reflux for one and a half hours and then concentrated in vacuo.

Yield: 370 mg (100% of theory)

$R_f$=0.46 (XLI)

M.p.: 252° C.

MS (FAB): m/e=405 (M+H)

Example 254

4-(Benzylsulphonylamino)-1-(4-ethylcarbonylamino-naphth-1-yl-oxy)benzene

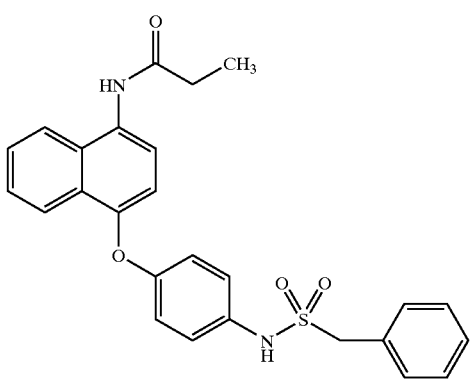

A mixture consisting of the compound from Example 253 (52 mg, 0.12 mmol) in absolute dichloromethane (40 ml) and absolute tetrahydrofuran (30 ml), triethylamine (24 mg, 0.24 mmol) and propionyl chloride (18 mg, 0.18 mmol) is stirred at room temperature for 16 hours. The reaction batch is concentrated in vacuo and the crude product is recrystallized from ethanol.

Yield: 42 mg (% of theory)

$R_f$=0.35 (XLI)

M.p.: 180° C.

MS (DCI, isobutane): m/e=461 (M+H)

The examples shown in Table 22 were prepared in analogy to the preparation of Example 254:

TABLE 22

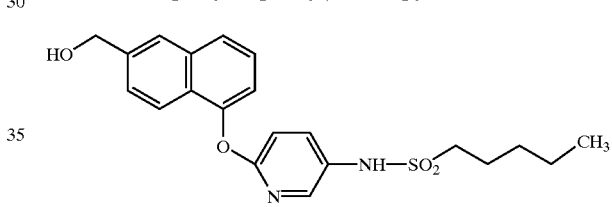

| Ex. | $R^{66}$ | Yield (% of theory) | M.p. (° C.) | $R_f$ | MS (m/e) |
|---|---|---|---|---|---|
| 255 | Cyclopropyl-carbonyl | 66 | 177 | 0.54 (XLI) | 473 (M + H) (E) |
| 256 | Benzoyl | 46 | 197 | 0.56 (XLI) | 509 (M + H) (E) |
| 257 | Methane-sulphonyl | 22 | 205 | 0.3 (XLVI) | 483 (M + H) (E) |

Example 258

2-(6-Hydroxymethyl-naphthyl-1-oxy)-5-(N-1-pentylsulphonyl)amino-pyridine

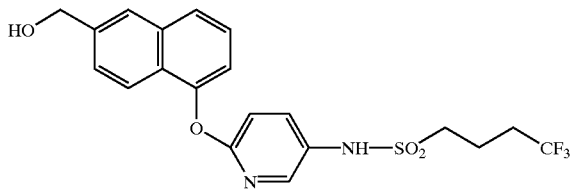

Preparation was carried out in analogy to the preparation of Example 1, starting from Example 143 A (7.30 g; 27.4 mmol).

Yield: 2.98 g (27% of theory)

$R_f$=0.42 (VII)

MS (ESI): m/e=401 (M+H)

Example 259

2-(6-Hydroxymethyl-naphthyl-1-oxy)-5-(4,4,4-trifluoro-1-butylsulphonyl)amino-pyridine Preparation was carried out in analogy to the preparation of Example 1, starting from Example 143 A (1.01 g; 3.78 mmol).

Yield: 0.62 g (36% of theory)

M.p.: 60° C.

$R_f$=0.36 (VII)

MS (DCI/NH$_3$): m/e=441 (M+H)

Example 260

3-(6-Methyl-naphthyl-1-oxy)-1-(4,4,4-trifluoro-1-butylsulphonyl)amino-benzene

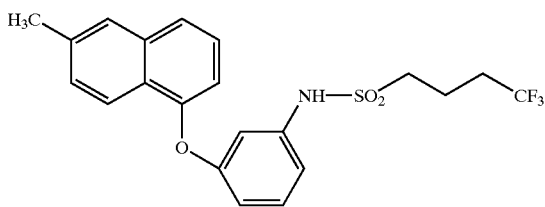

Preparation was carried out in analogy to the preparation of Example 1, starting from Example 141 A (0.90 g; 3.61 mmol).
Yield: 1.09 g (71% of theory)
M.p.: 75–77° C.
$R_f$=0.38 (dichloromethane)
MS (ESI): m/e=424 (M+H)

Example 261

5-(1-Butylsulphonyl)amino-2-(naphthyl-1-oxy)-benzoic acid N-morpholinamide

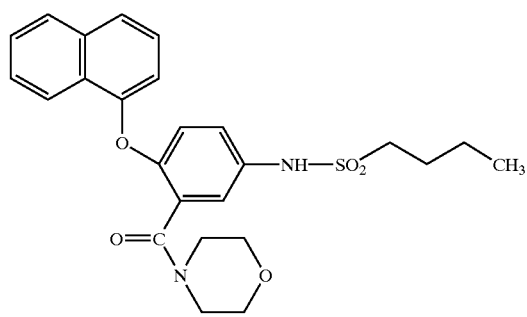

Preparation was carried out in analogy to the preparation of Example 79, starting from Example 75 (0.509 g; 1.27 mmol).
Yield: 0.425 g (71% of theory)
$R_f$=0.29 (dichloromethane:MeOH=40:1)
MS (DCI, NH$_3$): m/e=486 (M+H)

Example 262

4-(Naphth-1-yl-oxy)-2-(1-N-pentylsulphonyl)aminopyridine

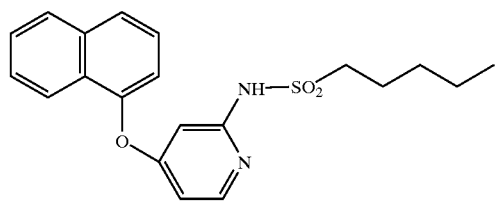

Preparation was carried out in analogy to the preparation of Example 2, starting from Example 139 A (0.300 g; 1.27 mmol).
Yield: 0.164 g (35% of theory)
$R_f$=0.66 (VII)
MS (ESI): m/e=371 (M+H)

Example 263

2-(N-Benzylsulphonyl)amino-4-(naphth-1-oxy)-pyridine

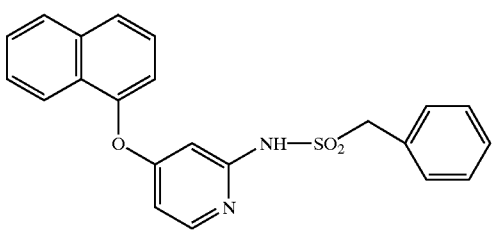

Preparation was carried out in analogy to the preparation of Example 2, starting from Example 139 A (0.300 g; 1.27 mmol).
Yield: 0.289 g (58% of theory)
$R_f$=0.55 (VII)
MS (ESI): m/e=391 (M+H)

Example 264

3-Fluoro-5-(naphthyl-1-oxy)-1-(N-1-pentylsulphonyl)amino-benzene

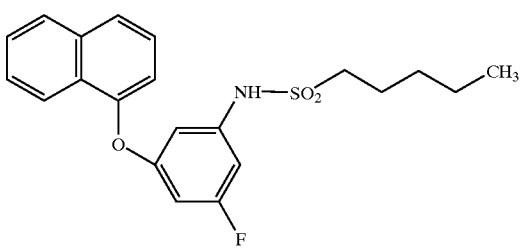

Preparation was carried out in analogy to the preparation of Example 1, starting from Example 100 A (1.00 g; 3.95 mmol).
Yield: 1.49 g (96% of theory)
M.p.: 72° C.
$R_f$=0.50 (IV)
MS (ESI): m/e=410 (M+Na)

Example 265

1-(N-Benzylsulphonyl)amino-3-fluoro-5-(naphthyl-1-oxy)-benzene

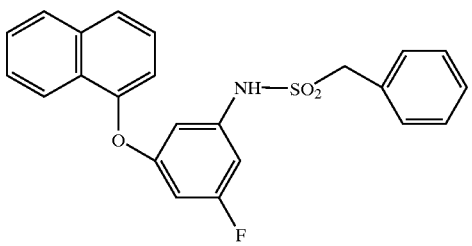

Preparation was carried out in analogy to the preparation of Example 1, starting from Example 100 A (1.00 g; 3.95 mmol).
Yield: 1.29 g (77% of theory)
M.p.: 122° C.

$R_f$=0.54 (IV)
MS (DCI, NH$_3$): m/e 425 (M+NH$_4$)

Example 266

3-Fluoro-5-(naphthyl-1-oxy)-1-(4,4,4-trifluoro-1-butylsulphonyl)amino-benzene

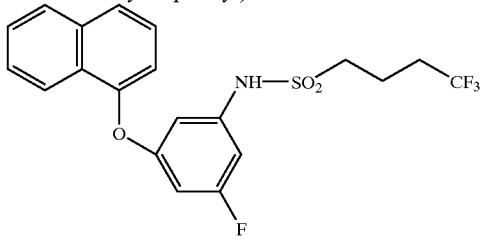

Preparation was carried out in analogy to the preparation of Example 1, starting from Example 100 A (1 00 g; 3 95 mmol).

Yield: 1.18 g (69% of theory)
$R_f$=0.49 (IV)
MS (DCI/NH$_3$): m/e=445 (M+NH$_4$)

Examples 267 and 268

(R)- and (S)-1-N-(n-Pentylsulphonyl)amino-4-(2-hydroxymethylindanyl-4-oxy)-benzene

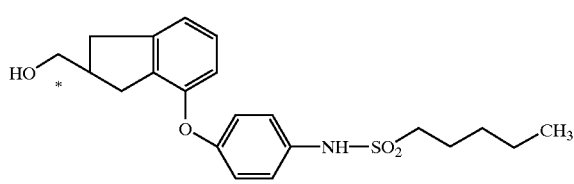

Enantiomer A (Example 267) and enantiomer B (Example 268)

The compound from Example 186 (0.100 g; 0.257 mmol) is separated into the two enantiomers A (Example 267) and B (Example 268) by means of preparative HPLC (Chiralpak AD, 250 mm×20 mm), eluent 82% petroleum ether/18% iPrOH, T=50° C., flow rate=0.2 ml/min).

Example 267: Yield: 34.3 mg (68% of theory) Retention time: 10.6 min
Example 268: Yield: 13.3 mg (26% of theory) Retention time: 11.4 min

Example 269

3-(Naphthyl-1-oxy)-1-[2-(bis-trifluoromethyl-methoxy)ethylsulphonyl]amino-benzene

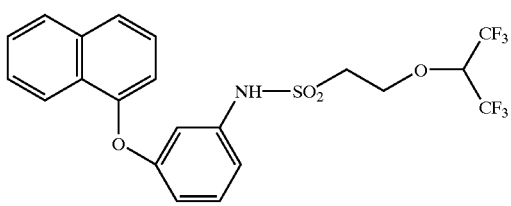

Preparation was carried out in analogy to the preparation of Example 1, starting from Example 45 A (0.518 g; 2.20 mmol).

Yield: 0.315 g (28% of theory)
$R_f$=0.56 (dichloromethane)
MS (DCI, NH$_3$): m/e=511 (M+NH$_4$)

Example 270

3-(Naphthyl-1-oxy)-1-(4,4,5,5,5-pentafluoro-1-pentylsulphonyl)amino-benzene

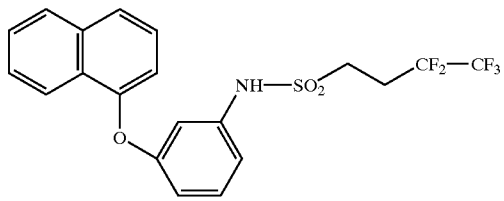

Preparation was carried out in analogy to the preparation of Example 1, starting from Example 45 A (0.518 g; 2.20 mmol).

Yield: 0.665 g (63% of theory)
$R_f$=0.54 (dichloromethane)
MS (DCI, NH$_3$): m/e=477 (M+NH$_4$)

Example 271

3-(Naphthyl-1-oxy)-1-(4,4,5,5,5-pentafluoro-1-pentylsulphonyl)oxy-benzene

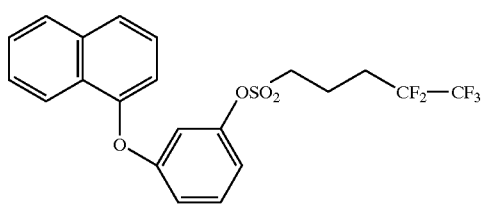

Preparation was carried out in analogy to the preparation of Example 97, starting from Example 63 A (0.210 g; 0.89 mmol).

Yield: 0.346 g (85% of theory)
$R_f$=0.38 (dichloromethane)
MS (ESI): m/e=461 (M+H)

Example 272

3-(6-Methoxymethyl-naphthyl-1-oxy)-1-(N-1-pentylsulphonyl)amino-benzene

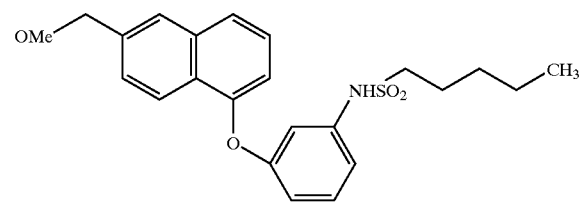

Preparation was carried out in analogy to the preparation of Example 1, starting from Example 144 A (59.0 mg; 0.21 mmol).

Yield: 64 g (74% of theory)
$R_f$=0 77 (dichloromethane:EA=10:1)
MS (OCI, NH$_3$): m/e=431 (M+NH$_4$)

Example 273

(R,S)-1-N-(4,4,4-Trifluoro-1-butylsulphonyl)amino-
3-(2-hydroxymethyl-indanyl-4-oxy)-benzene

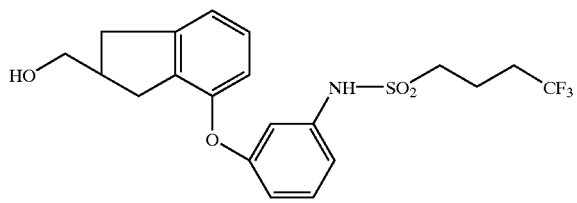

Preparation was carried out in analogy to the preparation of Example 1, starting from Example 146 A (0.800 g; 3.13 mmol).

Yield: 0.832 g (64% of theory)
$R_f$=0.50 (VII)
MS (DCI, $NH_3$): m/e=447 ($M+NH_4$)

Examples 274 and 275

(R) and (S)-1-N-(4,4,4-Trifluoro-1-butylsulphonyl)amino-3-(2-hydroxymethyl-indanyl-4-oxy)-benzene

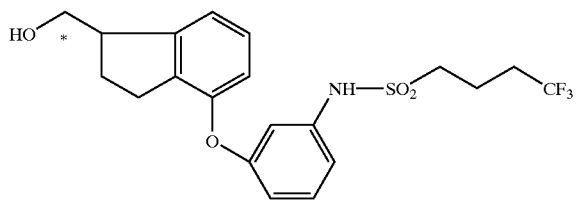

Enantiomer A (Example 274) and enantiomer B (Example 275)

The compound from Example 273 (0.560 g; 1.30 mmol) is separated into the enantiomers A (Example 274) and B (Example 275) by means of preparative HPLC (Chiralpak AD 10 μm, 250×20 mm, eluent 88% petroleum ether 40° C. –70° C./12% EtOH, T=15° C.).

Example 274: Yield: 85 mg (15% of theory) Retention time: 13.3 min.

Example 275: Yield: 80 mg (14% of theory) Retention time: 15.6 min.

Example 276

(R,S)-1-(4,4,4-Trifluoro-1-butylsulphonyl)oxy-3-(2-hydroxymethylindanyl-4-oxy)-benzene

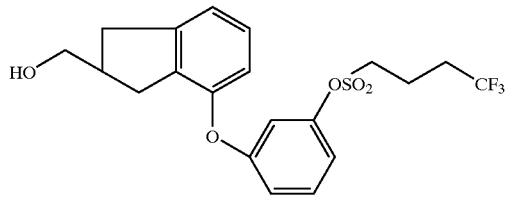

A solution of Example 147 A (1.228 g; 4.79 mmol) in THF (10 ml) is treated at room temperature under argon with potassium tert-butoxide (0.538 g; 4.79 mmol) and stirred at room temperature for 30 min. 4,4,4-Trifluorobutane-1-sulphonyl chloride (1.009 g; 4.79 mmol) is then added dropwise and the reaction mixture is stirred for 16 h. After addition of ethyl acetate (50 ml), the mixture is washed with water (50 ml) and satd aqueous NaCl solution (50 ml) and dried ($Na_2SO_4$), and the solvent is stripped off in vacuo. The residue is chromatographed on silica gel using toluene:EA (3:1).

Yield: 0.894 g (41% of theory)
$R_f$=0.39 (tol:EA=3:1)
MS (DCI, $NH_3$): m/e=448 ($M+NH_4$)

Examples 277 and 278

(R)- and (S)-1-(4,4,4-Trifluoro-1-butylsulphonyl)oxy-3-(2-hydroxymethylindanyl-4-oxy)-benzene

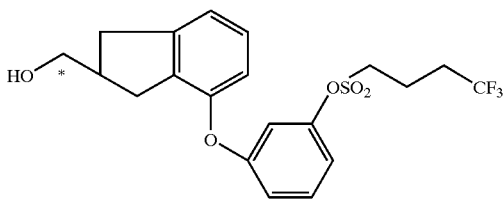

(+)-Enantiomer A (Example 277) and (–)-enantiomer B (Example 278)

The compound from Example 276 (490 mg; 1.14 mmol) is separated into the enantiomers A (Example 277) and B (Example 278) by means of preparative HPLC (Chiracel OD, 10 μm, 250×20 mm, flow rate 10 ml/min, eluent 80% petroleum ether 40–70° C./20% isopropanol, T=10° C.).

Example 277: Yield: 111 mg (23% of theory)

M.p.: 60–61° C. Retention time: 12.5 min $[\alpha]_D^{20}$ (c=1, MeOH)=+10.70

Example 278: Yield: 105 mg (21% of theory)

M.p.: 60–61° C. Retention time: 15.4 min $[\alpha]_D^{20}$ (c=1, MeOH)=–10.35

Example 279

5-[(4,4,4-Trifluoro-1-butyl)sulphonylamino]-2-(naphthyl-1-oxy)-pyridine sodium salt

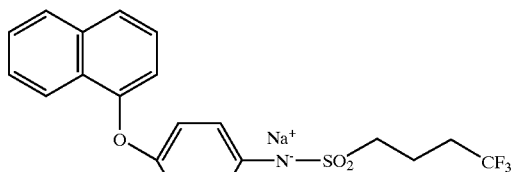

Preparation was carried out in analogy to the preparation of Example 128, starting from Example 189 (452 mg; 1.10 mmol).

Yield: 315 mg (66% of theory)

M.p.: 170° C. (d)

The preparation of the examples listed in Table 23 is carried out in analogy to Example 279.

TABLE 23

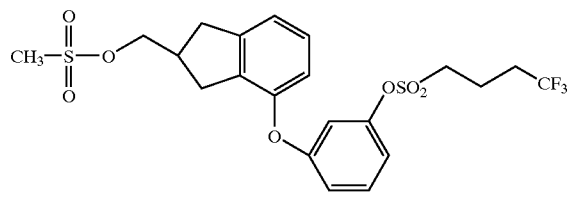

| Ex. | G | R² | Yield (% d. Th.) | M.p. (° C.) |
|---|---|---|---|---|
| 280 | 3,5-dimethylpyridinyl | n-Pent | 82 | 150 (d.) |
| 281 | 3,5-dimethylpyridinyl | CH₂CH₂-Ph | 92 | 210 (d.) |
| 282 | 3,5-dimethyl-fluorophenyl | n-Pent | 99 | 95 (d.) |
| 283 | 3,5-dimethyl-fluorophenyl | CH₂CH₂-Ph | 98 | 105 (d.) |
| 284 | 3,5-dimethyl-fluorophenyl | (CH₂)₃CF₃ | 98 | 56–60 |

Example 285

5-Fluoro-1-[(4,4,4-trifluoro-1-butyl)sulphonyl]amino-3-(naphthyl-1-oxy)-benzene potassium salt

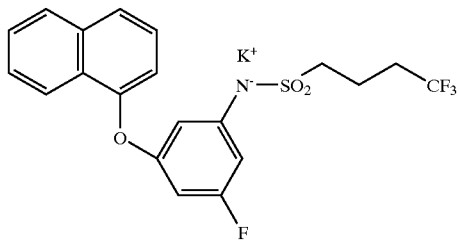

Preparation was carried out in analogy to the preparation of Example 128, starting from Example 266 (400 mg; 0.94 mmol) using potassium tert-butoxide (105 mg; 0.94 mmol) instead of sodium methoxide.

Yield: 433 mg (99% of theory)

M.p.: 46–50° C.

Example 286

(R,S)-1-[(4,4,4-Trifluoro-1-butyl)sulphonyl]amino-3-(2-methanesulphonyloxymethyl-indanyl-4-oxy)-benzene

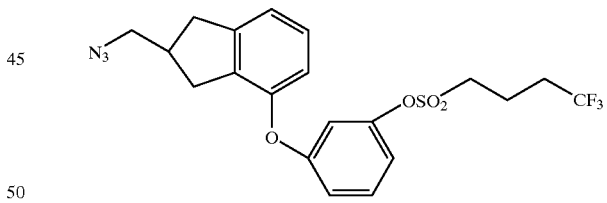

Methanesulphonyl chloride (195 mg; 1.70 mmol) is added dropwise under argon at −10° C. to the solution of Example 276 (665 mg; 1.55 mmol) and triethylamine (235 mg, 2 32 mmol) in dichloromethane (10 ml), and the batch is stirred at −10° C. for a further 30 min and allowed to warm to room temperature. The reaction mixture is diluted with dichloromethane (10 ml) and washed with water (20 ml), 1 N hydrochloric acid (10 ml), satd aqueous NaHCO₃ solution (20 ml) and water (20 ml), dried (Na₂SO₄) and concentrated in vacuo.

Yield: 706 mg (88% of theory)

$R_f$=0.74 (VII)

MS (ESI): m/e=509 (M+H)

Example 287

(R,S)-3-(2-Azidomethyl-indanyl-4-oxy)-1-[(4,4,4-trifluoro-1-butyl)sulphonyl]amino-benzene A solution of Example 286 (637 mg; 1.25 mmol) in DMSO (5 ml) is treated with sodium azide (407 mg; 6.26 mmol) and stirred under argon at 80° C. for 1 h. After addition of water (50 ml), the mixture is extracted with diethyl ether (2×50 ml). The combined organic phases are washed with water (30 ml), dried (Na₂SO₄) and concentrated in vacuo.

Yield: 507 mg (87% of theory)

$R_f$=0.78 (IV)

MS (EI): m/e=427 (M−N₂)

Example 288

(R,S)-3-(2-Aminoethyl-indanyl-4-oxy)-1-[(4,4,4-trifluoro-1-butyl)sulphonyl]amino-benzene hydrochloride

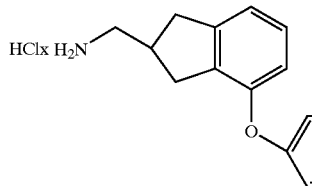

Example 287 (457 mg; 1.00 mmol) is dissolved in MeOH (10 ml), treated with palladium on active carbon, 10% strength (50 mg) and hydrogenated at 1 bar of hydrogen for 1.5 h. The batch is filtered through silica gel and concentrated in vacuo. The residue is taken up in diethyl ether (5 ml) and MeOH (4 ml) and treated with a saturated solution of HCl in diethyl ether (2 ml). The solvent is then stripped off in vacuo and the residue is stirred in diethyl ether, filtered off and dried in vacuo.

Yield: 321 mg (69% of theory)

M.p.: 192° C.

$R_f$=0.10 (dichloromethane:MeOH=20:1)

MS (DCI, $NH_3$): m/e=430 (M+H)

Example 289

(R,S)-3-(2-Dimethylaminomethyl-indanyl-4-oxy)-1-[(4,4,4-trifluoro-1-butyl)sulphonyl]amino-benzene hydrochloride

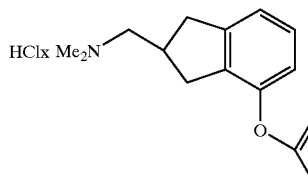

Example 288 (140 mg, 0.30 mmol) is dissolved in dichloromethane and washed with aqueous $NH_3$ solution. The aqueous phase is washed with dichloromethane (2×20 ml). The combined org. phases are dried ($Na_2SO_4$) and concentrated in vacuo. The residue is dissolved in acetonitrile (5.0 ml) and treated at room temperature with a 37% strength aqueous formaldehyde solution (246 mg; 3.0 mmol) and sodium cyanoborohydride (191 mg; 3.0 mmol). The mixture is stirred at room temperature for 30 min, a pH of 3 is set using acetic acid, the mixture is stirred for 5 min and 20 ml of 1 N NaOH are added. The reaction mixture is washed with dichloromethane (2×20 ml). The combined org. phases are dried ($Na_2SO_4$) and concentrated in vacuo in a rotary evaporator. The residue is dissolved in MeOH (5 ml) and treated with a saturated solution of HCl in diethyl ether (0.1 ml). The solution is then concentrated in vacuo.

Yield: 134 mg (90% of theory)

$R_f$=0.33 (XXV)

MS (DCI, $NH_3$): m/e=458 (M+H)

Example 290

1-[(4,4,4-Trifluoro-1-butyl)-sulphonyl]amino-3-(6-hydroxy-methyl-naphthyl-1-oxy)benzene

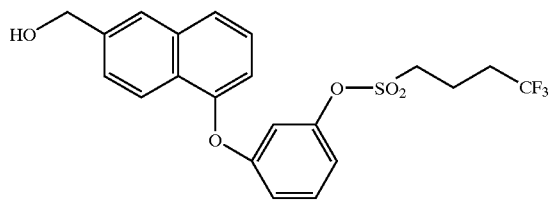

Preparation was carried out in analogy to the preparation of Example 276, starting from Example 148 A (1.01 g; 3.80 mmol).

Yield: 0.72 g (43% of theory)

$R_f$=0.60 (tol:EA=5.4)

MS (DCI, $NH_3$): m/e=458 (M+$NH_4$)

Example 291

3-(6-Hydroxymethyl-naphthyl-1-oxy)-1-(1-pentylsulphonyl)oxy-benzene

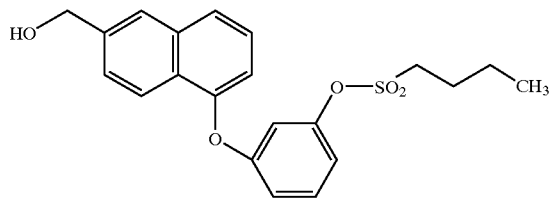

Preparation was carried out in analogy to the preparation of Example 276, starting from Example 148 A (5.33 g; 20.0 mmol).

Yield: 4.00 g (49% of theory)

$R_f$=0.67 (VI)

MS (DCI, $NH_3$): m/e=418 (M+$NH_4$)

Example 292

3-(6-Methanesulphonyloxymethyl-naphthyl-1-oxy)-1-(1-pentylsulfonyl)oxy-benzene

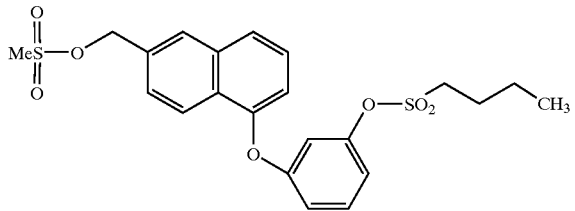

Preparation was carried out in analogy to the preparation of Example 286, starting from Example 291 (3.73 g; 9.00 mmol)

Yield: 3.19 g (74% of theory)

$R_f$=0.64 (tol:EA=5.2)

MS (DCI, $NH_3$): m/e=496 (M+$NH_4$)

Example 293

3-(6-Azidomethyl-naphthyl-1-oxy)-1-(1-pentylsulphonyl)-oxy-benzene

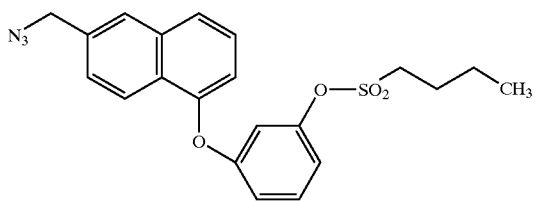

Preparation was carried out in analogy to the preparation of Example 287, starting from Example 292 (3.60 g; 7.52 mmol).

Yield: 2.68 g (84% of theory)

$R_f$=0.88 (tol:EA=5:2)

MS (DCI, $NH_3$): m/e=443 (M+$NH_4$)

Example 294

3-(6-Aminomethyl-naphthyl-1-oxy)-1-(1-pentylsulphonyl)-oxy-benzene hydrochloride

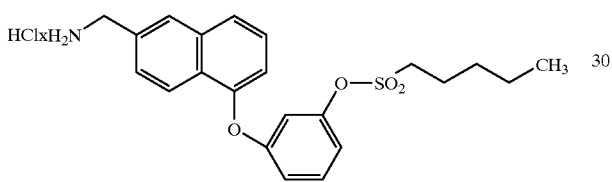

Preparation was carried out in analogy to the preparation of Example 288, starting from Example 293 (2.40 g; 5.64 mmol).

Yield: 2.23 g (90% of theory)

M.p.: >150° C. (d.)

$R_f$=0 41 (XXV)

MS (DCI, $NH_3$): m/e=400 (M+H)

Example 295

3-(6-N,N-Dimethylaminomethyl-naphthyl-1-oxy)-1-(1-pentylsulphonyl)oxy-benzene hydrochloride

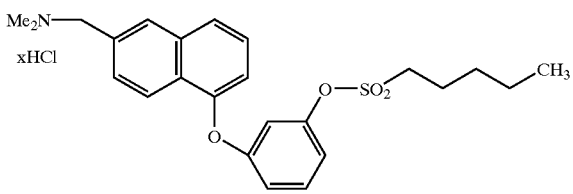

Preparation was carried out in analogy to the preparation of Example 289, starting from Example 294 (1.09 g; 2.50 mmol).

Yield: 0.220 g (19% of theory)

$R_f$=0.49 (XXV)

MS (DCI, $NH_3$): m/e=428 (M+H)

Example 296

1-(1-Pentylsulphonyl)amino-4-(2,3-dimethyl-phenyl-1-oxy)-benzene

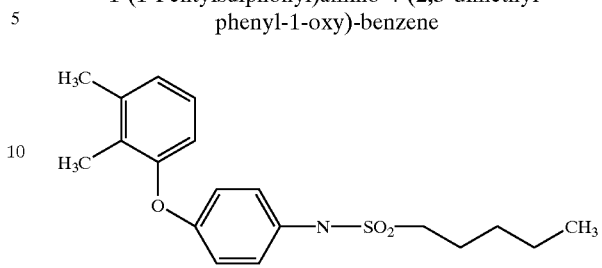

Preparation was carried out in analogy to the preparation of Example 1, starting from Example 29 A (7.25 g; 34.0 mmol).

Yield: 10.9 g (93% of theory)

$R_f$=0.43 (IV)

MS (ESI): m/e=348 (M+H)

Example 297

1-[N,N-Bis-(1-pentylsulphonyl)amino]-4-(2,3-dimethyl-phenyl-1-oxy)benzene

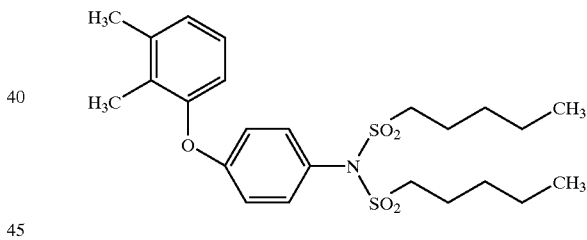

Potassium tert-butoxide (1.18 g; 10.5 mmol) is added with ice-cooling to a solution of Example 296 (3.48 g; 10.0 mmol) in THF (40 ml), the mixture is stirred for 20 min and 1-pentanesulphonyl chloride (2.04 g; 12.0 mmol) is then added dropwise at 0° C. The mixture is stirred at room temperature overnight and extracted three times with ethyl acetate after addition of water. The combined org. phases are washed twice with water, dried ($MgSO_4$) and concentrated in vacuo. The residue is chromatographed on silica gel using toluene.

Yield: 3.71 g (77% of theory)

M.p.: 91° C.

$R_f$=0.64 (PE:diethyl ether=10:3)

MS (ESI): m/e=482 (M+H)

Example 298

1-[N,N-Bis-(1-pentylsulphonyl)amino]-4-[2,3-(bis-bromomethyl)-phenyl-1-oxy]benzene

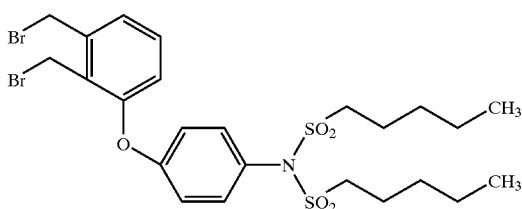

N-Bromosuccinimide (10.2 g; 57.4 mmol) is added to a solution of Example 297 (13.0 g; 27.0 mmol) in CCl$_4$ (250 ml) and the batch is heated to reflux for 4 h with simultaneous irradiation using a 300 W lamp. After cooling, the batch is filtered and the filtrate is concentrated in vacuo. The residue is chromatographed on silica gel using cyclohexane/diethyl ether (10:1). The product thus obtained is crystallized from cyclohexane.

Yield: 13.4 g (78% of theory)

M.p.: 68–75° C.

R$_f$=0.90 (PE:diethyl ether=10:3)

MS (ESI): m/e=662 (M+Na)

Example 299

4-(1-N-Butyl-isoindolinyl-3-oxy)-1-(1-pentylsulphonyl)-amino-benzene hydrochloride

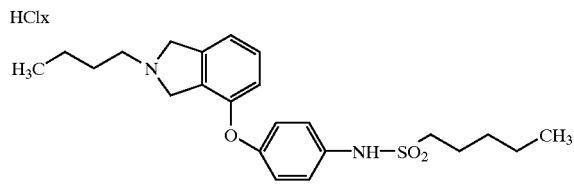

A solution of Example 298 (0.750 g; 1.17 mmol) and n-butylamine (0.858 g; 11.7 mmol) in THF (150 ml) is stirred at room temperature overnight. The batch is treated with 1 N NaOH (5.0 ml) and stirred at 50° C. for 24 h. The solvent is stripped off in vacuo, the residue is taken up in ethyl acetate (50 ml) and the mixture is washed with water (50 ml). The aqueous phase is extracted with ethyl acetate (25 ml) and the combined organic phases are dried (Na$_2$SO$_4$) and concentrated in vacuo. The residue is chromatographed on silica gel using toluene:ethyl acetate (1:1). The amine thus obtained is dissolved in diethyl ether (5 ml) and treated with a saturated solution of HCl in diethyl ether (1 ml). The solvent is stripped off in vacuo and the product is dried in vacuo.

Yield: 0.255 g (47% of theory)

M.p.: 70–73° C. (d.)

R$_f$=0.37 (VII)

MS (DCI, NH$_3$): m/e=417 (M+H)

The examples listed in Table 24 are prepared in analogy to Example 299.

TABLE 24

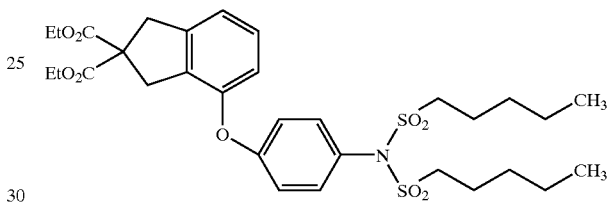

| Ex. | R$^3$ | Yield (% of theory) | R$_f$ | MS |
|---|---|---|---|---|
| 300 | Me | 63 | 0.50 (XXV) | 375 (M + H), B |
| 301 | nPr | 50 | 0.58 (XXV) | 403 (M + H), B |

Example 302

4-[2,2-Bis-(ethoxycarbonyl)-indanyl-4-oxy]-1-[N,N-bis(1-pentylsulphonyl)amino]-benzene

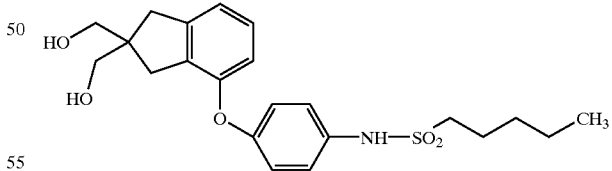

A solution of Example 298 (2.00 g; 3.13 mmol) and diethyl malonate (0.50 g; 3.13 mmol) in 2-butanone (30 ml) is treated with potassium carbonate (1.88 g; 13.6 mmol) and stirred under reflux for 18 h. It is allowed to cool to room temperature and is filtered, and the filtrate is concentrated in vacuo. The residue is chromatographed on silica gel using tol:EA (30:1).

Yield: 0.480 g (24% of theory)

R$_f$=0.53 (X)

MS (ESI): m/e=638 (M+H)

Example 303

4-[2,2-Bis-(hydroxymethyl)-indanyl-4-oxy)-1-[N-1-pentylsulphonyl]amino-benzene

Lithium aluminium hydride, 1 N solution in THF (1.42 ml; 1.42 mmol) is added dropwise under argon at room temperature to a solution of Example 302 (452 mg; 0.71 mmol) in THF (5.0 ml) and the mixture is stirred at room temperature for 18 h. After addition of satd aqueous NH$_4$Cl solution (20 ml), it is extracted with ethyl acetate (1×50 ml, 2×25 ml). The combined org. phases are washed with satd aqueous NaCl solution (25 ml), dried (Na$_2$SO$_4$) and concentrated in vacuo. The residue is chromatographed on silica gel using tol:EA=1:1.

Yield: 149 mg (49% of theory)
M.p.: 135–137° C.
$R_f$=0.25 (VII)
MS (ESI): m/e=442 (M+Na)

Example 304

3-(2,3-Dimethyl-phenyl-1-oxy)-1-(4,4,4-trifluoro-1-butyl-sulphonyl)oxy-benzene

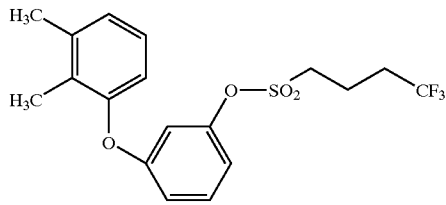

Preparation was carried out in analogy to the preparation of Example 97, starting from Example 150 A (4.54 g; 21.2 mmol).

Yield: 7.80 g (95% of theory)
$R_f$=0.51 (toluene)
MS (DCI, $NH_3$): m/e=406 (M+$NH_4$)

Example 305

3-(2,3-Bis-bromomethyl-phenyl-1-oxy)-1-(4,4,4-trifluoro-1-butylsulphonyl)oxy-benzene

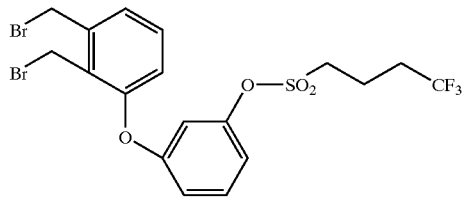

Preparation was carried out in analogy to the preparation of Example 298, starting from Example 304 (6.76 g; 17.4 mmol).

Yield: 7.98 g (84% of theory)
$R_f$=0.71 (IV)
MS (DCI, $NH_3$): m/e=564 (M+$NH_4$)

Example 306

1-(4,4,4-Trifluoro-1-butylsulphonyl)oxy-3-[2,2-bis-(methoxycarbonyl)-indanyl-4-oxy-benzene

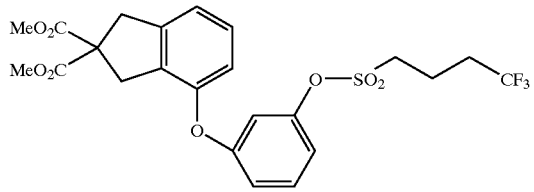

Preparation was carried out in analogy to the preparation of Example 302, starting from Example 305 (6.00 g; 10.2 mmol).

Yield: 1.95 g (37% of theory)

$R_f$=0.45 (X)
MS (DCI, $NH_3$): m/e=534 (M+$NH_4$)

Example 307

1-(4,4,4-Trifluoro-1-butylsulphonyl)oxy-3-(1-N-propylisoindolinyl-3-oxy)-benzene

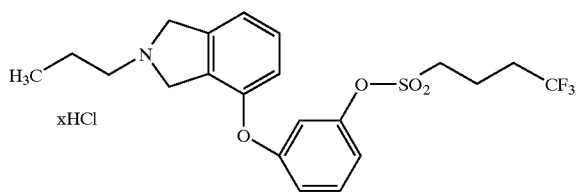

A solution of Example 305 (2.00 g; 3.66 mmol) and n-propylamine (2.16 g; 36.6 mmol) in THF (200 ml) is stirred at room temperature for 5 h. The THF is stripped off in vacuo, the residue is taken up in water and the mixture is extracted with ethyl acetate. The org. phase is extracted with 5% strength aqueous $K_2CO_3$ solution and twice with water, dried (Mg$SO_4$) and concentrated in vacuo. The residue is chromatographed on silica gel using dichloromethane:MeOH=20:1. The amine thus obtained is dissolved in diethyl ether (5 ml) and treated with a satd solution of HCl in diethyl ether (1.5 ml). The solvent is stripped off in vacuo and the residue is triturated with diethyl ether, filtered off and dried in vacuo.

Yield: 0.775 g; (44% of theory)
$R_f$=0.29 (XXXII)
MS (ESI): m/e=444 (M+H)

Example 308

3-(1-Hexyl)oxy-3-(naphthyl-1-oxy)benzene

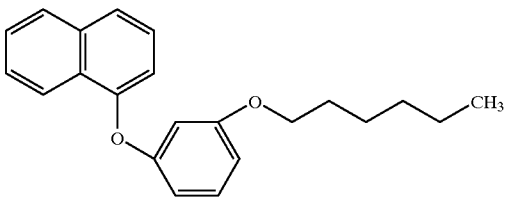

A solution of Example 63 A (300 mg; 1.27 mmol) in acetone (5.0 ml) is treated with potassium carbonate (193 mg; 1.40 mmol) and 1-iodohexane (296 mg; 1.40 mmol) and stirred under reflux for 18 h. The acetone is then stripped off in vacuo, the residue is taken up in water (30 ml) and the mixture is extracted with diethyl ether (3×30 ml). The combined org. phases are dried ($Na_2SO_4$) and concentrated in vacuo. The residue is chromatographed on silica gel using cyclohexane:dichloromethane (4:1).

Yield: 285 mg (69% of theory)
$R_f$=0.50 (PE:dichloromethane=4:1)
MS (DCI, $NH_3$): m/e=321 (M+H)

Example 309

N-1-Hexyl-3-(naphthyl-1-oxy)aniline

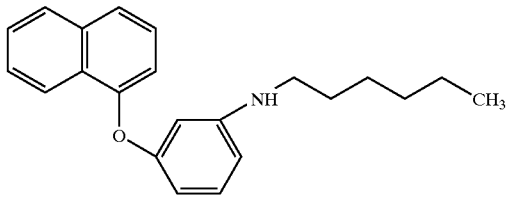

A solution of Example 45 A (1.176 g; 5.00 mmol) and 1-iodohexane (0.509 g, 2.40 mmol) in petroleum ether (10 ml) is heated to reflux overnight. After addition of 1-iodohexane (0.170 g; 0.80 mmol) and THF (4 ml), the mixture is stirred under reflux for a further 3 h. After addition of diethyl ether (50 ml), it is washed with dil. ammonia solution (50 ml) and water (2×50 ml) and dried ($Na_2SO_4$), and the solvent is stripped off in vacuo. The residue is chromatographed on silica gel using cyclohexane:dichloromethane (3:1).

Yield: 0.211 g (28% of theory)

$R_f$=0.86 (IV)

MS (DCI, $NH_3$): m/e=320 (M+H)

What is claimed is:

1. A compound of the formula (I):

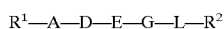  $R^1$—A—D—E—G—L—$R^2$  (I)

in which $R^1$ represents naphth-1-yl, which is optionally substituted by ($C_1$-$C_6$)-alkyl substituted by hydroxyl, ($C_1$-$C_6$)-acylamino, amino or ($C_1$-$C_6$)-alkoxy, indan-4-yl, which is substituted by hydroxy($C_1$-$C_6$)-alkyl, a radical of the formula

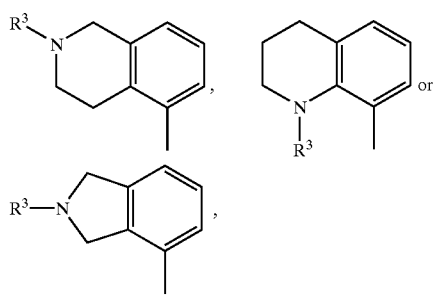

in which $R^3$ is ($C_1$-$C_6$)-alkyl,

E and A represent a bond,

D represents an oxygen atom,

G represents 1,3-phenylene, 1,4-phenylene or 2,5-pyridylene, each of which is optionally substituted by halogen, L represents a radical of the formula —NH—$SO_2$— or —O—$SO_2$— and $R^2$ represents ($C_1$-$C_6$)-alkyl which is optionally substituted by chlorine, trifluoromethyl, by a radical of the formula —O—$CH_2$—$CF_3$ or by phenyl or by pyridyl, which can be substituted by bromine or chlorine, or a salt thereof.

2. A compound according to claim 1, which has one of the following formulae:

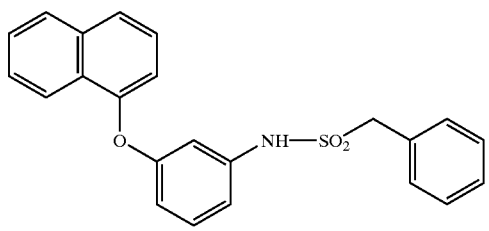

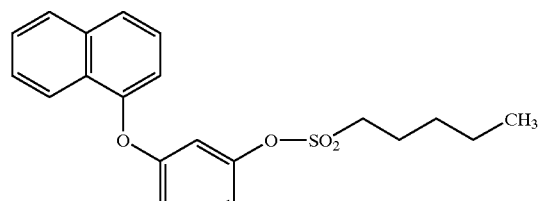

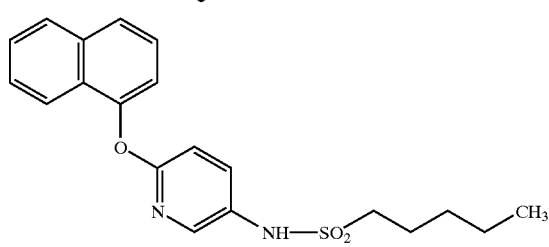

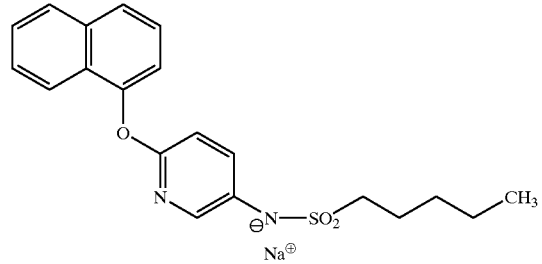

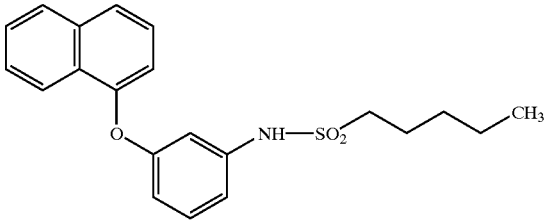

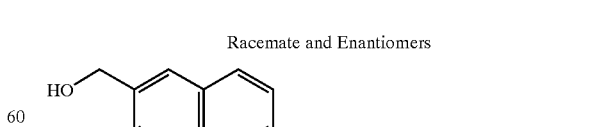

Racemate and Enantiomers

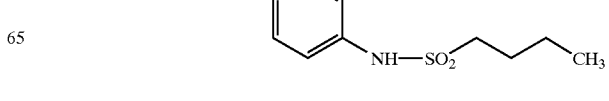

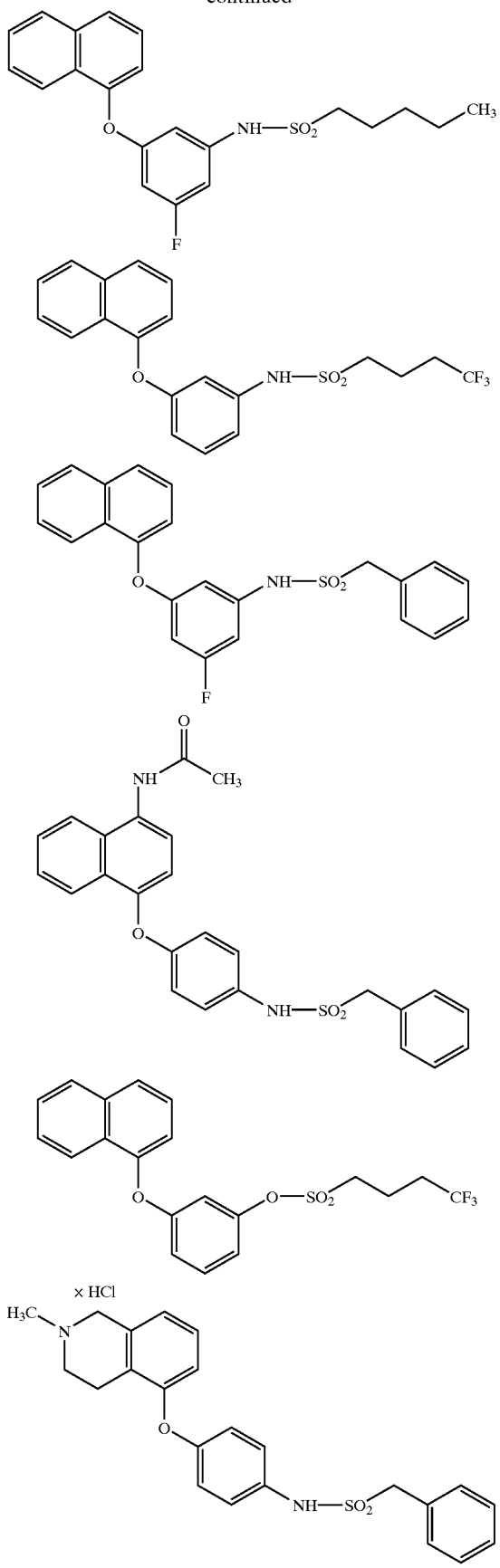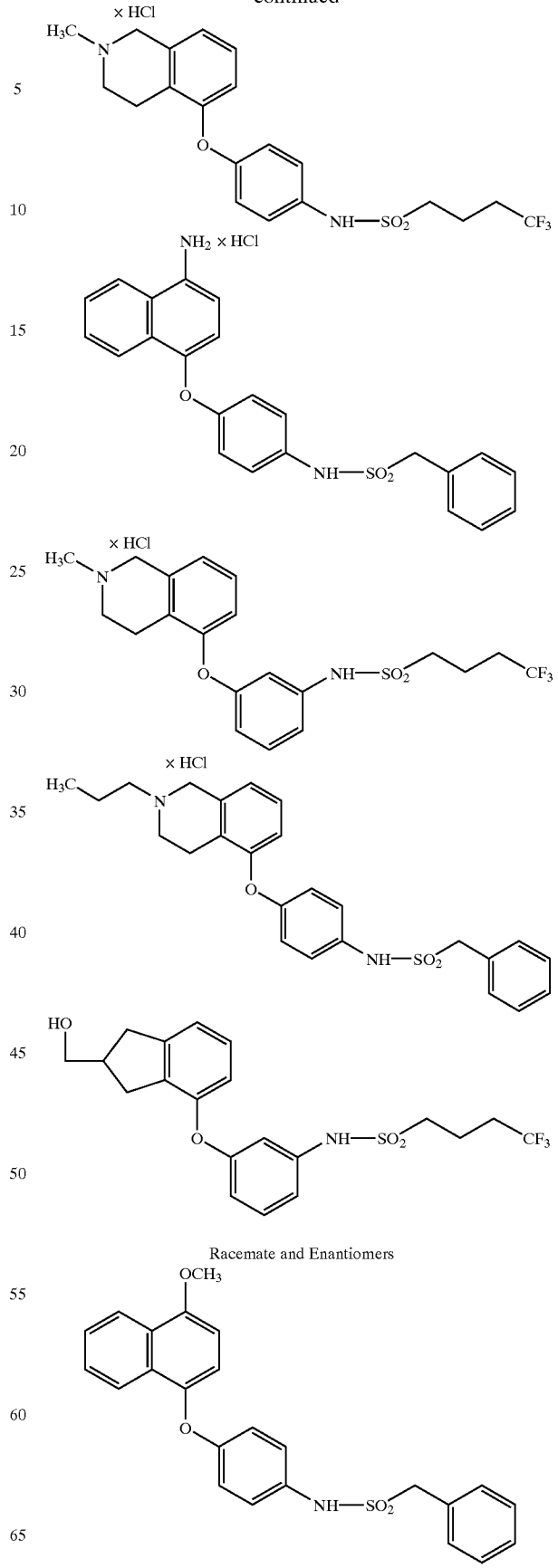
Racemate and Enantiomers

199
-continued
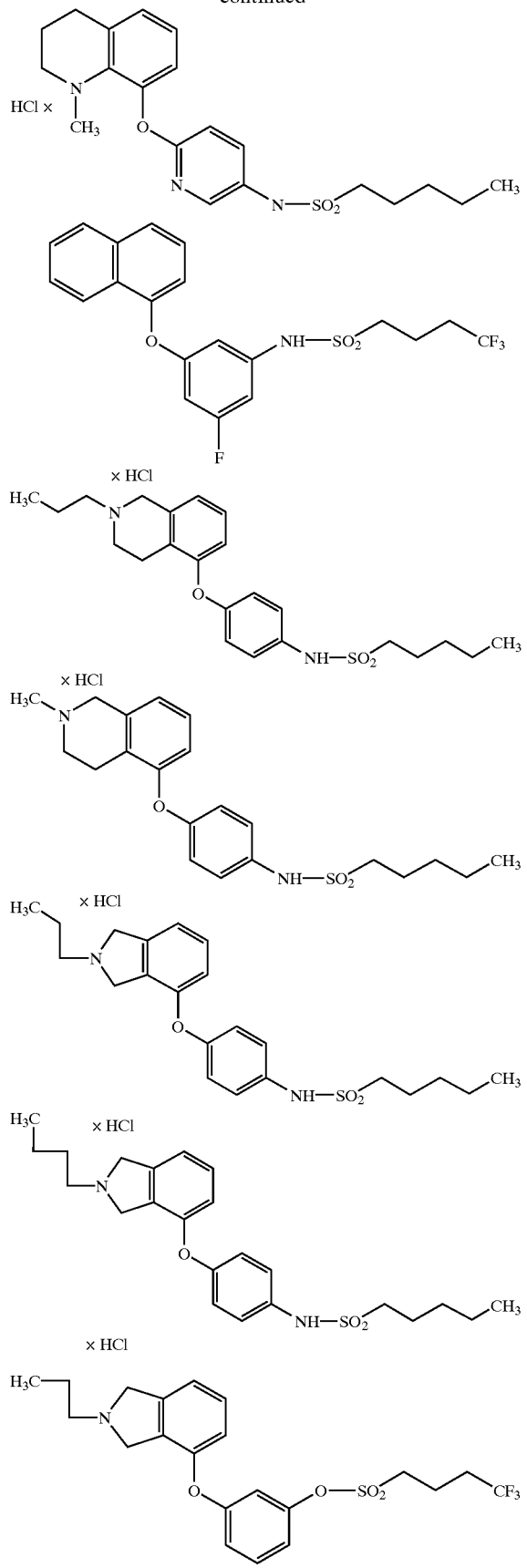
200
-continued
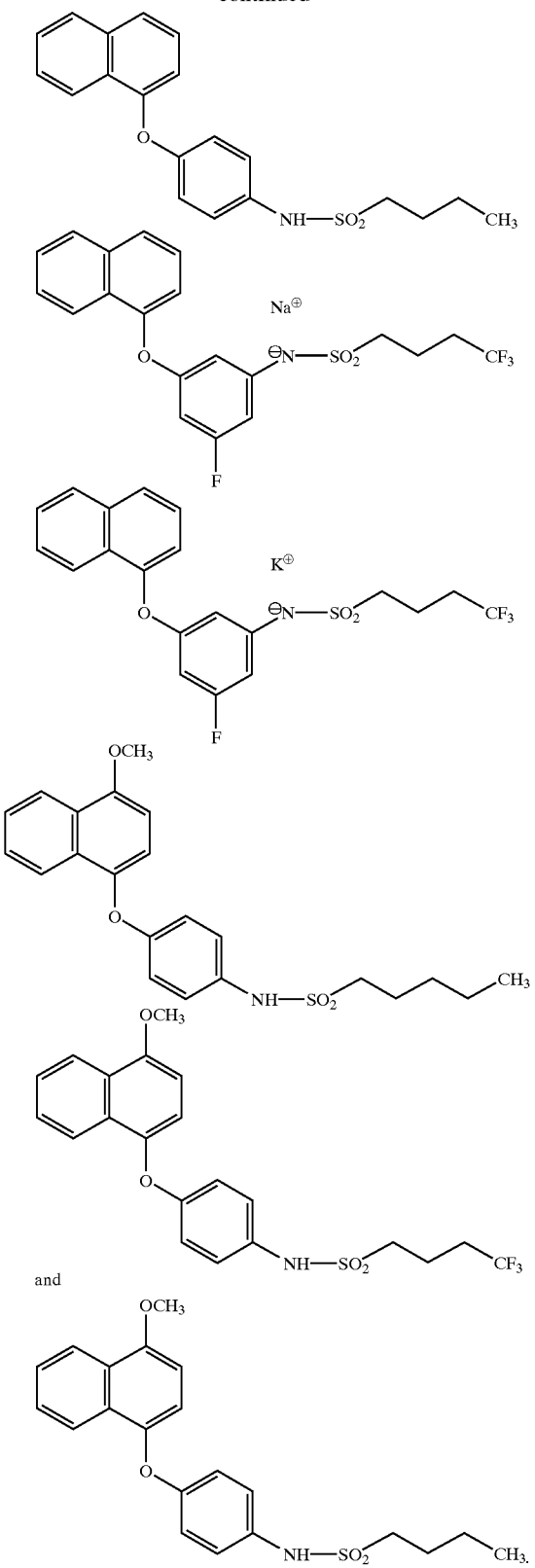
3. A pharmaceutical composition comprising a compound or physiologically acceptable salt thereof according to any one of claims 1 or 2 and a physiologically acceptable carrier.

4. A method for preventing and/or treating a neurodegenerative disorder, said method comprising administering to an individual an effective amount thereof of a compound or physiologically acceptable salt thereof according to any one of claims 1 or 2.

5. A method for preventing or treating cerebral ischaemia and craniocerebral trauma, said method comprising administering to an individual an effective amount therefor of a compound or physiologically acceptable salt thereof according to any one of claims 1 or 2.

6. A method for treating a condition selected from states of pain, nemesis, nausea, glaucoma, asthma, anorexia, convulsions, rheumatism, sedation and mobility disorders, said method comprising administering to an individual an effective amount therefor of a compound or physiologically acceptable salt thereof according to any one of claims 1 or 2.

7. A method for treating a condition selected from bacterial infections, viral infections, autoimmune diseases, and inflammatory or autoimmunologically related diseases of the joints of the bone and muscle apparatus, of the interred and external organs, or the central nervous system, said method comprising administering to an individual an effective amount therefor of a compound or physiologically acceptable salt thereof according to any one of claims 1 or 2.

* * * * *

UNITED STATES PATENT AND TRADEMARK OFFICE
CERTIFICATE OF CORRECTION

PATENT NO. : 6,573,278 B2  
DATED : June 3, 2003  
INVENTOR(S) : Mittendorf et al.

It is certified that error appears in the above-identified patent and that said Letters Patent is hereby corrected as shown below:

Column 202,  
Line 7, "the interred" should read -- the internal --

Signed and Sealed this

Twenty-first Day of September, 2004

JON W. DUDAS  
*Director of the United States Patent and Trademark Office*